(12) United States Patent
Dodge, II et al.

(10) Patent No.: US 7,977,530 B2
(45) Date of Patent: Jul. 12, 2011

(54) ABSORBENT ARTICLES COMPRISING ABSORBENT MATERIALS EXHIBITING DESWELL/RESWELL

(75) Inventors: Richard N. Dodge, II, Appleton, WI (US); Jian Qin, Appleton, WI (US); Scott J. Smith, Greensboro, NC (US); Gonglu Tian, Greensboro, NC (US); Yaru Shi, Greensboro, NC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 332 days.

(21) Appl. No.: 12/215,942

(22) Filed: Jun. 30, 2008

(65) Prior Publication Data

US 2009/0192481 A1 Jul. 30, 2009

Related U.S. Application Data

(60) Provisional application No. 61/063,093, filed on Jan. 30, 2008.

(51) Int. Cl.
*A61F 13/15* (2006.01)

(52) U.S. Cl. ........ 604/367; 364/365; 364/366; 364/368; 364/372; 364/375; 364/377

(58) Field of Classification Search .............. 604/364, 604/367, 365, 366, 368, 372, 375, 377, 376
See application file for complete search history.

(56) References Cited

U.S. PATENT DOCUMENTS

| 3,425,971 A | 2/1969 | Gugliemelli et al. |
|---|---|---|
| 3,661,815 A | 5/1972 | Smith |
| 3,849,241 A | 11/1974 | Butin et al. |
| 3,935,099 A | 1/1976 | Weaver et al. |
| 4,100,324 A | 7/1978 | Anderson et al. |
| 4,251,643 A | 2/1981 | Harada et al. |
| 4,338,371 A | 7/1982 | Dawn et al. |
| 4,578,068 A | 3/1986 | Kramer et al. |
| 4,587,154 A | 5/1986 | Hotchkiss et al. |
| 4,604,313 A | 8/1986 | McFarland et al. |
| 4,605,402 A | 8/1986 | Iskra |
| 4,655,757 A | 4/1987 | McFarland et al. |
| 4,673,402 A | 6/1987 | Weisman et al. |
| 4,699,823 A | 10/1987 | Kellenberger et al. |
| 4,724,114 A | 2/1988 | McFarland et al. |
| RE32,649 E | 4/1988 | Brandt et al. |
| 4,798,603 A | 1/1989 | Meyer et al. |

(Continued)

FOREIGN PATENT DOCUMENTS

EP 0 539 703 A1 5/1993

(Continued)

OTHER PUBLICATIONS

Lawrence, K.D. et al., "An Improved Device For the Formation of Superfine, Thermoplastic Fibers," *NRL Report 5265*, U.S. Naval Research Laboratory, Washington, D.C., Feb. 11, 1959, pp. 1-7.

(Continued)

*Primary Examiner* — Jacqueline F. Stephens
(74) *Attorney, Agent, or Firm* — Bryan R. Rosiejka; Denise L. Stoker

(57) ABSTRACT

The present invention relates to absorbent articles that include absorbent compositions which exhibit swelling, deswelling, and reswelling behavior. More specifically, absorbent compositions of this invention swell and absorb fluids after exposure to aqueous fluids, deswell and release fluids from the swollen absorbent compositions, and can also reswell and absorb fluids. The swelling-deswelling-reswelling behavior allows enhanced liquid distribution in absorbent composites and absorbent articles.

28 Claims, 28 Drawing Sheets

U.S. PATENT DOCUMENTS

| | | | |
|---|---|---|---|
| 4,940,464 A | 7/1990 | Van Gompel et al. |
| 5,147,343 A | 9/1992 | Kellenberger |
| 5,350,624 A | 9/1994 | Georger et al. |
| 5,728,082 A | 3/1998 | Gustafsson et al. |
| 5,766,389 A | 6/1998 | Brandon et al. |
| 6,323,252 B1 | 11/2001 | Gartner et al. |
| 6,362,389 B1 | 3/2002 | McDowall et al. |
| 6,383,960 B1 | 5/2002 | Everett et al. |
| 6,575,952 B2 | 6/2003 | Kirk et al. |
| 6,645,190 B1 | 11/2003 | Olson et al. |
| 6,696,618 B2 | 2/2004 | Dodge, II et al. |
| 2002/0068130 A1 | 6/2002 | Sun et al. |
| 2003/0109840 A1* | 6/2003 | Dodge et al. ............ 604/364 |
| 2003/0139714 A1 | 7/2003 | Sun et al. |
| 2006/0004336 A1 | 1/2006 | Zhang et al. |
| 2008/0269705 A1 | 10/2008 | Kainth et al. |
| 2009/0191408 A1 | 7/2009 | Tian et al. |
| 2009/0192482 A1 | 7/2009 | Dodge, II et al. |

FOREIGN PATENT DOCUMENTS

| | | |
|---|---|---|
| EP | 0 558 889 B2 | 12/1999 |
| EP | 0 944 402 B1 | 2/2003 |
| GB | 2 151 272 A | 7/1985 |
| GB | 2 170 108 A | 7/1986 |
| WO | WO 00/37009 A2 | 6/2000 |
| WO | WO 03/099186 A1 | 12/2003 |

OTHER PUBLICATIONS

Ring, David F. et al., "Fluid Distribution: Comparison of X-Ray Imaging Data," *Nonwovens World*, Summer 1995, pp. 67-70.

Wente, V.A. et al., "Manufacture of Superfine Organic Fibers," *NRL Report 4364*, U.S. Naval Research Laboratory, Washington, D.C., May 25, 1954, pp. 1-15.

* cited by examiner

ABSORBENT ARTICLES COMPRISING ABSORBENT MATERIALS EXHIBITING DESWELL/RESWELL

This patent application claims benefit under 35 U.S.C. 119(e) of U.S. Provisional Application Ser. No. 61/063,093 entitled Absorbent Articles Comprising Absorbent Materials Exhibiting Deswell/Reswell filed in the U.S. Patent and Trademark Office on Jan. 30, 2008. The entirety of provisional application Ser. No. 61/063,093 is hereby incorporated by reference.

BACKGROUND

A superabsorbent polymer is a crosslinked partially neutralized polymer that is capable of absorbing large amounts of aqueous liquids and body fluids, such as urine or blood, with swelling and the formation of hydrogels, and of retaining the fluids under a certain pressure. Superabsorbent polymer compositions may include post-treatment of the superabsorbent polymer such as surface crosslinking, surface treatment, and other treatment. Superabsorbent polymer particles are particles of superabsorbent polymers or superabsorbent polymer compositions. Unless otherwise specified, the acronym "SAP" may be used herein in place of superabsorbent polymer, superabsorbent polymer composition, and particles thereof.

Commercially available superabsorbent polymer compositions typically include crosslinked polyacrylic acids or crosslinked starch-acrylic acid graft polymers, in which some of the carboxyl groups are neutralized with sodium hydroxide solution or potassium hydroxide solution. A primary use of superabsorbent polymer compositions is in absorbent composites that are used in absorbent articles, such as diapers, training pants, incontinence products, or feminine care products. For fit, comfort and aesthetic reasons, and from environmental aspects, there is an increasing trend to make absorbent articles smaller and thinner. This is often accomplished by reducing the content of high volume fluff fiber typically present in these articles. To ensure a constant total retention capacity of body fluids in the sanitary articles, the superabsorbent polymer composition content of the absorbent articles is typically increased.

Fluid distribution in an absorbent composite is generally dependent on: the amount of free liquid available for distribution, the structure and materials of the absorbent composite, and a time factor. However, current absorbent composites useful in absorbent cores of absorbent articles generally have inadequate (or less than desirable) fluid distribution properties. Poor fluid distribution decreases the full utility efficiency of absorbent composites as not all of the superabsorbent polymer composition absorbs the liquid (i.e., the SAP is not fully utilized).

One potential solution known in the art for improving fluid distribution in an absorbent composite is to use superabsorbent polymer compositions having a slow absorbency rate. The theory for using slow absorbency superabsorbent polymer compositions is that there would be diminished or delayed gel blocking and thereby would provide more free liquid, as well as more time for the liquid to distribute away from the insult target zone. However, although distribution may be enhanced using the slow superabsorbent, the absorbent composite typically does not provide necessary leakage protection.

As can be observed in the use of slow absorbency superabsorbent polymer compositions, there is a conflict between the functions of lockup and distribution. One problem is that the time required to lockup liquid into the superabsorbent polymer composition and open-up composite structure by SAP swelling is relatively long. It is the free liquid which is in the target zone during a fluid insult period which is difficult to get into the absorbent product core and is believed to be responsible for leakage of liquid from an absorbent product while in use. To reduce leakage, the superabsorbent material needs to lockup liquid at a rate similar to the liquid delivery rate so that an absorbent product has adequate fluid handling functionality. However, if the superabsorbent polymer composition absorbs the liquid, then distribution of liquid is reduced since there is no free liquid to be distributed after fluid insult.

There is a need for an absorbent composite or an absorbent system that demonstrates the ability for a SAP to quickly lockup liquid and then gradually release this liquid so that it may be distributed to result in desirable leakage and distribution behavior. There is a further need for an absorbent article which exhibits enhanced fluid distribution properties while maintaining enhanced lockup properties, thereby maximizing the absorbing capabilities of the absorbent article and/or its components thereof.

SUMMARY

In response to the needs discussed above, an absorbent article of the present invention comprises an absorbent composite or an absorbent system which exhibits swell/deswell/reswell behavior.

In some aspects, an absorbent composite comprises an absorbent composition. The absorbent composition comprises a SAP, a deswell triggering agent ($TA_D$) and a reswell triggering agent ($TA_R$). In addition, the SAP, the $TA_D$ and the $TA_R$ are all selected from either solubility-based chemistry or neutralization-based chemistry groupings. Furthermore, the absorbent composite has a top side and an opposing bottom side. In some aspects, the SAP, $TA_D$ and $TA_R$ are substantially uniformly distributed within the composite. In some aspects, the absorbent composite further comprises a target zone and a perimeter region; wherein the target zone comprises the SAP, $TA_D$ and $TA_R$; and wherein the perimeter region comprises substantially only the SAP. In some aspects, the the SAP is a superabsorbent polymer composition. In some aspects, the $TA_D$ comprises a first water-soluble solid chemical wherein the $TA_D$ has a release profile for releasing the water-soluble solid chemical, wherein the release profile is selected from a singular release profile or a sigmoidal release profile; wherein the $TA_R$ comprises a second water-soluble solid chemical, wherein the reswell triggering agent has a sigmoidal release profile for releasing the second water-soluble solid chemical; and wherein the first water-soluble chemical has a higher cumulative release than the second water-soluble chemical after exposure to aqueous fluid and before about 100% release. In some aspects, the absorbent composite is present in an absorbent article which further comprises a topsheet and a backsheet, wherein the absorbent composite is disposed between the topsheet and the backsheet. In some aspects, the composite is present in an absorbent article selected from personal care absorbent articles, health/medical absorbent articles, household/industrial absorbent articles or sports/construction absorbent articles.

In some aspects, an absorbent composite has a fibrous matrix and comprises a SAP, a deswell triggering agent ($TA_D$) and a reswell triggering agent ($TA_R$). The SAP, the $TA_D$ and the $TA_R$ are all selected from either solubility-based chemistry or neutralization-based chemistry groupings. In addition, the absorbent composite has a top layer, a middle layer and a bottom layer where the middle layer is disposed between the top layer and the bottom layer, and where each of SAP, $TA_D$ and $TA_R$ is present in at least one of the layers. In some aspects, the the SAP is a superabsorbent polymer composition. In some aspects, the $TA_D$ comprises a first water-soluble solid chemical wherein the $TA_D$ has a release profile for releasing the water-soluble solid chemical, wherein the release profile is selected from a singular release profile or a sigmoidal release profile; wherein the $TA_R$ comprises a second water-soluble solid chemical wherein the reswell triggering agent has a sigmoidal release profile for releasing the second water-soluble solid chemical; and wherein the first water-soluble chemical has a higher cumulative release than the second water-soluble chemical after exposure to aqueous fluid and before about 100% release. In some aspects, the middle layer of the absorbent composite comprises substantially only SAP; the top layer comprises substantially only $TA_D$; and the bottom layer comprises substantially only $TA_R$. In some aspects, the middle layer of the absorbent composite comprises substantially only SAP; the top layer comprises substantially only $TA_D$; the bottom layer comprises substantially only $TA_R$; and at least one of the $TA_D$ and $TA_R$ is located substantially only in a target zone of the top layer and/or bottom layer, respectively. In some aspects, the middle layer of the absorbent composite comprises substantially only SAP; and the top layer and the bottom layer each comprise substantially only $TA_D$ and $TA_R$ combined. In some aspects, the middle layer of the absorbent composite comprises substantially only SAP; the top layer and the bottom layer each comprise substantially only $TA_D$ and $TA_R$ combined; and the $TA_D$ and $TA_R$ are located substantially only in a target zone of at least one of the top layer and bottom layer. In some aspects, the top layer, the middle layer, and the bottom layer of the absorbent composite each comprise substantially only one of the SAP, $TA_D$ and $TA_R$; where none of the layers is the same. In some aspects, the absorbent composite further comprises a first intermediate layer and a second intermediate layer, wherein the first intermediate layer is disposed between the top layer and the middle layer, and wherein the second intermediate layer is disposed between the middle layer and the bottom layer; wherein the top layer, the middle layer, and the bottom layer each comprise substantially only SAP; and wherein the first intermediate layer and the second intermediate layer each comprise SAP, $TA_D$ and $TA_R$. In some aspects, the absorbent composite further comprises a first intermediate layer and a second intermediate layer, wherein the first intermediate layer is disposed between the top layer and the middle layer, and wherein the second intermediate layer is disposed between the middle layer and the bottom layer; wherein the top layer, the middle layer, and the bottom layer each comprise substantially only SAP; wherein the first intermediate layer comprises substantially only $TA_D$; and wherein the second intermediate layer comprises substantially only $TA_R$. In some aspects, the absorbent composite is present in an absorbent article which further comprises a topsheet and a backsheet, wherein the absorbent composite is disposed between the topsheet and the backsheet. In some aspects, the composite is present in an absorbent article selected from personal care absorbent articles, health/medical absorbent articles, household/industrial absorbent articles or sports/construction absorbent articles.

In some aspects, an absorbent system comprises a SAP, a deswell triggering agent ($TA_D$) and a reswell triggering agent ($TA_R$). The SAP, the $TA_D$ and the $TA_R$ are all selected from either solubility-based chemistry or neutralization-based chemistry groupings. The absorbent system further comprises an absorbent composite, a top discrete layer, and a bottom discrete layer; where the absorbent composite includes a fibrous matrix; and where the absorbent composite is disposed between the top discrete layer and the bottom discrete layer. In some aspects, the SAP is a superabsorbent polymer composition. In some aspects, the $TA_D$ comprises a first water-soluble solid chemical wherein the $TA_D$ has a release profile for releasing the water-soluble solid chemical, wherein the release profile is selected from a singular release profile or a sigmoidal release profile; wherein the $TA_R$ comprises a second water-soluble solid chemical wherein the reswell triggering agent has a sigmoidal release profile for releasing the second water-soluble solid chemical; and wherein the first water-soluble chemical has a higher cumulative release than the second water-soluble chemical after exposure to aqueous fluid and before about 100% release. In some aspects, the absorbent composite comprises substantially only the SAP; the top discrete layer comprises substantially only the $TA_D$; and the bottom discrete layer comprises substantially only the $TA_R$. In some aspects, the absorbent composite comprises substantially only the SAP; the top discrete layer comprises substantially only the $TA_D$; the bottom discrete layer comprises substantially only the $TA_R$; and at least one of the $TA_D$ and the $TA_R$ is located substantially only in a target zone of the top discrete layer and/or bottom discrete layer, respectively. In some aspects, the absorbent composite comprises substantially only the SAP; and the top discrete layer and the bottom discrete layer each comprise substantially only the $TA_D$ and the $TA_R$ combined. In some aspects, the the absorbent composite comprises substantially only the SAP; the top discrete layer and the bottom discrete layer each comprise substantially only the $TA_D$ and the $TA_R$ combined; and the $TA_D$ and the $TA_R$ are located substantially only in a target zone of at least one of the top discrete layer and/or bottom discrete layer. In some aspects, the absorbent composite, the top discrete layer, and the bottom discrete layer each comprise exclusively only one of the SAP, the $TA_D$ and the $TA_R$. In some aspects, the absorbent system further comprises a first intermediate discrete layer and a second intermediate discrete layer, wherein the first intermediate discrete layer is disposed between the top discrete layer and the absorbent composite, and wherein the second intermediate discrete layer is disposed between the absorbent composite and the bottom discrete layer; wherein the top discrete layer and the bottom discrete layer each comprise substantially only SAP; wherein the absorbent composite comprises substantially SAP; and wherein the first intermediate discrete layer and the second intermediate discrete layer each comprise the SAP, the $TA_D$ and the $TA_R$ combined. In some aspects, the absorbent system further comprises a first intermediate discrete layer and a second intermediate discrete layer, wherein the first intermediate discrete layer is disposed between the top discrete layer and the absorbent composite, and wherein the second intermediate discrete layer is disposed between the absorbent composite and the bottom discrete layer; wherein the top discrete layer and the bottom discrete layer each comprise substantially only the SAP; wherein the absorbent composite comprises substantially only SAP; wherein the first intermediate discrete layer comprises substantially only the $TA_D$; and wherein the second intermediate discrete layer comprises substantially only the $TA_R$. In some aspects, the absorbent system is present in an absorbent article which further comprises comprising a topsheet and a backsheet, wherein the absorbent system is disposed between the topsheet and the backsheet. In some aspects, the absorbent system is present in an absorbent article selected from personal care absorbent articles, health/medical absorbent articles, household/industrial absorbent articles or sports/construction absorbent articles.

Numerous other features and advantages of the present invention will appear from the following description. In the description, reference is made to exemplary aspects of the invention. Such aspects do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 25A:
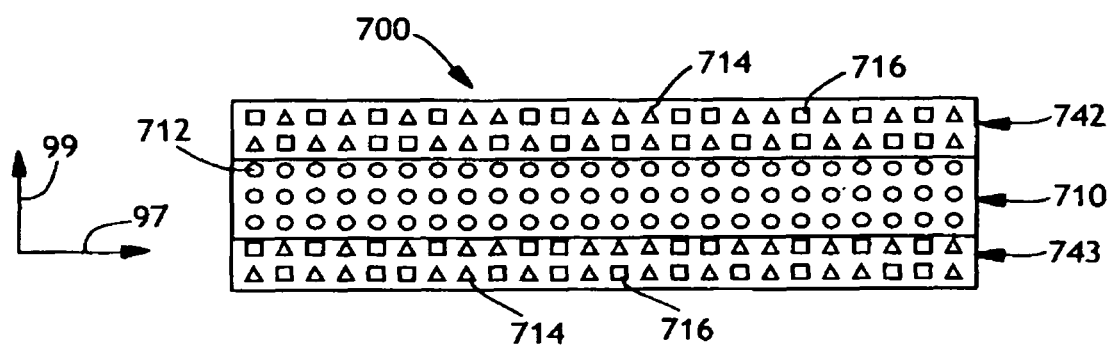
FIG. 25A is a cross-section of an absorbent system in which SAP is uniformly distributed throughout the absorbent composite layer, and a deswell and reswell triggering agent is located substantially only in at least one discrete layer located above and below the absorbent composite layer.
Figure 25B:
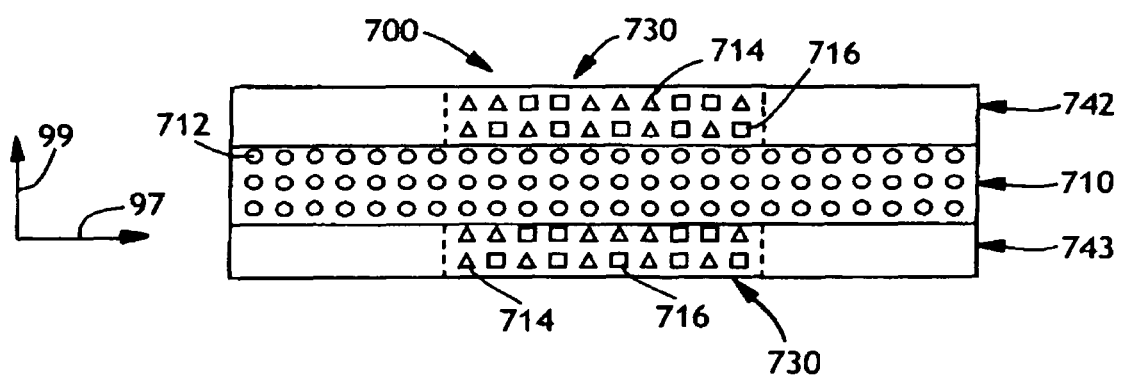
FIG. 25B is a cross-section of an absorbent system in which the deswell and reswell triggering agent is substantially located in a target zone of at least one discrete layer.
Figure 25C:
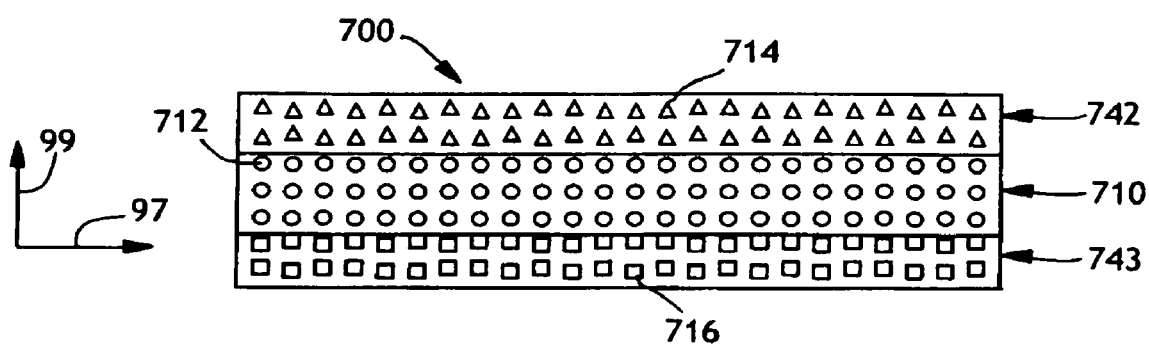
FIG. 25C is a cross-section of an absorbent system in which a deswell triggering agent is located in a discrete layer located above the absorbent composite layer and a reswell triggering agent is located substantially in a discrete layer located below the absorbent composite layer.
Figure 25D:
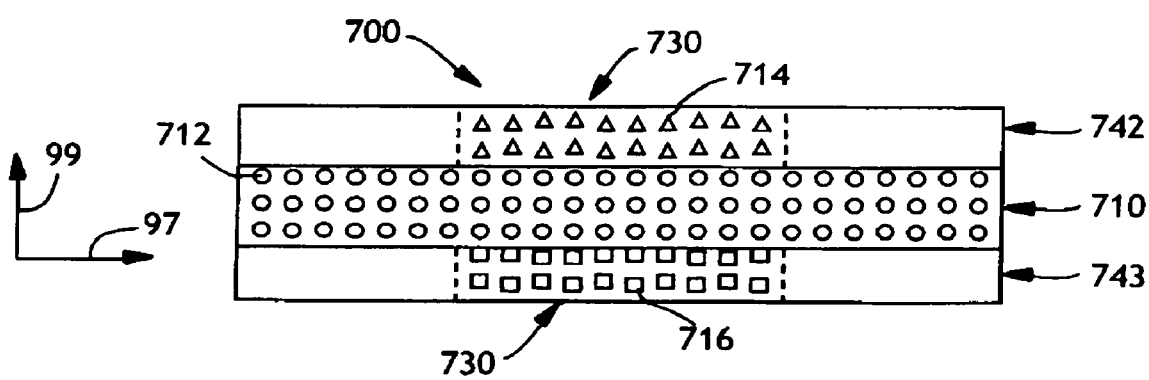
FIG. 25D is a cross-section of an absorbent system in which the triggering agents are each present in a target zone of a discrete layer.
Figure 25E:
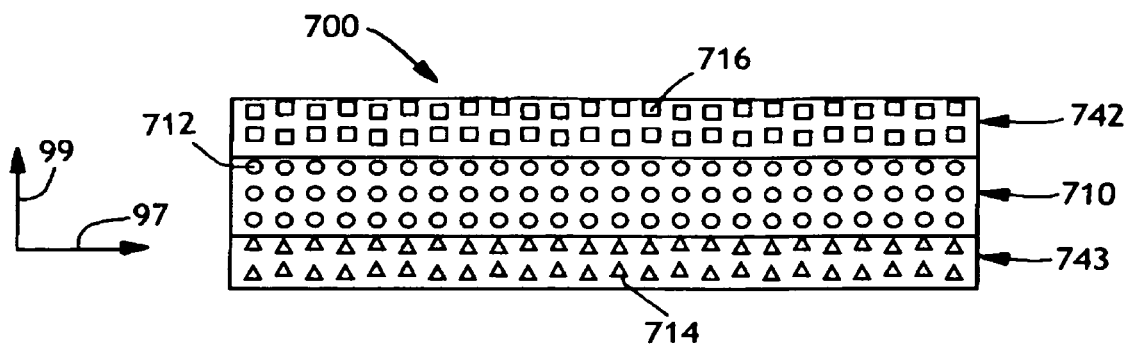
FIG. 25E is a cross-section of an absorbent system in which a reswell triggering agent is located in a discrete layer located above the absorbent composite layer and a deswell triggering agent is located substantially in a discrete layer located below the absorbent composite layer.
Figure 25F:
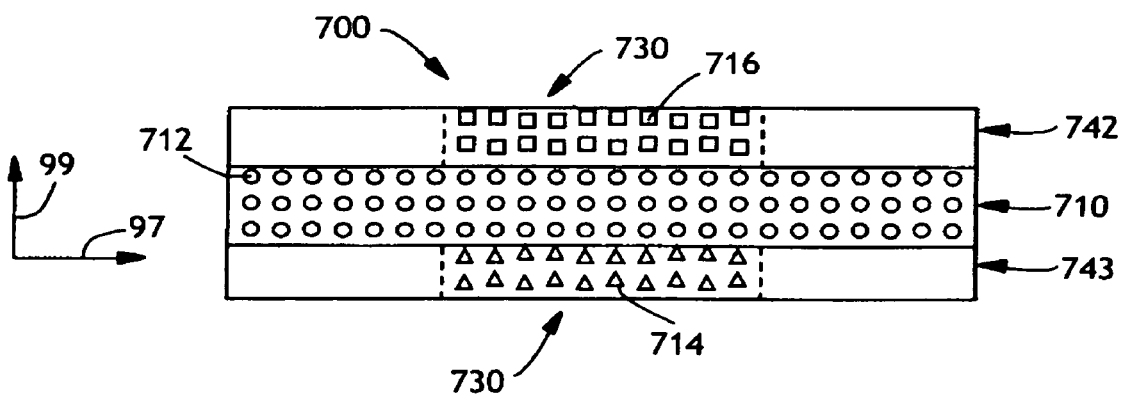
FIG. 25F is a cross-section of an absorbent system in which the triggering agents are each present in a target zone of a discrete layer.
Figure 25G:
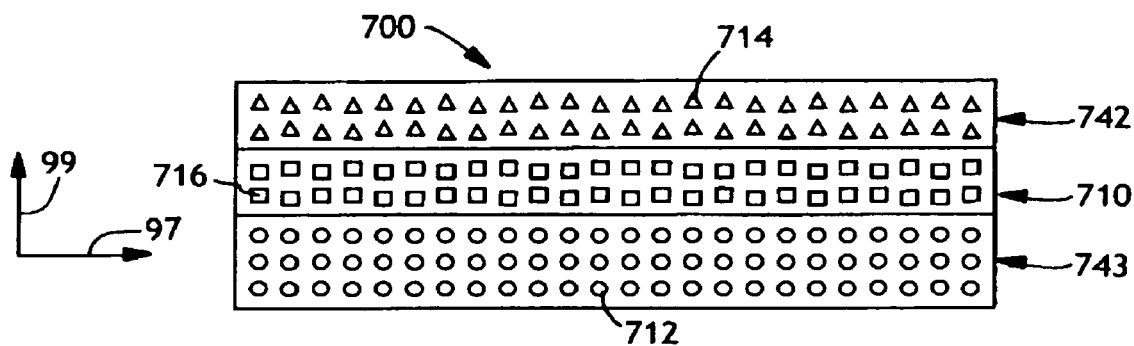
FIG. 25G is a cross-section of an absorbent system in which a reswell triggering agent is located in an absorbent composite layer, a deswell triggering agent is located in a discrete layer above the absorbent composite layer, and SAP is located in a discrete layer below the absorbent composite layer.
Figure 25H:
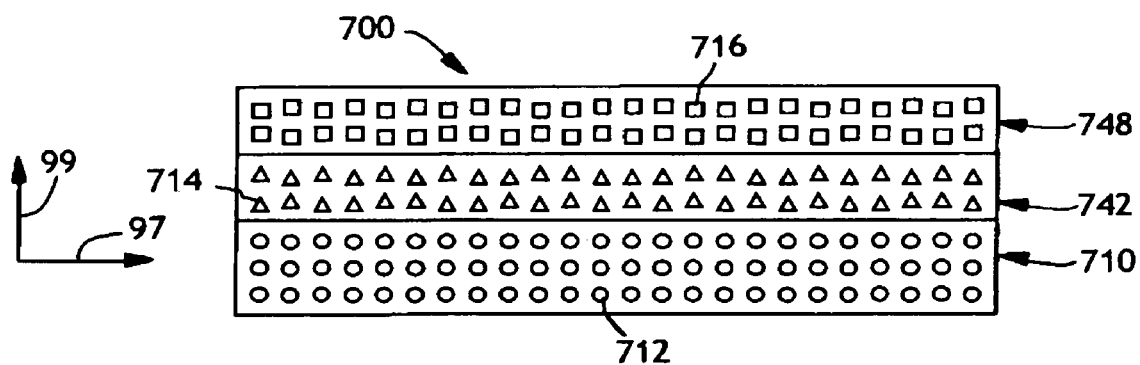
FIG. 25H is a cross-section of an absorbent system in which SAP is located in an absorbent composite layer, a deswell triggering agent is located in a discrete layer above the absorbent composite layer, and a reswell triggering agent is located in an additional layer located above the deswell triggering agent layer.
Figure 25I:
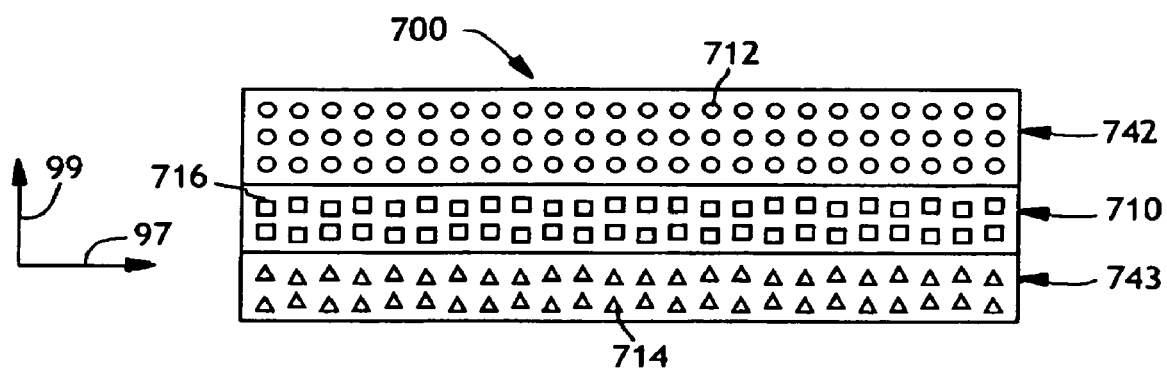
Figure 25J:
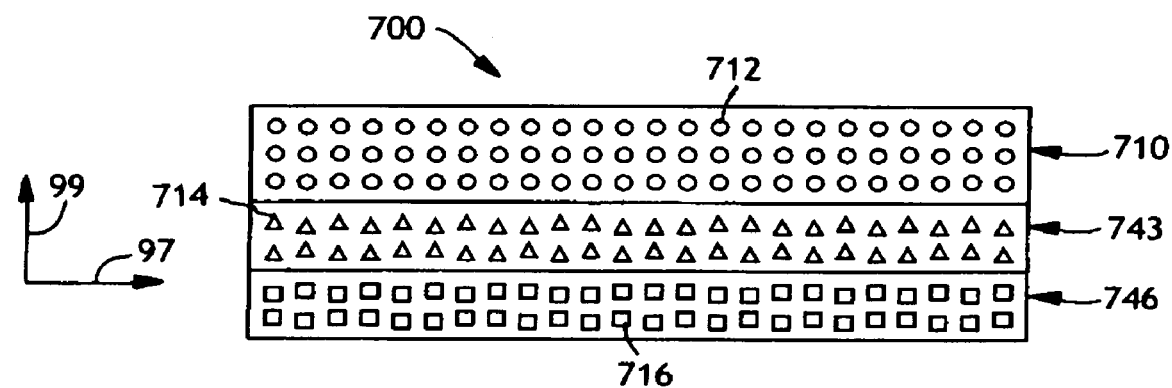

FIG. 25I is a cross-section of an absorbent system in which a reswell triggering agent is located in an absorbent composite layer, SAP is located in a discrete layer above the absorbent composite layer, and deswell triggering agent is located in a discrete layer below the absorbent composite layer; and FIG. 25J is a cross-section of an absorbent system in which a SAP is located in an absorbent composite layer, deswell triggering agent is located in a discrete layer below the absorbent composite layer, and a reswell triggering agent is located in an additional layer below the reswell triggering agent layer.

Repeated use of reference characters in the present specification and drawings is intended to represent the same or analogous features or elements of the present invention.

TEST METHODS

Unless otherwise stated, all tests are conducted at a temperature of 21° C. and a relative humidity between 10% and 60%. Unless otherwise stated, the test fluid used in all the test methods described below is an aqueous 0.9 wt % sodium chloride solution (also referred to herein as "0.9 wt % saline", or merely as "saline") such as that available from Ricca Chemical Company, having a place of business in Arlington, Tex., U.S.A.

Centrifuge Retention Capacity Test

The Centrifuge Retention Capacity (CRC) Test measures the ability of the SAP (or the absorbent composition) to retain liquid therein after being saturated and subjected to centrifugation under controlled conditions. The resultant retention capacity is stated as grams of liquid retained per gram weight of the sample (g/g). The sample to be tested is prepared from particles that are pre-screened through a U.S. standard 30-mesh screen and retained on a U.S. standard 50-mesh screen. As a result, the SAP sample comprises particles sized in the range of about 300 to about 600 microns. The particles may be pre-screened by hand or automatically.

The retention capacity is measured by placing about 0.2 grams of the pre-screened SAP (or the absorbent composition) sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper is suitable. The bag is formed by folding a 12.7 cm by 7.6 cm sample of the bag material in half and heat-sealing two of the open edges to form a 6.4 cm by 7.6 cm rectangular pouch. The heat seals are about 0.6 inches inside the edge of the material. After the sample is placed in the pouch, the remaining open edge of the pouch is also heat-sealed. Empty bags are also made to serve as controls. Three samples are prepared for each sample to be tested.

The sealed bags are submerged in a pan containing the test solution at about 23° C., making sure that the bags are held down until they are completely wetted. After wetting, the samples remain in the solution for about 30 minutes, at which time they are removed from the solution and temporarily laid on a non-absorbent flat surface.

The wet bags are then placed into the basket, wherein the wet bags are separated from each other and are placed at the outer circumferential edge of the basket, wherein the basket is of a suitable centrifuge capable of subjecting the samples to a G-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target G-force of about 290 g-force with a variance from about 280 to about 300 g-force), for 3 minutes. G-force is defined as a unit of inertial force on a body that is subjected to rapid acceleration or gravity, equal to 9.75 m/sec$^2$ at sea level. The bags are removed and weighed, with the empty bags (controls) being weighed first, followed by the bags containing the SAP or the absorbent composition samples. The amount of solution retained by the sample, taking into account the solution retained by the bag itself, is the centrifuge retention capacity (CRC) of the SAP or the absorbent composition, expressed as grams of fluid per gram of SAP or absorbent composition. More particularly, the retention capacity is determined by the following equation:

$$\text{sample/bag after centrifuge} - \text{empty bag after centrifuge} - \text{dry sample weight}\ \text{dry sample weight}$$

The three samples of a desired SAP or absorbent composition are tested, and the results are averaged to determine the Centrifuge Retention Capacity (CRC) of the material. Deviation of measurements of CRC may be ±0.5.

Superabsorbent Polymer pH Test

This test measures the pH of a solution of SAP (or absorbent composition) in 0.9 wt % saline.

Materials Needed:
1. pH meter.
2. pH electrode (Brinkman, Unitrode, PN#20910674 or equivalent)
3. 250 ml beaker.
4. Stir Plate capable of 500 rpm.
5. Stir Bar (approximately 3 cm).
6. 0.9 wt % Saline (Aqueous Sodium Chloride Solution, part number 7213.09-5 from Ricca, or equivalent).)
7. Weigh boat.
8. Balance (accurate to 0.0001 grams).
9. Timer (NIST traceable).
10. Graduated Cylinder (class A, 100 ml capacity)
11. UltraPure water Procedure:
1. Obtain a 250 ml beaker.
2. Measure 150 ml of 0.9 wt % saline into a graduated cylinder, and pour the saline into the 250 ml beaker.

3. Place a stir bar into the beaker.
4. Place the weigh boat onto the balance and tare.
5. Weigh 1.0 g±0.001 superabsorbent into the weigh boat.
6. Pour the sample into the 250 ml beaker.
7. Label the beaker with a sample I.D.
8. Place the beaker onto the stir plate at 500 rpm.
9. Start the timer and set for 3 minutes. Allow the sample to stir for 3 min.
10. When 3 min has expired, immerse the pH electrode into the beaker.
11. Continue to gently stir the sample.
12. Set the timer for 6 min.
13. Start the timer and measure the pH.
14. When time (i.e., 6 min) has expired, record the measured value.
15. Remove the pH electrode from the sample and rinse thoroughly with ultrapure water.

Vortex Time Test
General Description

The vortex test measures the amount of time in seconds required for 2 grams of a SAP or absorbent composition to close a vortex created by stirring 50 milliliters of saline solution at 600 revolutions per minute on a magnetic stir plate. The time it takes for the vortex to close is an indication of the free swell absorbing rate of the SAP or absorbent composition.

Equipment & Materials
1. Beaker, 100 milliliter.
2. Programmable magnetic stir plate, capable of providing 600 revolutions per minute (such as a Dataplate®, Model #721, commercially available from PMC Industries).
3. Magnetic stir bar without rings, 7.9 millimeters×32 millimeters, Teflon covered (such as S/PRIM. brand single pack round stirring bars with removable pivot ring, available from Baxter Diagnostics).
4. Stopwatch.
5. Balance, accurate to ±0.0.01 gram.
6. Saline solution, 0.87 wt % Blood Bank Saline available from Baxter Diagnostics (considered for this test to be the equivalent of 0.9 wt % saline).
7. Weighing paper.
8. Room with standard condition atmosphere (Temperature=23° C.±1° C. and Relative Humidity=50%±0.2%).

Test Procedure:
1. Measure 50 g±0.01 gram of the saline solution into the 100 milliliter beaker.
2. Place the magnetic stir bar into the beaker.
3. Program the magnetic stir plate to 600 revolutions per minute.
4. Place the beaker on the center of the magnetic stir plate such that the magnetic stir bar is activated. The bottom of the vortex should be near the top of the stir bar.
5. Weigh out 2 grams±0.01 gram of the polymer sample (i.e., SAP or absorbent composition) to be tested on weighing paper.
   NOTE: The sample is tested as received (i.e. as it would go into an absorbent composite such as those described herein). No screening to a specific particle size is done, though the particle size is known to have an effect on this test.
6. While the saline solution is being stirred, quickly pour the SAP or absorbent composition to be tested into the saline solution and start the stopwatch. The sample to be tested should be added to the saline solution between the center of the vortex and the side of the beaker.
7. Stop the stopwatch when the surface of the saline solution becomes flat and record the time.
8. The time, recorded in seconds, is reported as the Vortex Time.

Swell/Deswell/Reswell Test

The Swell/Deswell/Reswell Test is intended to measure the liquid absorption capacity of the absorbent composition versus time.

Figure 1:
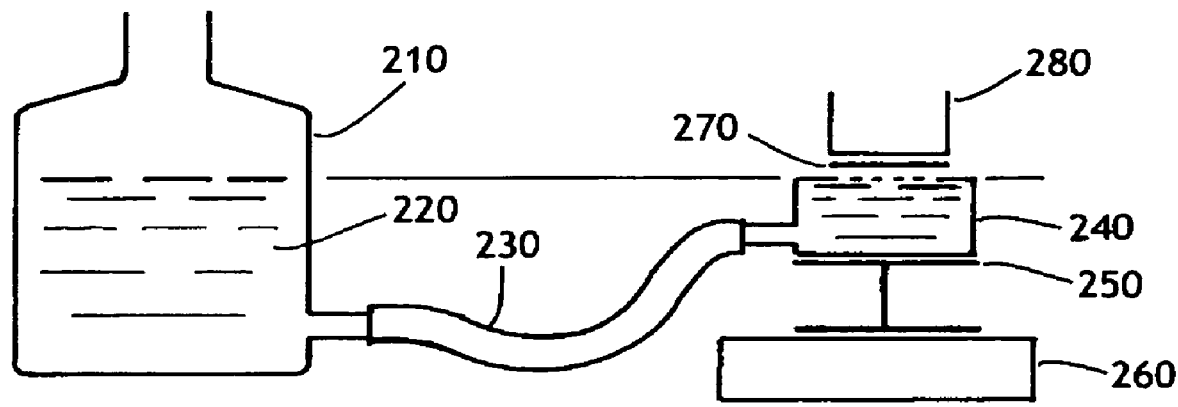
FIG. 1 is an apparatus for the Swell/Deswell/Reswell Test.

A suitable apparatus for this test is shown in FIG. 1. At one end of this apparatus is a fluid reservoir 210 containing 0.9% saline solution. The other end of the apparatus is a cylinder 280 for holding absorbent composition, and a small plastic box 240 for delivering saline solution to the absorbent composition. For example, a Plexiglas cylinder (cylinder inner diameter=25 mm; height=33 mm) with screen filter cloth on bottom (400 mesh=36 microns) can be used for the test. The top plate of box 240 has holes (ca. 1 mm diameter) on it. A piece of filter paper 270 is placed between cylinder 280 and box 240 to ensure good contact of absorbent composition with saline solution. Box 240 is placed on a stand 250 on an electronic balance 260 which is connected to a computer for recording the weight change of absorbent composition during the measurement. Box 240 is connected to reservoir 210 through a flexible tubing 230.

Prior to measurement, the height of reservoir 210 is adjusted to a proper level so that the liquid surface in reservoir 210 is at the same level as the top surface of box 240.

The Test is Started By:
1. adding 0.16 grams of the test sample into cylinder 280 and placing a plastic piston on the top of the test sample;
2. placing the cylinder on box 240 such that the bottom of the cylinder is in contact with the liquid; and
3. immediately starting recording the weight change of the test sample.

The test is stopped after 240 minutes. The absorption capacity of the absorbent material is calculated by dividing the liquid uptake by the weight of the superabsorbent polymer in the absorbent composition. The swell/deswell/reswell curve is generated by plotting the absorption capacity versus time.

Release Profile Measurement Test
Release of Coated Sulfamic Acid Test

The release of sulfamic acid is determined by soaking the coated sulfamic acid in deionized water at room temperature (23° C.) and measuring the pH of the solution using an ORION pH meter (Model No. 290A) and a pH electrode (Model No. ORION 8-172BNWP).

The coated sulfamic acid (2.00 g) is sealed in a teabag. A heat-sealable tea bag material, such as that available from Dexter Corporation (having a place of business in Windsor Locks, Conn., U.S.A.) as model designation 1234T heat sealable filter paper is suitable. 1800 g of deionized water is added into a glass beaker with a magnetic stirring bar (10 mm×70 mm). The beaker is placed on a magnetic stirrer, and the solution is stirred at 200 rpm. The teabag is soaked in the water. A small amount of liquid (about 20 g) is taken out at desired intervals (such as every 2 minutes, or every 5 minutes, or every 10 minutes, or every 20 minutes, for example). The actual weight of solution removed is recorded. The pH of the removed solution is measured with the pH meter. The data from the electrode is converted to concentration of released sulfamic acid by using the calibration curve generated with standard solutions of sulfamic acid. The percentage of the released sulfamic acid is calculated based on the weight of released sulfamic acid and the total weight of sulfamic acid in the coated sample.

Release of Coated Calcium Formate Test

The release of calcium formate is determined according to the same procedure as for the Release of Coated Sulfamic Acid Test, except that the concentration of released calcium formate is measured using a Varian Inductively Coupled Plasma (Model No. Vista MPX Radical).

Release of Coated Sodium Carbonate Test

The release of sodium carbonate is measured according to the same procedure as for the Release of Coated Sulfamic Acid Test, except that the released sodium carbonate is determined by following the release of sodium ion using an Accumet sodium selective electrode (Available from Fisher Scientific, #13-620-503).

Cradle Intake Test

This test utilizes x-ray imaging to determine the amount of fluid located in various locations of the absorbent composite or the absorbent system. X-ray imaging is known in the art as discussed, for example, in an article entitled "Fluid Distribution: comparison of X-ray Imaging Data" by David F. Ring, Oscar Lijap and Joseph Pascente in Nonwovens Worldmagazine, summer 1995, at pages 65-70, which is incorporated herein by reference in a manner that is consistent herewith. Generally, this procedure compares the gray scale x-ray images of a wet and dry sample in order to calculate the liquid content at various locations. Such x-ray systems are available, for example, from Precision X-ray Inc., having a place of business located at 31 Business Park Drive, Branford, Conn., U.S.A. as model no. 10561 HF 100 with enclosure. This system may use image analysis software from Optimus Inc., having a place of business located at Ft. Collins, Colo., U.S.A. as BIO-SCAN OPTIMATE S/N OPM4101105461 version 4.11, or equivalent. The x-ray system is operated with an exposure time of 1.5 seconds, with a tube voltage of 40 Kv and current of 16 mA. The absorbent composite or absorbent system sample is kept in the cradle configuration during x-ray imaging.

Figure 2:
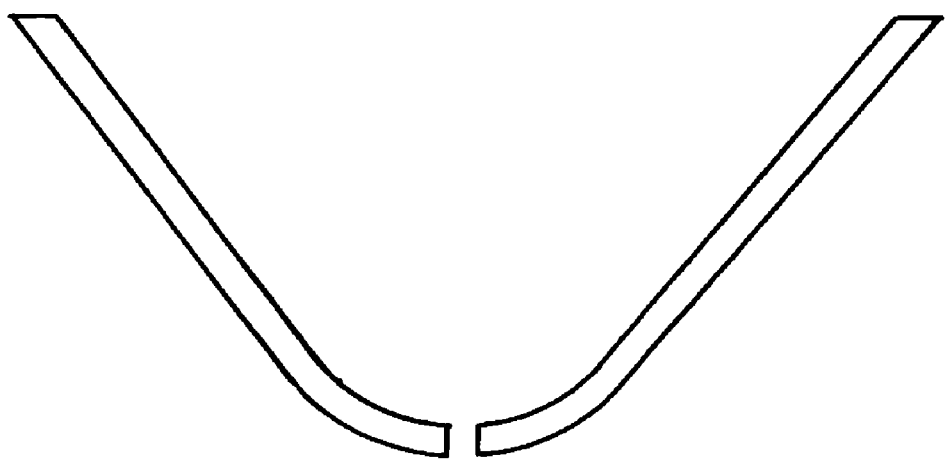
FIG. 2 is a side view of an apparatus used for the Cradle Intake Test.

Procedure:
1. Absorbent composite samples (or absorbent system samples), measuring 7.6 cm wide by 38.1 cm, are placed into a U-shaped cradle (FIG. 2) such that the mid-point of the length direction is positioned at the bottom of the cradle.
2. A peristaltic pump (such as a Masterflex-Digistaltic model #7526-00 available from Cole-Parmer, having a place of business in Barrington, Ill., U.S.A.) is used to deliver 70 cc of 0.9% saline solution at a rate of 15 cc/sec. Saline solution is dispensed through a nozzle with a 3.0 mm diameter opening. Liquid is added at a target point which corresponds to the mid-point of the sample in the length and width direction.
3. 50 minutes after the liquid delivery an x-ray image of the sample is taken to measure how the saline solution is distributed throughout the absorbent composite or absorbent system.
4. 60 minutes after the first liquid delivery, a second liquid delivery and x-ray image is taken, repeating steps 2-3.
5. 60 minutes after the second liquid delivery, a third liquid delivery and x-ray image is taken, repeating steps 2-3.
6. Three replicates of each sample are tested and an average fluid distribution profile is determined by averaging the x-ray images of each of the replicates.

Horizontal Distribution Test
1. A sample (absorbent composite or absorbent system of the present invention) 2.5 cm wide by 38.1 cm is placed onto a flat, horizontal surface
2. 0.9 wt % saline solution is added to the sample at a target point corresponding to the midpoint of the length and width direction. The saline solution is added by use of a funnel and stopcock system suspended over the sample. The saline solution is added at a rate sufficient such that minimal pooling occurs on the surface of the sample.
3. 20 cc of 0.9 wt % saline solution is added to the sample and allowed to be absorbed into and distributed through the sample.
4. 50 minutes after the liquid delivery, the length of the sample which is wetted by the saline solution is observed visually.
5. 60 minutes after the first liquid delivery, a second liquid delivery and wetted length measurement is conducted, repeating steps 3-4.
6. 60 minutes after the second liquid delivery, a third liquid delivery and wetted length measurement is conducted, repeating steps 3-4.
7. 3 replicates of each sample are tested and the average wetted length after each insult is determined.

Horizontal Intake and Distribution Test

This test utilizes x-ray imaging to determine the amount of fluid located in various locations of a sample (i.e., absorbent composite or absorbent system). X-ray imaging is known in the art as discussed, for example, in an article entitled "Fluid Distribution: comparison of X-ray Imaging Data" by David F. Ring, Oscar Lijap and Joseph Pascente in Nonwovens Worldmagazine, summer 1995, at pages 65-70, which is incorporated herein by reference in a manner that is consistent herewith. Generally, this procedure compares the gray scale x-ray images of a wet and dry sample in order to calculate the liquid content at various locations. Such x-ray systems are available, for example, from Precision X-ray Inc. (having a place business located at 31 Business Park Drive, Branford, Conn., U.S.A.) as model no. 10561 HF 100 with enclosure. This system may use image analysis software from Optimus Inc. (having a place of business located at Ft. Collins, Colo., U.S.A.) as BIO-SCAN OPTIMATE S/N OPM4101105461 version 4.11, or equivalent. The x-ray system is operated with an exposure time of 1.5 seconds, with a tube voltage of 40 Kv and current of 16 mA. The absorbent sample is kept in a horizontal, flat configuration during x-ray imaging.

Procedure:
1. A sample (absorbent composite or absorbent system), 7.6 cm wide by 38.1 cm long is placed onto a flat, horizontal surface.
2. A fixture comprising a 2.5 cm inner diameter tube, with a flanged bottom which can rest on the sample is placed such that the center of the inner diameter of the tube corresponds with the midpoint of the length and width direction of the sample.
3. 70 cc of saline solution is poured into the tube and allowed to soak into sample.
4. 50 minutes after the liquid delivery, the length of the sample that is wetted by the saline solution is measured using x-ray densitometry images.
5. 60 minutes after the first liquid delivery, a second liquid delivery and wetted length determination is conducted, repeating steps 3-4.
6. 60 minutes after the second liquid delivery, a third liquid delivery and wetted length determination is conducted, repeating steps 3-4.
7. Three replicates of each sample are tested and the average wetted length after each insult is determined.

Mannequin Test

The Mannequin Test procedure involves placing an absorbent article onto a static mannequin representing the torso of an appropriate sized human. Suitable mannequins can be obtained, for example, from Coutray Consulting, having a place of business located in Douai, France. Fluid is added to the product by way of tubing running through the interior of the mannequin. Once liquid leaks from the product, it is detected by sensors that stop the liquid addition to that product. The amount of liquid added to the product when it leaks can be determined by weighing the products before and after they are removed from the mannequin.

Products can be evaluated for their leakage performance using the Mannequin Test procedure disclosed herein. Saline leakage performance is tested on a static mannequin system. The static mannequin system can be used in a forced leakage protocol in which the mannequin remains in the same position for the evaluation, in this case in the prone position (simulating the condition when the product user is laying on his/her stomach). The mannequin system uses a computer controlled set of valves and sensors to automatically deliver fluid to a particular mannequin and determine when a leakage event has occurred. The amount of liquid added and the frequency of liquid addition can be controlled. For a particular test, these conditions can be fixed. When a product has leaked, as indicated by a sensor or visually seeing the leak, it is removed and weighed to determine the amount of fluid that has been absorbed (i.e. load at leak). After removal of the products from the mannequins, the products can be x-rayed for fluid distribution.

This test utilizes x-ray imaging to determine the amount of fluid located in various locations of the absorbent system. X-ray imaging is known in the art as discussed, for example, in an article entitled "Fluid Distribution: comparison of X-ray Imaging Data" by David F. Ring, Oscar Lijap and Joseph Pascente in Nonwovens Worldmagazine, summer 1995, at pages 65-70, which is incorporated herein by reference in a manner that is consistent herewith. Generally, this procedure compares the gray scale x-ray images of a wet and dry sample in order to calculate the liquid content at various locations. Such x-ray systems are available, for example, from Precision X-ray Inc. (having a place business located at 31 Business Park Drive, Branford, Conn., U.S.A.) as model no. 10561 HF 75 with enclosure. This system may use image analysis software from Optimus Inc. (having a place of business located at Ft. Collins, Colo., U.S.A.) as BIO-SCAN OPTIMATE S/N OPM4101105461 version 6.1, or equivalent.

The Procedure is as Follows:
1. The diaper to be tested is placed onto an appropriately sized infant mannequin which is equipped with tubing that allows delivery of saline solution to the product in an anatomically accurate location.
2. The mannequin, with the diaper installed, is placed into a prone (on the stomach) position.
3. 70 cc of saline solution is added at a target location, corresponding to 11.4 cm from the front edge of the absorbent system. For the other half of the products to be tested, 35 cc of saline solution is added to the same target location.
4. The saline solution is added at 15 cc/sec using a peristaltic pump (such as a Masterflex-Digistaltic model #7526-00 available from Cole-Parmer, having a place of business in Barrington, Ill., U.S.A.) and an anatomically representative male genital with a nozzle inside diameter of 3.1 mm.
5. Every hour an additional 70 cc insult of saline solution is added to the product, using the above pump and nozzle system.
6. When the product leaks liquid, the product is removed from the mannequin.
7. After laying the used product out flat and horizontally, an x-ray image is taken of the used product. Exposure time, voltage, and current during the x-ray images are 5.0 seconds, 23 kV, and 14 ma. The area where liquid exists in the product is determined from the x-ray image

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain various fluids discharged from the body.

The term "absorbent composite" is used herein to refer to a mixture of SAP and/or triggering agents with a carrier matrix including, but not limited to, fibers, foams, nonwovens, films, or other carrier materials.

The term "absorbent composition" refers to a combination of SAP and at least one triggering agent to achieve swell-deswell-reswell behavior of the present invention.

The term "absorbent system" is used herein to refer to a combination of an absorbent composite and at least one additional discrete layer which comprises at least one triggering agent and/or SAP in which such layer is in direct physical contact with a surface of the absorbent composite. The additional discrete layer may consist solely of the SAP and/or triggering agent, or may be a surge layers adhesive layer, tissue layer, foam layer, adhesive/tissue laminate, and the like which comprises the SAP and/or triggering agent.

The term "active agent" refers to the chemical released by a triggering agent which interacts with a SAP to cause deswell and/or reswell behavior.

The term "coating" is used herein to mean a layer of any substance spread over a surface.

The term "complexing" is used herein to describe the forming of molecules by the combination of ligands (such as anions) and metal ions.

The term "crosslinked" used in reference to SAP refers to any means for effectively rendering normally water-soluble materials substantially water-insoluble but swellable. Such a crosslinking means may include, for example, physical entanglement, crystalline domains, covalent bonds, ionic complexes and associations, hydrophilic associations such as hydrogen bonding, hydrophobic associations, or Van der Waals forces.

The term "current" when used as a time reference refers to a time period of approximately the priority date of the present application.

The term "desorb" is used herein to mean the release of fluids from a SAP.

The term "deswell" is used herein to refer to the decrease in size of a SAP that occurs while fluids are being desorbed from the SAP.

The term "disposable" is used herein to describe items such as absorbent articles that are not intended to be laundered or otherwise restored or reused (e.g., as an absorbent article) after a single use.

The term "dry" when referring to a SAP generally refers to the SAP having less than about 10% moisture.

The term "health/medical absorbent articles" includes a variety of professional and consumer healthcare products including, but not limited to, products for applying hot or cold therapy, medical gowns (i.e., protective and/or surgical gowns), surgical drapes, caps, gloves, face masks, bandages, wound dressings, wipes, covers, containers, filters, disposable garments and bed pads, medical absorbent garments, underpads, and the like.

The term "household/industrial absorbent articles" includes construction and packaging supplies, products for cleaning and disinfecting, wipes, covers, filters, towels, disposable cutting sheets, bath tissue, facial tissue, nonwoven roll goods, home-comfort products including pillows, pads, mats, cushions, masks and body care products such as products used to cleanse or treat the skin, laboratory coats, coveralls, trash bags, stain removers, topical compositions, pet care absorbent liners, laundry soil/ink absorbers, detergent agglomerators, lipophilic fluid separators, and the like.

The term "multivalent ions" is used herein to mean an electrically charged atom or group of atoms formed by the loss or gain of multiple electrons, as a cation (positive ion), which is created by a loss of one or more electrons, or as an anion (negative ion), which is created by a gain of one or more electrons.

The terms "particle," "particulate," and the like, when used with respect to the absorbent composition of the present invention refer to the form of discrete units. The units may comprise flakes, fibers, agglomerates, granules, powders, spheres, pulverized materials, or the like, as well as combinations thereof. The particles may have any desired shape: for example, cubic, rod-like, polyhedral, spherical or semi-spherical, rounded or semi-rounded, angular, irregular, etc. Shapes having a high aspect ratio, like needles, flakes, and fibers, are also contemplated for inclusion herein. The terms may also include an agglomeration comprising more than one individual particle, particulate, or the like. Additionally, a particle, particulate, or any desired agglomeration thereof may be composed of more than one type of material.

The term "personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "release profile" as used herein refers to the quantity or amount of active agent (which cause a SAP to deswell or reswell) that is released into solution from the triggering agents as a function of time, that are typically illustrated as the cumulative release, expressed as a percentage of the total amount of active agent present in the triggering agents, as a function of time and may be shown as a graphical summary of the releasing of the active agent into solution of a particular substance.

The term "reswell" is used herein to refer to the growth in size of the SAP that occurs while fluids are being absorbed by the SAP after deswell.

The term "SAP" may be used herein in place of superabsorbent polymer, superabsorbent polymer composition, and particles thereof.

The term "singular release profile" generally refers to a release profile that is represented by a concave downward curve. The initial release rate is fast but gradually becomes slower.

The term "sigmoidal release profile" refers to a release profile that is represented by a concave upward then concave downward curve. It is generally characterized by an initial lag phase, a steep intermediate release phase, and a slow final release phase.

The term "solubility product constant" is a simplified equilibrium constant (Ksp) defined for equilibrium between a solid and its respective ions in a solution. Its value indicates the degree to which a compound dissociates in water. The higher the solubility product constant, the more soluble the compound. The Ksp expression for a salt is the product of the concentrations of the ions, with each concentration raised to a power equal to the coefficient of that ion in the balanced equation for the solubility equilibrium.

The term "sports/construction absorbent articles" includes headbands, wrist bands and other aids for absorption of perspiration, absorptive windings for grips and handles of sports equipment, and towels or absorbent wipes for cleaning and drying off equipment during use.

The term "superabsorbent polymer composition" refers to a superabsorbent polymer comprising a surface additive in accordance with the present invention.

The terms "superabsorbent polymer" and "superabsorbent polymer preproduct" refer to a material that is produced by conducting all of the steps for making a superabsorbent polymer as described herein, up through drying the material, and coarse grinding in a crusher.

The term "surface crosslinking" means that the level of functional crosslinks in the vicinity of the surface of a SAP particle generally is higher than the level of functional crosslinks in the interior of the SAP particle. As used herein, "surface" describes the outer-facing boundaries of the particle. For porous SAP particles, exposed internal surfaces also are included in the definition of surface.

The term "swell" is used herein to refer to the growth in size of a SAP that occurs while fluids are being absorbed by the SAP.

The term "superabsorbent" refers to water-swellable, water-insoluble organic or inorganic materials capable, under the most favorable conditions, of absorbing at least about 10 times their weight, or at least about 15 times their weight, or at least about 25 times their weight in an aqueous solution containing 0.9 wt % sodium chloride.

The term "target zone" refers to an area of an absorbent core where the majority of a fluid insult, such as urine, menses, or bowel movement, initially contacts. In particular, for an absorbent core with one or more fluid insult points in use, the insult target zone refers to the area of the absorbent core extending a distance equal to about 10% to about 30% of the total length of the composite from each insult point in both directions. The term "perimeter region" refers to the area outside the target zone.

The term "thermoplastic" describes a material that softens when exposed to heat and which substantially returns to a non-softened condition when cooled to room temperature.

The term "triggering agent" is used herein to refer to a material that includes an active agent chemical that when released causes a SAP to deswell or to reswell as desired.

The term "% by weight" or "wt %" or variations thereof, when used herein and referring to components of a SAP, is to be interpreted as based on the weight of dry SAP, unless otherwise specified herein.

These terms may be defined with additional language in the remaining portions of the specification.

DETAILED DESCRIPTION

Absorbent articles of the present invention can comprise an absorbent composite or absorbent system. In some aspects, the absorbent composite or absorbent system can function as the absorbent core component of an absorbent article. Thus, an absorbent article of the present invention can have an absorbent core, and in some aspects can optionally include a topsheet and/or a backsheet. In some aspects, the absorbent core can be disposed between a topsheet and a backsheet. In some aspects, the absorbent core comprises an absorbent composite or absorbent system that includes the absorbent composition of the present invention. In some aspects, the absorbent composite or absorbent system functions as the absorbent article. In some aspects, the absorbent article is desirably disposable.

In some aspects, the absorbent article of the present invention comprises an absorbent composition which utilizes multifunctional materials to enhance distribution of fluids. Current commercial SAP functions to swell and absorb fluids. The absorbent article of the present invention can include SAP which swells and absorbs fluids, and which also can deswell and release fluids away from the swollen SAP, and which can further reswell and absorb fluids from an additional fluid insult.

The absorbent articles of the present invention can comprise SAP and triggering agents. The triggering agents of this invention comprise active agent chemicals which trigger superabsorbent polymers to deswell and/or reswell.

In some aspects, the SAP of this invention swells during absorption of fluids and, in some particular aspects, may be triggered to deswell and release fluid by at least one triggering agent. The free liquid released by the triggered deswelling may then be free to be distributed away from the swollen SAP where the initial insult occurred in the absorbent article. In further aspects, the deswelled SAP may be triggered to reswell and absorb fluid by a reswell triggering agent, such as fluid during a subsequent insult. The swelling-deswelling-reswelling cycle allows insult liquid to be locked up, released, and then distributed throughout an absorbent composite or absorbent system, and then be capable of reswelling on subsequent liquid insults, fully utilizing the full absorbent capabilities of an absorbent article while minimizing leakage.

In some aspects of this invention, a SAP may be triggered to deswell and reswell by a change in the solubility of the triggering agents. In one aspect, an absorbent composition may comprise a SAP having anionic functional groups, a deswell triggering agent comprising a first water-soluble chemical comprising cations X having an ionized valence of two or more, and a reswell triggering agent comprising a second water-soluble chemical comprising anions Y, wherein the cations X of the first water-soluble chemical are capable of complexing with the anions Y of the second water-soluble chemical to form a salt having a solubility product constant $Ksp < 10^{-5}$.

In some aspects of the present invention, triggering agents having a selected release profile for release of an active agent from the triggering agents, and a method for the preparation of such triggering agents, is also included. Different absorbent applications, and/or triggering agents, may require different types of release profiles such as a singular release profile or a sigmoidal release profile. In one aspect, the release profile of the triggering agents may be controlled by selecting appropriate coating polymers that are applied on the surface of the water-soluble chemicals. In another aspect, the release profile may also be controlled by adjusting the coating process for applying coating polymers.

In some aspects, the absorbent composition of the absorbent articles demonstrating swelling-deswelling-reswelling behavior and a method of controlling the timing of the swelling-deswelling-reswelling cycle are also included. An aspect of this invention is an absorbent article having an absorbent composition comprising a SAP, a deswell triggering agent having a selected release profile for releasing a first water-soluble solid chemical, and a reswell triggering agent having a release profile for releasing a second water-soluble solid chemical from the reswell triggering agent, wherein the first water-soluble chemical has higher cumulative release than the second water-soluble chemical after exposure to aqueous fluid, such as 0.9 wt % saline, and before the first water-soluble chemical is about 100% released. The timing for absorbing/releasing fluid may be controlled by selecting suitable release profiles for the deswell and reswell triggering agents, and/or by adjusting the release rates of the deswell and reswell triggering agents, and/or by altering the absorption rate of the SAP, and/or by altering the mixing ratio of the SAP, the deswell triggering agent, and the reswell triggering agent. The acronyms "$TA_D$" and "$TA_R$" may be used in place of "deswell triggering agent" and "reswell triggering agent" respectively herein.

In some aspects of this invention, SAP having improved absorption capacity efficiency and mass efficiency in the swelling-deswelling-reswelling cycle are included. Absorption capacity efficiency improvement generally refers to the increase of the swelling or reswelling capacity of an absorbent composition compared with the absorbent composition comprising a current commercial SAP. The mass efficiency improvement refers to the utilization of a lesser percentage of reswell triggering agent with respect to the SAP while achieving the same amount of deswelling liquid.

Mass efficiency improvement also refers to the utilization of a lesser percentage of reswell triggering agent with respect to SAP while achieving the same amount of reswelling capacity. The capacity efficiency improvement may be achieved by adjusting the degree of neutralization and crosslinking of SAP, and/or by altering the absorption speed of SAP, and/or by altering the mixing ratio of the SAP, the deswell triggering agent, and the reswell triggering agent. The mass efficiency improvement may also be achieved in the same manner.

Figure 3:
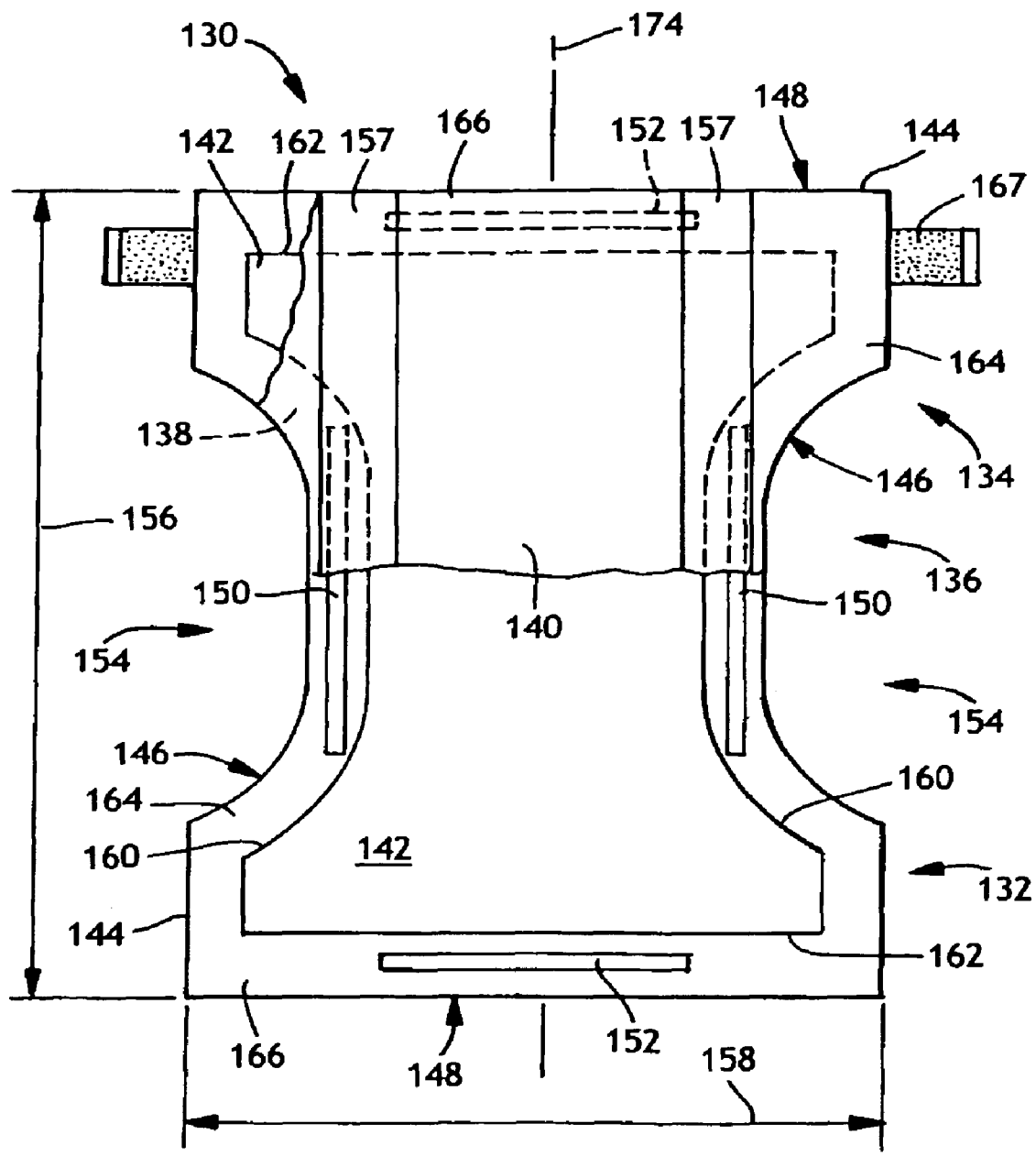
FIG. 3 is a plan view of one embodiment of an absorbent article that may be used with the present invention.

To gain a better understanding of the present invention, attention is directed to FIG. 3 for exemplary purposes showing an exemplary absorbent article of the present invention in the form of a diaper. It is understood that the present invention is suitable for use with various other absorbent articles, including but not limited to other personal care absorbent articles, health/medical absorbent articles, household/industrial absorbent articles, sports/construction absorbent articles, and the like, without departing from the scope of the present invention.

FIG. 3 illustrates a diaper 130. The diaper 130 is shown in FIG. 3 in an unfolded, flat-out, uncontracted state (i.e., with all elastic induced gathering and contraction removed). Portions of the structure are partially cut away to more clearly show the interior construction of the diaper 130, with the surface of the diaper 130 which contacts the wearer facing the viewer. FIG. 3 illustrates a disposable diaper 130 as having a front region 132, a rear region 134 and a crotch region 136 located between the front and rear regions. The diaper 130 comprises a backsheet 138, a topsheet 140, and an absorbent core 142 situated between the backsheet and the topsheet. The outer edges of the diaper 130 define a periphery 144 with transversely opposed, longitudinally extending side edges 146; longitudinally opposed, transversely extending end edges 148; and a system of elastomeric gathering members, such as a system including leg elastics 150 and waist elastics 152. The longitudinal side edges 146 define the leg dispensing orifices 154 for the diaper 130, and optionally, are curvilinear and contoured. The transverse end edges 148 are illustrated as straight, but optionally, may be curvilinear. The diaper 130 may also comprise additional components to assist in the acquisition, distribution and storage of bodily waste. For example, the diaper 130 may comprise a transport layer, such as described in U.S. Pat. No. 4,798,603, issued to Meyer et al., or a surge management layer, such as described in European Patent Application Publication No. 0 539 703, published May 5, 1993, each of which is incorporate herein by reference in a manner that is consistent herewith.

The diaper 130 generally defines a longitudinally extending length dimension 156, and a laterally extending width dimension 158. The diaper 130 may have any desired shape, such as rectangular, I-shaped, a generally hourglass shape, or a T-shape, for example.

The backsheet 138 defines a length and a width that, in the illustrated version, coincide with the length and width of the diaper 130. The absorbent core 142 generally defines a length and width that are less than the length and width of the backsheet 138, respectively. Thus, marginal portions of the diaper 130, such as marginal sections of the backsheet 138, may extend past the transversely opposed, longitudinally extending terminal side edges 160 and/or the longitudinally opposed, transversely extending terminal end edges 162 of the absorbent core 142 to form side margins 164 and end margins 166 of the diaper 130. The topsheet 140 is generally coextensive with the backsheet 138, but may optionally cover an area that is larger or smaller than the area of the backsheet, as desired. The backsheet 138 and topsheet 140 are intended to face the garment and body of the wearer, respectively, while in use. The topsheet 140 and the backsheet 138 can, for example, be joined to each other in at least a portion of the diaper periphery 144 by attachment mechanisms (not shown) such as adhesive bonds, sonic bonds, thermal bonds, pinning, stitching, or a variety of other attachment techniques known in the art, as well as combinations thereof.

The topsheet 140 suitably presents a bodyfacing surface which is compliant, soft feeling, and non-irritating to the wearer's skin. Further, the topsheet 140 may be less hydrophilic than the absorbent core 142, to present a relatively dry surface to the wearer, and is sufficiently porous to be liquid permeable, permitting liquid to penetrate readily through its thickness. A suitable topsheet 140 may be manufactured from a wide selection of web materials, such as porous foams, reticulated foams, apertured plastic films, natural fibers, synthetic fibers (for example, polyester or polypropylene fibers), or a combination of natural and synthetic fibers. The topsheet 140 is suitably employed to help isolate the wearer's skin from liquids held in the absorbent core 142.

Various woven and nonwoven fabrics may be used for the topsheet 140. For example, the topsheet 140 may be composed of a meltblown or spunbonded web of polyolefin fibers. The topsheet 140 may also be a bonded-carded web composed of natural and/or synthetic fibers. The topsheet 140 may be composed of a substantially hydrophobic material, and the hydrophobic material may, optionally, be treated with a surfactant, or otherwise processed, to impart a desired level of wettability and hydrophilicity. Specifically, the topsheet 140 may be a nonwoven, spunbond, polypropylene fabric.

The backsheet 138 may suitably be composed of a material which is either liquid permeable or liquid impermeable. It is generally desirable that the backsheet 138 be formed from a substantially liquid impermeable material. For example, a typical backsheet 138 can be manufactured from a thin plastic film or other flexible liquid impermeable material. Further, the backsheet 138 may be formed of a woven or nonwoven fibrous web layer which has been totally or partially constructed or treated to impart a desired level of liquid impermeability to selected regions that are adjacent or proximate the absorbent core 142. Still further, the backsheet 138 may optionally be composed of micro-porous "breathable" material that permits vapors to escape from the absorbent core 142 while still preventing liquid exudates from passing through the backsheet 138.

The absorbent core 142 may comprise a matrix of hydrophilic fibers, such as a web of cellulosic fluff, mixed with particles of absorbent composition, such as SAP and triggering agents of the present invention. In some aspects, the absorbent core 142 comprises a mixture of absorbent composition particles and wood pulp fluff. The wood pulp fluff may be exchanged with synthetic polymeric, meltblown fibers or with a combination of meltblown fibers and natural fibers. The absorbent composition particles may be substantially homogeneously mixed with the fibers or may be non-uniformly mixed.

As representatively illustrated in FIG. 3, the diaper 130 may include a pair of containment flaps 157 that are configured to provide a barrier to the lateral flow of body exudates. The containment flaps 157 may be located along the longitudinally extending side edges 146 of the diaper 130 adjacent the side edges of the absorbent core 142. Each containment flap 157 typically defines an unattached edge that is configured to maintain an upright, perpendicular configuration in at least the crotch region 136 of the diaper 130 to form a seal against the wearer's body. The containment flaps 157 may extend longitudinally along the entire length of the absorbent core 142 or may only extend partially along the length of the absorbent core 142. When the containment flaps 157 are shorter in length than the absorbent core 142, the containment flaps 157 can be selectively positioned anywhere along the side edges 146 of the diaper 130 in the crotch region 136. The containment flaps 157 may extend along the entire length of the absorbent core 142 to better contain the body exudates.

The diaper 130 may further include elastics at the end edges 148 and side edges 146 of the diaper 130 to further prevent leakage of body exudates and support the absorbent core 142. The diaper 130 may also include a pair of waist elastics 152 that are connected to the end edges 148 of the diaper 130. The leg elastics 150 and waist elastics 152 are generally adapted to fit about the legs and waist of a wearer in use to maintain a positive, contacting relationship with the wearer to effectively reduce or eliminate the leakage of body exudates from the diaper 130.

The elastics may be adhered to the backsheet 138 in a stretched position, or they may be attached to the backsheet 138 while the backsheet 138 is pleated, such that elastic constrictive forces are imparted to the backsheet 138. The leg elastics 150 may also include such materials as polyurethane, synthetic and natural rubber. The waist elastics 152 may be formed by elastic strands attached to the backsheet 138 or they may be formed by attaching separate pieces of stretchable materials to the waist regions of the article.

The disposable absorbent articles can, but need not necessarily, comprise fasteners 167 for securing the absorbent article about the waist of the wearer. The illustrated version of the diaper 130 comprises such fasteners 167. In at least one aspect, the fasteners 167 are situated in the rear region 134 of the diaper 130, and are located inboard each longitudinal extending side edge 146. The fasteners 167 may be configured to encircle the hips of the wearer and engage the backsheet 138 of the front region 132 of the diaper 130 for holding the diaper on the wearer. Suitable fasteners are well known to those of skill in the art and can comprise adhesive tape tab fasteners, hook and loop fasteners, mushroom fasteners, snaps, pin, belts and the like, and combinations thereof. Desirably, the fasteners 167 are releasably engageable directly with the garment-facing surface of the backsheet 138. Desirably, the fasteners 167 comprise a mechanical fastening system.

By way of illustration only, various materials and methods for constructing other absorbent articles are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference in a manner that is consistent (i.e., not in conflict) herewith.

In some aspects of the present invention, the absorbent article can comprise an absorbent composite or absorbent system of the present invention, which can function as the absorbent core 142. The absorbent composite or absorbent system can have various components, particularly the absorbent components, having corresponding configurations of structure, configurations of absorbent capacities, configurations of densities, configurations of basis weights and/or configurations of sizes which are selectively constructed and arranged to provide desired combinations of liquid intake time, absorbent saturation capacity, absorbent retention capacity, liquid distribution, shape maintenance, and aesthetics. By incorporating its various features and configurations, alone and in operative combinations, the article of the invention can provide an improved absorbent composite or absorbent system having a desired combination of swell, deswell and/or reswell capabilities. The article can be less susceptible to premature leakage, and can provide improved comfort and fit, improved protection and increased confidence to the wearer.

In some aspects, the absorbent composite or absorbent system of the present invention comprises fibers, such as fluff, or more particularly cellulosic fibers. Such cellulosic fibers may include, but are not limited to, chemical wood pulps such as sulfite and sulfate (sometimes called Kraft) pulps, as well as mechanical pulps such as ground wood, thermomechanical pulp and chemithermomechanical pulp. More particularly, the pulp fibers may include cotton, other typical wood pulps, cellulose acetate, debonded chemical wood pulp, and combinations thereof. Pulps derived from both deciduous and coniferous trees can be used. Additionally, the cellulosic fibers may include such hydrophilic materials as natural plant fibers, milkweed floss, cotton fibers, microcrystalline cellulose, microfibrillated cellulose, or any of these materials in combination with wood pulp fibers. Suitable cellulosic fluff fibers can include, for example, NB480 (available from Weyerhaeuser Co.); NB416, a bleached southern softwood Kraft pulp (available from Weyerhaeuser Co.); COOSABSORB S, a bleached southern softwood Kraft pulp (available from Bowater Inc., a business having offices located in Greenville, S.C. U.S.A.).; SULPHATATE HJ, a chemically modified hardwood pulp (available from Rayonier Inc., a business having offices located in Jesup, Ga., U.S.A.); NF 405, a chemically treated bleached southern softwood Kraft pulp (available from Weyerhaeuser Co.); and CR 1654, a mixed bleached southern softwood and hardwood Kraft pulp (available from Bowater Inc.). In some aspects, the wood pulp fluff may be exchanged with or combined with synthetic polymeric, meltblown fibers or with a combination of meltblown fibers and natural fibers.

The absorbent composite or absorbent system can be formed using methods known in the art. While not being limited to the specific method of manufacture, the absorbent composite or absorbent system can utilize a meltblown process and, in some aspects, can further be formed on a meltblown or coform line. Exemplary meltblown processes are described in various patents and publications, including NRL Report 4364, "Manufacture of Super-Fine Organic Fibers" by V. A. Wendt, E. L. Boone and C. D. Fluharty; NRL Report 5265, "An Improved Device For the Formation of Super-Fine Thermoplastic Fibers" by K. D. Lawrence, R. T. Lukas and J. A. Young; and U.S. Pat. No. 3,849,241 to Butin et al. and U.S. Pat. No. 5,350,624 to Georger et al., all of which are incorporated herein by reference in a manner that is consistent herewith.

To form "coform" materials, additional components are mixed with the meltblown fibers as the fibers are deposited onto a forming surface. For example, the absorbent composition of the present invention and fluff, such as wood pulp fibers, may be injected into the meltblown fiber stream so as to be entrapped and/or bonded to the meltblown fibers. Exemplary coform processes are described in U.S. Pat. No. 4,100,324 to Anderson et al.; U.S. Pat. No. 4,587,154 to Hotchkiss et al.; U.S. Pat. No. 4,604,313 to McFarland et al.; U.S. Pat. No. 4,655,757 to McFarland et al.; U.S. Pat. No. 4,724,114 to McFarland et al.; U.S. Pat. No. 4,100,324 to Anderson et al.; and U.K. Patent GB 2,151,272 to Minto et al., each of which is incorporated herein by reference in a manner that is consistent herewith. Absorbent, elastomeric meltblown webs containing high amounts of superabsorbent are described in U.S. Pat. No. 6,362,389 to D. J. McDowall, and absorbent, elastomeric meltblown webs containing high amounts of superabsorbent and low superabsorbent shakeout values are described in pending U.S. patent application Ser. No. 10/883,174 to X. Zhang et al., each of which is incorporated herein by reference in a manner that is consistent herewith.

Figure 4:
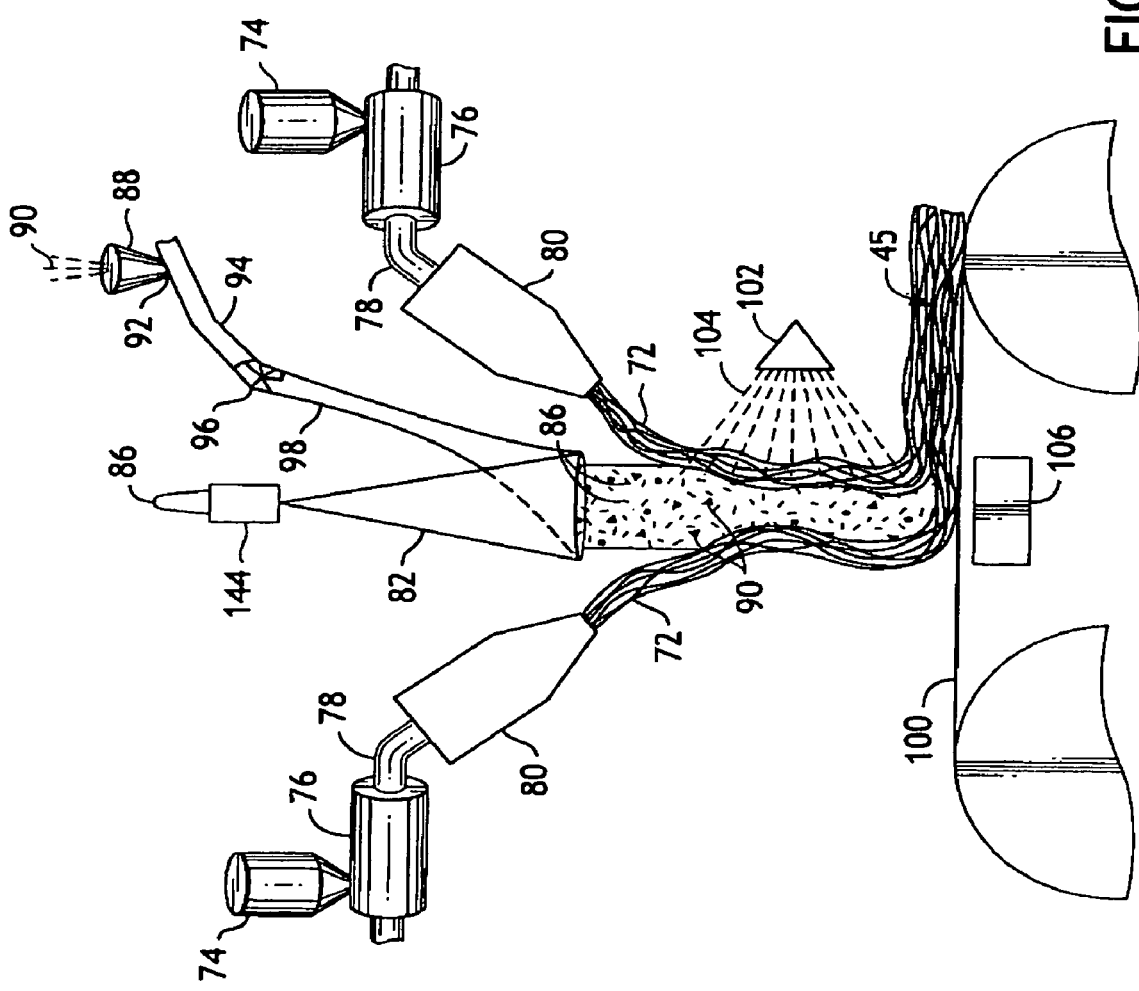
FIG. 4 is a schematic diagram of one version of a method and apparatus for producing an absorbent core.

One example of a method of forming an absorbent composite or absorbent system for use in the present invention is illustrated in FIG. 4. The dimensions of the apparatus in FIG. 4 are described herein by way of example. Other types of apparatus having different dimensions and/or different structures may also be used to form the absorbent composite or absorbent system. As shown in FIG. 4, elastomeric material 72 in the form of pellets can be fed through two pellet hoppers 74 into two single screw extruders 76 that each feed a spin pump 78. The elastomeric material 72 may be a multicomponent elastomer blend available under the trade designation VISTMAXX 2370 from ExxonMobil Chemical Company (a business having offices located in Houston, Tex., U.S.A.), as well as others mentioned herein. Each spin pump 78 feeds the elastomeric material 72 to a separate meltblown die 80. Each meltblown die 80 may have 30 holes per inch (hpi). The die angle may be adjusted anywhere between 0 and 70 degrees from horizontal, and is suitably set at about 45 degrees. The forming height may be at a maximum of about 16 inches, but this restriction may differ with different equipment.

A chute 82 having a width of about 24 inches (61 cm) wide may be positioned between the meltblown dies 80. The depth, or thickness, of the chute 82 may be adjustable in a range from about 0.5 to about 1.25 inches (1.3 cm to 3.2 cm), or from about 0.75 to about 1.0 inch (1.9 cm to 2.5 cm). A picker 144 connects to the top of the chute 82. The picker 144 is used to fiberize the pulp fibers 86. The picker 144 may be limited to processing low strength or debonded (treated) pulps, in which case the picker 144 may limit the illustrated method to a very small range of pulp types. In contrast to conventional hammermills that use hammers to impact the pulp fibers repeatedly, the picker 144 uses small teeth to tear the pulp fibers 86 apart. Suitable pulp fibers 86 for use in the method illustrated in FIG. 4 include those mentioned herein, such as NB480 (available from Weyerhaeuser Co., a business having offices located in Federal Way, Wash., U.S.A.).

At an end of the chute 82 opposite the picker 144 is a SAP feeder 88. The feeder 88 can pour the SAP 90 of the present invention into a hole 92 in a pipe 94 which then feeds into a blower fan 96. Past the blower fan 96 is a length of 4-inch (10-cm) diameter pipe 98 sufficient for developing a fully developed turbulent flow at about 5,000 feet per minute, which allows the SAP particles 90 to become distributed. The pipe 98 widens from a 4-inch (10-cm) diameter to the 24-inch by 0.75-inch (61 cm by 1.9 cm) chute 82, at which point the SAP 90 mixes with the pulp fibers 86 and the mixture falls straight down and gets mixed on either side at an approximately 45-degree angle with the elastomeric material 72. The mixture of SAP 90, pulp fibers 86, and elastomeric material 72 falls onto a wire conveyor 100 moving from about 14 to about 35 feet per minute. However, before hitting the wire conveyor 100, a spray boom 102 optionally sprays an aqueous surfactant mixture 104 in a mist through the mixture, thereby rendering the resulting absorbent composite 44 wettable. The surfactant mixture 104 may be a 1:3 mixture of GLUCOPON 220 UP (available from Cognis Corporation having a place of business in Cincinnati, Ohio, U.S.A.) and AHCOVEL Base N-62 (available from Uniqema, having a place of business in New Castle, Del., U.S.A.). An under wire vacuum 106 is positioned beneath the conveyor 100 to assist in forming an absorbent composite 44.

The absorbent composite or absorbent system of the present invention includes a desired amount of absorbent composition, such as the SAP and the triggering agents of the present invention. In some aspects, the absorbent composition has the property or capability of rapidly absorbing large amounts of fluids such as urine or other body fluids. Since the absorbent composition according to the invention has the ability to quickly lockup liquid and then gradually release this liquid so that the liquid may be distributed throughout the absorbent composite, it can result in higher utility efficiency of absorbent composites, so that they are more desirably employed in thinner articles with reduced basis weight, or highly shaped absorbent composites with narrow crotch for better fit, when compared to conventional current absorbent products. In some aspects, such absorbent composites or absorbent systems may also be suitable for use as a homogeneous absorbent composition layer without fluff or other fiber content within the diaper construction, resulting in the possibility of thinner hygiene articles.

The absorbent composition of the present invention can also be employed in absorbent articles that are suitable for further uses. In particular, the absorbent composition of this invention may be used in absorbent composites or absorbent systems for absorbent products for water or aqueous liquids, desirably in constructions for absorption of body fluids, in foamed and non-foamed sheet-like structures, in packaging materials, in constructions for plant growing, as soil improvement agents, or as active compound carriers. For this, they are processed into a web by mixing with paper or fluff or synthetic fibers or by distributing the absorbent composition particles between substrates of paper, fluff, or non-woven textiles, or by processing into carrier materials. They are further suited for use in absorbent articles such as wound dressings, packaging, agricultural absorbents, food trays and pads, and the like.

In one aspect of this invention, the SAP of the present invention is capable of swelling and absorbing fluid and, when a deswell triggering agent is applied, deswelling and releasing fluids, and when a reswell triggering agent is applied, reswelling and absorbing fluid again. "Swelling" refers to the growth in size of the SAP that occurs while fluids are being absorbed by the SAP. For swelling to occur in the SAP, fluids must be absorbed; therefore, to say that a SAP is swelling also means the SAP is absorbing fluid. "Deswelling" refers to the decrease in size of the SAP that occurs while fluids are being desorbed from the SAP. For deswelling to occur in a SAP, the absorbed fluids must be desorbed, or released from the SAP; therefore, to say a SAP is deswelling also means the SAP is releasing liquid. "Reswelling" refers to the increase in size once again of the SAP that occurs while fluids are being absorbed by the SAP after deswell. For reswelling to occur in SAP, fluids must be re-absorbed; therefore, to say that a SAP is reswelling also means the SAP is again absorbing fluid.

SAPs of this invention are capable of deswelling and desorbing fluids after interacting with triggering agent. In one aspect of this invention, a deswell triggering agent functions after the SAP is saturated, or substantially saturated, with absorbed liquid. The deswell triggering agent causes the SAP to deswell and release a desired portion of the absorbed liquid.

The SAP and the triggering agents may be present in, or on a surface of, an absorbent material in a weight ratio from about 1:0.01 to about 1:10, such as from about 1:0.1 to about 1:2. In some aspects, the resulting absorbent composite or absorbent system may include from about 10 to about 90 wt % of SAP, such as from about 20 to about 80 wt % of SAP; from about 5 to about 60 wt % of a deswell triggering agent; and from about 5 to about 60 wt % of a reswell triggering agent.

The triggering agents as described herein may be of a size that, when incorporated into a personal care product such as a baby diaper, cannot readily migrate out of the composite product. Generally, the triggering agents may have a particle size of from about 5 μm to about 1000 μm, such as from about 50 μm to about 1000 μm, or from about 100 μm to about 850 μm, or from about 150 μm to about 850 μm.

Triggering agents may be applied to the absorbent composite or absorbent system by means of blending, encapsulation, coating, attaching using a binder material, printing, laminating, strategically blending, and/or placing in specific pockets of the composites, combinations of these, or other means. Triggering agents may have time delayed effects, and only start to function (i.e., release active agents) when such effects are eliminated.

In some aspects of this invention, at least one of said triggering agents is spatially separated from the SAP and/or from the other triggering agent.

The SAP of this invention swells during absorption of fluids and, in some aspects, may be triggered to deswell and release fluid by the deswell triggering agent. The deswelled SAP can also be triggered to reswell and absorb fluid by a reswell triggering agent. In some aspects, the swelling-deswelling-reswelling cycle may be repeated multiple times.

In some aspects of the invention, certain SAPs may be more effective when used with certain triggering agents. To maximize the benefits of the present invention, it may be desirable to categorize the SAPs and the triggering agents into groupings based loosely on some characteristic, such as chemistry and/or release profile, for instance. Thus, in some aspects, the SAPs and the triggering agents may be grouped as follows: solubility chemistry and neutralization chemistry. Preferably, a SAP, a deswell triggering agent and a reswell triggering agent will all be selected from a single grouping.

The solubility-based chemistry grouping includes chemicals capable of achieving low solubility product constants (i.e., Ksp). In some aspects, the solubility-based chemistry grouping can include the following: a SAP having anionic functional groups; a deswell triggering agent comprising a first water-soluble chemical comprising cations X having an ionized valence of two or more; and a second triggering composition comprising a second water-soluble chemical comprising anions Y; where the cations X of the first water-soluble chemical are capable of complexing with the anionic functional groups of the SAP; and the anions Y of the second water-soluble chemical are capable of complexing with the cations X to form a salt having a solubility product constant $Ksp<10^{-5}$.

The neutralization-based chemistry grouping includes chemicals capable of controlling the degree of neutralization (DN) of the SAP. In some aspects, the neutralization-based chemistry grouping can include the following: a) a SAP comprising partially neutralized crosslinked poly(acrylic acid) wherein from about 40 molar percent to about 60 molar percent of the acidic functional groups are neutralized, having a pH less than about 6.0; b) a deswell triggering agent comprising a first water-soluble chemical; and c) a reswell triggering agent comprising a second water-soluble chemical having pH of about 10 or more; where when the absorbent composition is contacted with an aqueous fluid, the SAP exhibits swell-deswell-reswell behavior and the resultant swollen SAP has a pH higher than the SAP of a).

In addition, a release-based chemistry grouping can include chemicals capable of controlling the release profile of the solubility-based chemistry and/or neutralization-based chemistry groups described above. In some aspects, the release-based chemistry grouping can include the following: a SAP comprising an optional blowing agent; a deswell triggering agent comprising a first water-soluble solid chemical where the deswell triggering agent has a release profile for releasing the water-soluble solid chemical (active agent) from the triggering composition, wherein the release profile is selected from a singular release profile or a sigmoidal release profile; and a reswell triggering agent comprising a second water-soluble solid chemical where the second triggering composition has a sigmoidal release profile for releasing the second water-soluble solid chemical (active agent) from the triggering composition; and where the first water-soluble chemical has a higher cumulative release than the second water-soluble chemical after exposure to aqueous fluid and before about 100% release.

In some aspects, the SAP, the deswell triggering agent, and the reswell triggering agent of the solubility-based chemistry grouping and the neutralization-based chemistry grouping can be used on their own, or in conjuction with the chemicals of the release-based chemistry grouping to achieve the swell-deswell-reswell behavior of the present invention. However, in general, the chemicals of the release-based chemistry grouping cannot be utilized on their own to achieve the swell-deswell-reswell behavior of the present invention.

Thus, in some aspects of this invention, a SAP may be triggered to deswell and reswell by a change in the solubility of the triggering agent chemicals. In some aspects of this invention, an absorbent composition may comprise a SAP having anionic functional groups; a deswell triggering agent comprising a first water-soluble chemical comprising cations X having an ionized valence of two or more; and a reswell triggering agent comprising a second water-soluble chemical comprising anions Y, wherein the cations X of the first water-soluble chemical are capable of complexing with the anions Y of the second water-soluble chemical to form a salt having a solubility product constant $Ksp<10^{-5}$. Without intending to be bound thereby, it is hypothesized that the ion exchange reaction between the deswell triggering agent and the SAP may result in ionic crosslinking in the gel network that triggers the SAP to deswell and release the absorbed liquid. The ion exchange reaction between the reswell triggering agent and the deswelled SAP may remove at least a portion of ionic crosslinking so that the SAP can reswell and absorb additional liquid.

The first water-soluble chemical as described herein comprises cations having an ionized valence of two or more. Specific examples of the first chemical include, for example, aluminum chloride, aluminum sulfate, barium chloride, calcium acetate, calcium chloride, calcium formate, magnesium acetate, magnesium chloride, magnesium formate, zinc acetate, zinc chloride, zinc formate, and zinc sulfate.

The water-soluble chemical of the reswell triggering agent as described herein includes anions which are capable of forming an insoluble salt with the cations of the deswell triggering agent. The anions may be selected from $F^-$, $HCO_3^-$, $CO_3^{2-}$, $PO_4^{3-}$, $SO_4^{2-}$, oxalate, citrate, sulfide, and polyphosphate anions. Specific examples of this chemical include, for example, sodium fluoride, sodium hydrogen carbonate, sodium carbonate, sodium citrate, sodium oxalate, sodium phosphate, sodium polyphosphate, sodium sulfide, sodium sulfate, or sodium tripolyphosphate.

It is noted that the deswell and reswell triggering agents discussed above are suitable for anionic SAPs. However, if cationic SAPs are utilized, the deswell and reswell triggering agents themselves may be different, but the mechanism (i.e., solubility-based chemistry and neutralization-based chemistry) for selecting the triggerings agents will remain the same.

The triggering agents as described herein may further comprise a polymeric coating material for achieving controlled release of water-soluble chemicals. Specific examples of the coating material include, for example, poly(meth)acrylate copolymers, polyacrylate copolymers, ethyl cellulose, sodium carboxymethylcellulose, cellulose acetate, polyethylene glycol, maleated polypropylene, polyolefin copolymers, or combinations thereof. In certain preferred aspects, the polymeric coating used in the coatings of the present invention comprises copolymerizates of acrylic and methacrylic acid esters with a low content of quaternary ammonium groups. Such copolymerizates are often referred to as ammonio methacrylate copolymers, and are commercially available from Rohm Pharma AG, e.g., under the tradename EUDRAGIT. In certain aspects, the polymeric coating used in the coatings of the present invention comprises ethyl cellulose and/or cellulose acetate. In other aspects, the polymeric coating used in the coatings of the present invention may comprise maleated polypropylene As noted above, in some aspects of the invention, the absorbent composition may include a deswell and reswell triggering agents having a selected release profile respectively for releasing the water-soluble chemical after exposure to aqueous fluid wherein the first water-soluble chemical has higher cumulative release than the second water-soluble chemical before the first water-soluble chemical is 100% released. The release profile is selected from singular release profile or sigmoidal release profile.

In some aspects, the absorbent composition may include deswell and reswell triggering agents each having a release profile wherein from about 50 wt % to 100 wt % of the water-soluble solid chemical is released from the deswell or reswell triggering agent in less than about 240 minutes after exposure to aqueous liquid, as measured by the release profile measurement in Release Profile Test as set forth herein.

In another aspect, the absorbent composition may include a SAP comprising partially neutralized crosslinked poly(acrylic acid), having from about 40 to about 60 molar percent of the neutralized acidic functional groups, and a centrifuge retention capacity of at least about 15 grams of 0.9% by weight sodium chloride solution per gram of superabsorbent (g/g), or at least about 25 g/g, or at least about 30 g/g, or from about 25 g/g to about 60 g/g, as set forth by the Centrifuge Retention Capacity Test set forth herein.

In another aspect, the absorbent composition may include a SAP that may include from about 0.05 to about 10.0 wt % of a blowing agent. In some aspects, the blowing agent may be encapsulated by a resin that may be selected from natural or synthetic resins, acrylonitrile-butadiene rubbers, viscous settable ceramic materials, polyolefins, polyethylene gylcol, olefin copolymers, polyaromatic olefins, styrenic compounds or polymerized halo-diolefins. In other aspects, the absorbent composition may include a SAP that has a vortex time of 45 seconds or less as measured by the Vortex Test set forth herein. It has been discovered that the increase of absorption speed of the SAP described herein may improve the swelling and reswelling capacity in the swelling-deswelling-reswelling cycle.

As referenced above, in some aspects of this invention, it has been discovered that the mass efficiency and absorption capacity efficiency may be improved by the decrease of degree of neutralization and decrease of internal crosslinking of superabsorbent polymers. In another aspect of this invention, a SAP may have a degree of neutralization lower than 70% degree of neutralization. In particular the absorbent composition comprises a SAP comprising partially neutralized crosslinked poly(acrylic acid) wherein from about 40 molar percent to about 60 molar percent of the acidic functional groups are neutralized, and having a pH less than about 6.0, a deswell triggering agent that includes a first water-soluble chemical, and a reswell triggering agent having a pH of about 10 or more wherein the absorbent composition exhibits a swell-deswell-reswell behavior and the resultant swollen SAP has a pH higher than the original SAP. In some aspects, the SAPs as described herein can be made more sensitive to the triggering agents, for example, when the deswell triggering agent comprises an acid such as sulfamic acid (also known as amidosulfonic acid, amidosulfuric acid, aminosulfonic acid, and sulfamidic acid) or a water-soluble chemical having multivalent cations such as $Ca^{2+}$, and the reswell triggering agent comprises a base or a basic material such as sodium carbonate.

One advantage of this invention is that a lesser percentage of the deswell and reswell triggering agents with respect to a superabsorbent polymer composition of the present invention can be utilized to achieve the same amount of deswelling liquid and reswelling capacity as compared to a commercial superabsorbent polymer. In addition, the absorbent composition as described herein shows an increase of the swelling and reswelling capacities compared with the same absorbent composition, but comprising a commercial superabsorbent polymer instead of a superabsorbent polymer composition of the present invention.

In another aspect of this invention, the SAP and the deswell and reswell triggering agents are in particle form, and the SAP particles and the deswell and reswell triggering agent particles have a mean particle size from about 150 μm to about 850 μm as measured by screening through a U.S. standard 20 mesh screen and retained on a U.S. standard 100 mesh screen.

In another aspect of this invention, at least one of said triggering agents is spatially separated from said SAP.

In another aspect of this invention, at least one triggering agent has a profile selected from a sigmoidal release profile or a singular release profile.

As referenced above, in another aspect of this invention, the absorbent composition comprises a SAP comprising an optional blowing agent; a deswell triggering agent comprising a first water-soluble solid chemical wherein the deswell triggering agent has a release profile for releasing the water-soluble solid chemical from the triggering agent wherein the release profile is selected from a singular release profile or a sigmoidal release profile; and a reswell triggering agent comprising a second water-soluble solid chemical wherein the reswell triggering agent has a sigmoidal release profile for releasing the second water-soluble solid chemical from the triggering agent, wherein the first water-soluble chemical has higher cumulative release than the second water-soluble chemical after exposure to aqueous fluid and before about 100% release.

In another aspect of this invention, an absorbent composition comprises a SAP comprising partially neutralized crosslinked poly(acrylic acid) and having a first absorption capacity; a deswell triggering agent; and a reswell triggering agent, wherein the SAP and the deswell and reswell triggering agents are in particle form, and the SAP particles and the deswell and reswell triggering agent particles have a particle size of from more than about 150 μm to less than about 1000 μm.

In another aspect of this invention, an absorbent composition comprises a SAP; and a triggering agent comprising a water-soluble solid chemical wherein the triggering agent has a release profile for releasing the water-soluble solid chemical from the triggering agent, wherein the release profile is selected from a singular release profile or a sigmoidal release profile, wherein the SAP and the triggering agent are in particle form, and the SAP particles and the triggering agent particles have a particle size of from more than about 150 μm to less than about 1000 μm.

The water-soluble solid chemical as described herein is selected from sulfamic acid, citric acid, calcium formate, calcium chloride, calcium hydroxide, calcium oxide, calcium acetate, magnesium acetate, magnesium chloride, magnesium formate, barium chloride, aluminum chloride, aluminum sulfate, sodium aluminate, zinc chloride, zinc acetate, zinc formate, zinc sulfate, sodium fluoride, sodium hydrogen carbonate, sodium carbonate, sodium sulfate, sodium phosphate, sodium polyphosphate, sodium oxalate, sodium sulfide, or sodium tripolyphosphate.

In another aspect of this invention, an absorbent material comprises a SAP; a deswell triggering agent comprising a first water-soluble solid chemical wherein the deswell triggering agent may have a release profile for releasing the water-soluble solid chemical from the triggering agent, wherein the release profile is selected from a singular release profile or a sigmoidal release profile; and a reswell triggering agent comprising a second water-soluble solid chemical wherein the reswell triggering agent has a release profile for releasing the second water-soluble solid chemical from the triggering agent, wherein the release profile is selected from a singular release profile or a sigmoidal release profile; wherein the first water-soluble chemical has higher cumulative release than the second water-soluble chemical after exposure to aqueous fluid and before about 100% release.

An advantage of the absorbent composition of the present invention is that the timing of the swelling-deswelling-reswelling cycle may be controlled by adjusting such variables as the absorption rate of the SAP, the release rate of the deswell and reswell triggering agents, and the mixing ratio of the SAP and triggering agents.

This invention further relates to triggering agents comprising a water-soluble solid chemical; and a polymeric coating material that coats the water soluble chemical in the amount of from about 0.1 wt % to about 50 wt % of said water-soluble chemical, and wherein the triggering agent has a singular or sigmoidal release profile for releasing the water-soluble solid chemical from the triggering agent as measured by the Release Profile Measurement Test and wherein the triggering agent is in particle form, and has a particle size of less than about 1000 μm.

In another aspect of this invention, the triggering agent comprises a water-soluble solid chemical selected from sulfamic acid, citric acid, aluminum chloride, aluminum sulfate, barium chloride, calcium acetate, calcium chloride, calcium formate, magnesium acetate, magnesium chloride, magnesium formate, zinc acetate, zinc chloride, zinc formate, zinc sulfate, sodium fluoride, sodium hydrogen carbonate, sodium carbonate, sodium citrate, sodium oxalate, sodium phosphate, sodium polyphosphate, sodium sulfide, sodium sulfate, or sodium tripolyphosphate, wherein the water-soluble solid chemical is coated with a polymeric coating selected from poly(meth)acrylate copolymers, polyacrylate copolymers, maleated polypropylene, ethyl cellulose, sodium carboxymethylcellulose, cellulose acetate, polyethylene glycol, polyolefin copolymers, or a combination thereof; and wherein the triggering agent has a singular or sigmoidal release profile for releasing the water-soluble solid chemical from the triggering agent as measured by the Release Profile Measurement Test and wherein the triggering agent is in particle form, and has a particle size of from more than about 150 μm to less than about 1000 μm.

Another aspect of this invention includes a triggering agent comprising a) a water-soluble solid chemical; and b) a polymeric coating material that coats the water soluble chemical in the amount of from about 0.1 wt % to about 50 wt % of said water-soluble chemical; where the triggering agent has a release profile for releasing the water-soluble solid chemical from the triggering agent after exposure to an aqueous solution of the triggering agent, where the release profile is selected from a singular release profile or a sigmoidal release profile.

In another aspect of this invention, from about 50 wt % to 100 wt % of the water-soluble solid chemical is released from the triggering agent in less than about 240 minutes after the initial insult.

In another aspect of this invention, a triggering agent comprises a water-soluble solid chemical selected from sulfamic acid, calcium formate, sodium fluoride, sodium hydrogen carbonate, sodium carbonate, citric acid, calcium chloride, calcium hydroxide, calcium oxide, magnesium chloride, magnesium formate, barium chloride, aluminum sulfate, sodium aluminate, sodium sulfate, sodium phosphate, sodium polyphosphate, sodium oxalate, sodium sulfide, or sodium tripolyphosphate; and the water-soluble solid chemical is coated with a polymeric coating selected from poly(meth)acrylate copolymers, polyacrylate copolymers, maleated polypropylene, ethyl cellulose, sodium carboxymethylcellulose, cellulose acetate, polyethylene glycol, polyolefin copolymers, or a combination thereof. In certain aspects, the polymeric coating used in the coatings of the present invention comprises copolymerizates of acrylic and methacrylic acid esters with a low content of quaternary ammonium groups. Such copolymerizates are often referred to as ammonio methacrylate copolymers, and are commercially available from Rohm Pharma AG, e.g., under the tradename EUDRAGIT. In certain aspects of the present invention, the acrylic coating is derived from a mixture of two acrylic resin lacquers used in the form of aqueous dispersions, commercially available from Rohm Pharma under the Tradename EUDRAGIT RL 30 D and EUDRAGIT RS 30 D, respectively. EUDRAGIT RL 30 D and EUDRAGIT RS 30 D are copolymers of acrylic and methacrylic esters with a low content of quaternary ammonium groups, the molar ratio of ammonium groups to the remaining neutral (meth)acrylic esters being 1:20 in EUDRAGIT RL 30 D and 1:40 in EUDRAGIT RS 30 D. The mean molecular weight is about 150,000.

Various aspects of the present invention include a triggering agent, or a form thereof such as a deswell triggering agent or a reswell triggering agent, comprising a water-soluble solid chemical and a polymeric coating material that coats the water soluble chemical in the amount of from about 0.1 wt % to about 50 wt %, or amounts between these two limits, of said water-soluble chemical, wherein the triggering agent may have a release profile for releasing the water-soluble solid chemical from the triggering agent after an insult of an aqueous solution of the triggering agent, wherein the release profile is selected from a singular release profile or a sigmoidal release profile.

This invention further relates to triggering agents having a selected release profile for release of the active agent from the triggering agents, and to a method for the preparation of such triggering agents. In one aspect, the release profile of the triggering agents can be controlled by selecting appropriate coating polymers that are applied on the surface of the water-soluble chemicals. In another aspect, the release profile can be controlled by adjusting the coating process for applying the coating polymers.

The triggering agent(s) according to the present invention may be prepared by various methods known to those skilled in the art of preparing coated controlled release compositions. The triggering agent may be prepared continuously or discontinuously in laboratory or in a large-scale industrial manner.

An aspect of a first method to prepare triggering agent(s) may include the following steps:
a. providing the water-soluble solid chemical particles;
b. placing the water-soluble chemical into a container;
c. fluidizing the water-soluble solid chemical particles;
d. spraying a polymeric coating onto the fluidized particles; and
e. drying the coated particles, for example at about 50° C. for about 2 days.

A second method to prepare triggering agents may include the following steps:
a. stirring the water-soluble solid chemical particles in a mixer;
b. adding polymeric coating to the water-soluble solid chemical particles; and c. heating the coated particles, for example at about 50° C. for about 2 hours.

A third method to prepare triggering agents is a fluid bed process and may include the following steps:
a. preparing a coating solution of the polymeric coating, talc, and triethyl citrate;
b. fluidizing water-soluble solid chemical particles;
c. spraying the coating solution onto the water-soluble solid chemical particles; and
d. drying the coated particles, for example at about 40° C. for about 24 hours.

A stabilized product of the triggering agent may be obtained by subjecting the coated substrate to oven heating at a temperature above the glass transition temperature (Tg) of the plasticized acrylic polymer for the required time period, the optimum values for temperature and time for the particular formulation being determined experimentally.

The cured, coated compositions of the present invention provide a stable dissolution profile when stored for extended periods of time at room temperature and ambient humidity (e.g., long term (real time) testing), and when tested under accelerated storage conditions.

In some aspects, the triggering agents can be present in an absorbent composite or absorbent system as descrete particles (including other forms, such as film, flakes, fibers, nanparticles and the like). In other aspects, at least one of the triggering agents can be coated onto the SAP, such as a superabsorbent polymer particle.

In some aspects, the SAP can be a superabsorbent polymer composition of the present invention. A superabsorbent polymer composition as set forth in aspects of the present invention is obtained by the initial polymerization of from about 55% to about 99.9% by weight of the superabsorbent polymer composition of polymerizable unsaturated acid group containing monomer. A suitable monomer may include any of those containing carboxyl groups, such as acrylic acid, methacrylic acid, or 2-acrylamido-2-methylpropanesulfonic acid, or mixtures thereof. At least about 50% by weight, or at least about 75% by weight of the acid groups may be carboxyl groups.

The acid groups may be neutralized to the extent of at least about 25 mol %, that is, the acid groups may be present as sodium, potassium, or ammonium salts. In some aspects, the degree of neutralization may be at least 40 mol % or at least about 50 mol %, such as at least 60 mol %, or at least 70 mol %, or from about 40 mol % to about 60 mol %. In some aspects, it is desirable to utilize polymers obtained by polymerization of acrylic acid or methacrylic acid, the carboxyl groups of which are neutralized to the extent of from about 50 mol % to about 80 mol %, in the presence of internal crosslinking agents.

In some aspects, the suitable monomer that may be copolymerized with the ethylenically unsaturated monomer may include, but is not limited to acrylamide, methacrylamide, hydroxyethyl acrylate, dimethylaminoalkyl(meth)-acrylate, ethoxylated(meth)-acrylates, dimethylaminopropylacrylamide, or acrylamidopropyltrimethylammonium chloride. Such monomer may be present in a range of from 0% to about 40% by weight of the copolymerized monomer.

The superabsorbent polymer composition of the invention may also include internal crosslinking agents. The internal crosslinking agent has at least two ethylenically unsaturated double bonds, or one ethylenically unsaturated double bond and one functional group that is reactive toward acid groups of the polymerizable unsaturated acid group containing monomer, or several functional groups that are reactive towards acid groups may be used as the internal crosslinking component and is desirably present during the polymerization of the polymerizable unsaturated acid group containing a monomer.

Examples of internal crosslinking agents include, but are not limited to, aliphatic unsaturated amides, such as methylenebisacryl- or -methacrylamide or ethylenebisacrylamide; aliphatic esters of polyols or alkoxylated polyols with ethylenically unsaturated acids, such as di(meth)acrylates or tri(meth)acrylates of butanediol or ethylene glycol, polyglycols or trimethylolpropane; di- and triacrylate esters of trimethylolpropane which may be oxyalkylated, desirably ethoxylated, with about 1 to about 30 mol of alkylene oxide; acrylate and methacrylate esters of glycerol and pentaerythritol and of glycerol and pentaerythritol oxyethylated with desirably about 1 to about 30 mol of ethylene oxide; allyl compounds, such as allyl(meth)acrylate, alkoxylated allyl(meth)acrylate reacted with desirably about 1 to about 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid; and monomers that are capable of crosslinking, such as N-methylol compounds of unsaturated amides, such as of methacrylamide or acrylamide, and the ethers derived there from. Ionic crosslinkers such as multivalent metal salts may also be employed. Mixtures of the crosslinking agents mentioned may also be employed. The content of the internal crosslinking agents is from about 0.001% to about 5% by weight such as from about 0.2% to about 3% by weight based on the total amount of the polymerizable unsaturated acid group containing monomer.

In another aspect of the present invention, from about 0.05 to about 10 wt %, such as from about 0.2 wt % to about 5 wt %, from about 0.2 wt % to about 5 wt %, of a blowing agent (based on the total monomer solution weight) may be added to the monomer solution. The blowing agents may be added prior to, simultaneously with, or immediately after polymerization is initiated. The blowing agents are not as effective if added after the hydrogel is formed, nor are they effective when added after chopping or drying the gelled polymer. By varying the amount of the blowing agent, the release of the blowing agent may be timed to provide the most advantageous microcellular structure of the resulting hydrogel.

The blowing agents may include any carbonate or bicarbonate containing salt, or mixed salt, sodium carbonate, potassium carbonate, ammonium carbonate, magnesium carbonate, or magnesium (hydrolytic) carbonates, calcium carbonate, barium carbonate, bicarbonates and hydrates of these, azo compounds or other cations, as well as naturally occurring carbonates, such as dolomite, or mixtures thereof. Blowing agents may include carbonate salts of multivalent cations, such as $Mg^{2+}$, $Ca^{2+}$, $Zn^{2+}$, and the like. Although certain of the multivalent transition metal cations may be used, some of them, such as ferric cation, may cause color staining and may be subject to reduction-oxidation reactions or hydrolysis equilibria in water. This may lead to difficulties in quality control of the final polymeric product. Also, other multivalent cations, such as $Ni^{2+}$, $Ba^{2+}$, $Cd^{2+}$, and $Hg^{2+}$, would be unacceptable because of potential toxic or skin sensitizing effects. A preferred blowing agent is $MgCO_3$, which may also be represented by the formula $(MgCO_3)_4 \cdot Mg(OH)_2 \cdot 5H_2O$. Another preferred blowing agent is $(NH_4)_2CO_3$. The blowing agents $MgCO_3$ and $(NH_4)_2CO_3$ may also be used in mixtures.

Such blowing agents may be resin encapsulated. Encapsulation of such blowing agents provides a controllable delayed release of a gas such as carbon dioxide when dispersed in a monomer solution that is heated or polymerized in accordance with the present invention. The method for encapsulation comprises coating a particular blowing agent with a resin that may be diluted in a solvent solution. The solvent utilized may be an organic or inorganic solvent such as water depending on the nature of the coating to be applied. A second coating, generally called a sealing coating, may be applied on the encapsulated blowing agent.

Resins employed in encapsulating the blowing agent in the superabsorbent polymers composition of the present invention may include but are not limited to natural and synthetic resins, polyolefins (for example, polyethylene and polypropylene), olefin copolymers (for example, copolymers of ethylene and ethylvinylacetate), polyaromatic olefins, styrenic compounds and polymerized halo-diolefins (for example, neoprene, ethylene-propylene copolymers, polyvinyl chloride, polyvinyl alcohol, polyvinyl acetate, polyacrylic acid derivatives, polycarbonate, polyesters, poly-alpha methylstyrene and polystyrene), starch, gelatin, and cellulose. Preferred resin materials include polyols such as polyethylene glycol.

From 0 to about 95% by weight of the appropriate solvent may be added to the resin to form a solution and coated on to the blowing agent. Resin solution may be applied on the blowing agent in an amount from about 10% to about 80% by weight of the encapsulation compound, such as from about 30% to about 70% by weight of the encapsulation compound, and may be applied with any encapsulating method commonly employed in the art including, but not limited to, tumbling or spraying. The purpose of the encapsulating resin is to delay the gas release by the blowing agent in the monomer solution until a later stage of the polymerization process, allowing control of and improving the microcellular structure of the hydrogel.

The encapsulation of the blowing agent by the resinous substrate may be accomplished at room temperature, but elevated temperatures are preferred. The resinous substrate may be from about 30% to about 70% by weight of the encapsulated compound.

The superabsorbent polymer composition of the invention may also include from about 50 ppm to about 1000 ppm of a thermal initiator based on the polymerizable unsaturated acid group containing monomer. Thermal initiators may include persulfates such as sodium persulfate, potassium persulfate, and ammonium persulfate; peroxides such as hydrogen peroxide, benzoyl peroxide, t-butyl peroxide, and methyl ethyl ketone peroxide; peroxyesters such as t-butylperoxypivalate, t-amylperoxypivalate, t-amylperoxy-2-ethylhexanoate and t-butylperoxyisobutyrate; and azo compounds such as azonitrile compounds, azoamidine compounds, cyclic azoamidine compounds, azoamide compounds, alkylazo compounds, 2,2'-azobis(2-amidinopropane)dihydrochloride, and 2,2'-azobis(2-(2-imidazolin-2-yl)propane)dihydrochloride.

In some aspects, initiators may be used for initiation of the free-radical polymerization. Suitable initiators may include, but are not limited to, azo or peroxo compounds, redox systems or UV initiators, sensitizers, and/or radiation.

After polymerization, the superabsorbent polymer becomes a crosslinked hydrogel that may be prepared into superabsorbent polymer particles. The superabsorbent polymer particles may then be surface crosslinked by the addition of a surface crosslinking agent and heat-treatment. In general, surface crosslinking is a process that is believed to increase the crosslink density of the polymer matrix in the vicinity of the superabsorbent particle surface with respect to the crosslinking density of the particle interior.

In some particular aspects, desirable surface crosslinking agents include chemicals with one or more functional groups that are reactive toward pendant groups of the polymer chains, typically the acid groups. The surface crosslinking agent may be present in an amount of from about 0.001% to about 5% by weight of the dry superabsorbent polymer composition, such as from about 0.1% to about 3% by weight, or such as from about 0.1% to about 1% by weight, based on the weight of the dry superabsorbent polymer composition. Applicants have found that a heat treatment step after addition of the surface crosslinking agent is desirable.

Surface crosslinking agents are chemical compounds that may contain functional groups capable of reacting with carboxylic acid or carboxyl groups. Surface crosslinking agents may include two functional groups such as some alcohol, amine, aldehyde, and carbonate groups may be used. Crosslinker molecules having multiple different functions may also be employed, such as polyols, polyamines, polyaminoalcohols, and alkylene carbonates. Ethylene glycol, diethylene glycol, triethylene glycol, polyethylene glycol, glycerol, polyglycerol, propylene glycol, diethanolamine, triethanolamine, polypropylene glycol, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, and propylene carbonate may be used. Polyols and ethylene carbonate may be used as surface crosslinking agents.

Surface crosslinking agents may be an alkylene carbonate followed by heating to effect surface crosslinking, which may improve the surface crosslinking density and the gel strength characteristics of the superabsorbent polymer particle. More specifically, the surface crosslinking agent may be coated onto the superabsorbent polymer particulate by mixing the polymer particulate with an aqueous alcoholic solution of the alkylene carbonate surface crosslinking agent. The amount of alcohol may be determined by the solubility of the alkylene carbonate and is kept as low as possible for various reasons. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0% by weight, based on the weight of the dry superabsorbent polymer. In other aspects, the alkylene carbonate surface crosslinking agent may be dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate is distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The heat treatment, which may follow the coating treatment, may be carried out as follows. In general, the heat treatment is at a temperature of from about 100° C. to about 300° C. Lower temperatures are possible if highly reactive epoxide crosslinking agents are used. However, if alkylene carbonates are used, then the thermal treatment is suitably at a temperature of from about 150° C. to about 250° C. In this particular aspect, the treatment temperature depends on the swell time and the kind of alkylene carbonate. For example, at a temperature of about 150° C., the thermal treatment may be carried out for one hour or longer. In contrast, at a temperature of about 250° C., a few minutes (e.g., from about 0.5 minutes to about 5 minutes) are sufficient to achieve the desired surface cross-linking properties. The thermal treatment may be carried out in conventional dryers or ovens known in the art.

The superabsorbent polymer composition of the present invention may further include from 0 to about 5 wt % of a multivalent metal salt on the surface of the polymer, based on the weight of the dry superabsorbent polymer composition. The multivalent metal salt is preferably water soluble. Examples of metal cations include the cations of Al, Fe, Zr, Mg, and Zn. The metal cation may have a valence of at least +3, such as with $Al^{3+}$ being most preferred. Examples of anions in the multivalent metal salt include halides, chlorohydrates, sulfates, lactate, nitrates, and acetates. Examples of such multivalent metal salts include aluminum sulfate, and aluminum lactate. A form of aluminum sulfate is hydrated aluminum sulfate, preferably aluminum sulfate having from 12 to 14 waters of hydration. Mixtures of multivalent metal salts may be employed.

The polymer and multivalent metal salt suitably may be mixed by dry blending, or in solution such as an aqueous solution, using means well known to those skilled in the art. With dry blending, a binder may be employed in an amount which is sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin, and poly(ethylene glycol).

In some aspects, the superabsorbent polymer composition of the present invention may include up to about 5% by weight, and from about 0.001% to about 5% by weight, and from about 0.01% to about 0.5% by weight of the dry superabsorbent polymer composition of a polymeric coating, such as a thermoplastic coating, or a cationic coating, or a combination of a thermoplastic coating and a cationic coating. In some particular aspects, the polymeric coating may be a polymer that may be a solid, emulsion, suspension, colloidal, or solubilized state, or combinations thereof. Polymeric coatings suitable for this invention may include, but are not limited to, a thermoplastic coating having a thermoplastic melt temperature, wherein the polymeric coating may be applied to the particle surface coincident with, or followed by a temperature of the treated superabsorbent polymer particle at about the thermoplastic melt temperature.

Examples of thermoplastic polymers that may also be employed include, but are not limited to, polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE. A thermoplastic polymer may be functionalized to have additional benefits such as water solubility or dispersability.

Polymeric coatings of this invention may also include a cationic polymer. A cationic polymer as used herein refers to a polymer or mixture of polymers comprising a functional group, or groups, having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include, but are not limited to, the salts or partial salts of poly(vinyl amines), poly(allylamines), poly(ethylene imine), poly(amino propanol vinyl ethers), poly(acrylamidopropyl trimethyl ammonium chloride), and poly(diallyldimethyl ammonium chloride). Poly(vinyl amines) include, but are not limited to, LUPAMIN 9095 available from BASF Corporation, Mount Olive, N.J. Examples of natural-based cationic polymers include, but are not limited to, partially deacetylated chitin, chitosan, and chitosan salts. Synthetic polypeptides such as polyasparagins, polylysines, polyglutamines, and polyarginines are also suitable cationic polymers.

The superabsorbent polymer compositions according to the invention may include from 0 to about 5 wt %, or from 0.05 to about 2.0 wt %, of a multivalent metal salt, based on the dry superabsorbent polymer composition. The multivalent metal salt may be applied to the surface of the superabsorbent polymer composition. The multivalent metal salt may be water soluble. Examples of metal cations include the cations of Al, Fe, Zr, Mg, and Zn. The metal cation may have a valence of at least +3, with Al being most preferred. Examples of anions in the multivalent metal salt include halides, chlorohydrates, sulfates, lactates, nitrates and acetates, with chlorides, sulfates, chlorohydrates, and acetates being preferred, chlorohydrates and sulfates being more preferred, and sulfates being the most preferred. Aluminum sulfate is the most preferred multivalent metal salt and is readily commercially available. The multivalent metal salt may be an aluminum sulfate such as hydrated aluminum sulfate, such as aluminum sulfate having from 12 to 14 waters of hydration. The multivalent metal salt may be aluminum lactate. Mixtures of multivalent metal salts may be employed.

The superabsorbent polymer compositions according to the invention may include from about 0.01% to about 2% by weight or from about 0.01% to about 1% by weight based on the dry superabsorbent polymer composition of a water-insoluble inorganic metal compound. The water-insoluble inorganic metal compound may be applied to the surface of the superabsorbent polymer composition. The water-insoluble inorganic metal compounds may include, but are not limited to, a cation selected from aluminum, titanium, calcium, or iron and an anion selected from phosphate, borate, or chromate. Examples of water-insoluble inorganic metal compounds include aluminum phosphate and an insoluble metal borate. The insoluble metal borate may be selected from titanium borate, aluminum borate, iron borate, magnesium borate, manganese borate, or calcium borate. The chemical formula TiBO will be used herein to designate titanium borate and analogous compounds such as titanium (III) borate $TiBO_3$. In addition, the chemical formulation also designates the case when titanium (III) borate $TiBO_3$ is treated with hydrogen peroxide to obtain titanium (IV) borate. The inorganic metal compound may have a mass median particle size of less than about 2 µm, and may have a mass median particle size of less than about 1 µm.

The inorganic metal compound may be applied in the dry physical form to the surface of the superabsorbent polymer particles. For this, the superabsorbent polymer particles may be intimately mixed with the finely divided inorganic metal compound. The finely divided inorganic metal compound may be added at about room temperature to the superabsorbent polymer composition particles and mixed in until an about homogeneous mixture is present. For this purpose, mixing is effected in suitable mixers known in the art, such as fluidized bed mixers, paddle mixers, rotary drum mixers, or twin-worm mixers. The mixing of the superabsorbent polymer particles with the finely divided water-insoluble inorganic metal compound may take place before or after any surface crosslinking, for example during the application of the surface crosslinking agent.

Alternatively, a suspension of a finely divided water-insoluble inorganic metal compounds may be prepared and applied to a particulate water absorbent polymer. The suspension may be applied, for example, by spraying. Useful dispersion media for preparing the suspension include water, organic solvents such as alcohols, for example methanol, ethanol, isopropanol, ketones, for example acetone, methyl ethyl ketone, or mixtures of water with the aforementioned organic solvents. Other useful dispersion media include dispersion aids, surfactants, protective colloidals, viscosity modifiers, and other auxiliaries to assist in the preparation of the suspension. The suspension may be applied in conventional reaction mixers, or mixing and drying systems as described above at a temperature in the range from room temperature to less than the boiling point of the dispersion medium, or at about room temperature. It is appropriate to combine the application of the suspension with a surface crosslinking step by dispersing the finely divided water-insoluble metal salt in the solution of the surface crosslinking agent. Alternatively, the suspension may also be applied before or after the surface crosslinking step. The application of the slurry may be followed by a drying step.

In some aspects, the superabsorbent polymer compositions according to the invention may also include from 0% to about 5%, or in the alternative from about 0.01% to about 3%, by weight of the dry superabsorbent polymer composition of silica. Examples of silica include fumed silica, precipitated silica, silicon dioxide, silicic acid, and silicates. In some particular aspects, microscopic noncrystalline silicon dioxide may be desirable. Products include SIPERNAT 22S and AEROSIL 200 available from Degussa Corporation, Parsippany, N.J. In some aspects, the particle diameter of the inorganic powder may be 1,000 µm or smaller, such as 100 µm or smaller.

In some aspects, the superabsorbent polymer compositions may also include from 0% to about 30% by weight of the dry superabsorbent polymer composition, such as from about 0.1% to about 5% by weight, of water-soluble polymers based on the weight of the dry superabsorbent polymer composition, of partly or completely hydrolyzed polyvinyl acetate, polyvinylpyrrolidone, starch or starch derivatives, polyglycols, polyethylene oxides, polypropylene oxides, or polyacrylic acids.

In some aspects, additional surface additives may optionally be employed with the superabsorbent polymer particles, such as odor-binding substances, such as cyclodextrins, zeolites, inorganic or organic salts, and similar materials, anticaking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the superabsorbent polymer compositions of the present invention may, after a heat treatment step, be treated with water so that the superabsorbent polymer composition has water content of up to about 10% by weight of the superabsorbent polymer composition. This water may be added with one or more of the surface additives from above added to the superabsorbent polymer.

In some aspects, the superabsorbent polymer compositions according to the invention may be prepared by two methods. In some aspects, the composition may be prepared continuously or discontinuously in a large-scale industrial manner, the after-crosslinking according to the invention being carried out accordingly.

According to one method, the partially neutralized monomer, such as acrylic acid, may be converted into a gel by free-radical polymerization in aqueous solution in the presence of crosslinking agents and any further components, and the gel may be comminuted, dried, ground, and sieved off to the desired particle size. For the present invention, the size of the high-capacity superabsorbent polymer composition particles is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

The superabsorbent polymer particles of the present invention generally include particle sizes ranging from about 50 to about 1000 µm, or from about 150 to about 850 µm. The present invention may include at least about 40 wt % of the particles having a particle size from about 300 µm to about 600 µm, at least about 50 wt % of the particles having a particle size from about 300 µm to about 600 µm, or at least about 60 wt % of the particles having a particle size from about 300 µm to about 600 µm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 microns, and less than about 30% by weight of particles having a size of less than about 300 microns as measured using for example a RO-TAP Mechanical Sieve Shaker Model B available from W. S. Tyler, Inc., Mentor, Ohio.

While the form of particles may be used by way of example of the physical form of superabsorbent polymer composition, the invention is not limited to this form and is applicable to other forms such as fibers, foams, films, beads, rods, and the like, as discussed above. In some aspects, when the superabsorbent polymer composition exists as particles or in granule form, it is desirable that these particles have a size of from about 150 µm to about 850 µm based on the sieving process that is well known in the superabsorbent industry.

According to another method, inverse suspension and emulsion polymerization may also be used for preparation of the products according to the invention. According to these processes, an aqueous, partly neutralized solution of monomer, such as acrylic acid, may be dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base optionally takes place via the monomer solution or by direct introduction into the organic solvent. The water is then removed azeotropically from the mixture, and the polymer is filtered off and optionally dried. Internal crosslinking may be carried out by polymerizing-in a polyfunctional crosslinking agent dissolved in the monomer solution and/or by reaction of suitable crosslinking agents with functional groups of the polymer during the polymerization steps.

The superabsorbent polymer compositions of the present invention may have a vortex time as measured by the test procedure set forth herein, of about 45 seconds or less, or a vortex time of from about 45 seconds to about 5 seconds, or from about 40 seconds to about 10 seconds, or from about 35 seconds to about 15 seconds. In addition the superabsorbent polymer compositions may have a Centrifuge Retention Capacity (CRC) as measured by the CRC Test of from about 15 g/g to about 60 g/g, or about 20 g/g or more, or from about 20 g/g to about 60 g/g, or about 25 g/g or more, or from about 25 g/g to about 60 g/g.

The result of these methods is a superabsorbent pre-product. A superabsorbent pre-product as used herein is produced by repeating all of the steps for making the superabsorbent, up to and including drying the material, and coarse grinding in a crusher, and removing particles greater than about 850 μm and smaller than about 150 μm.

Figure 5:
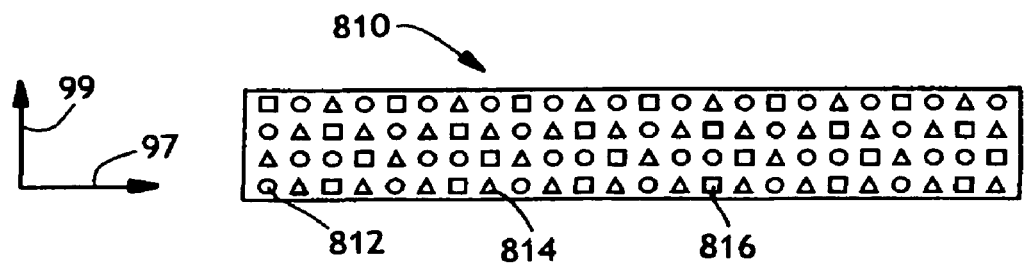
FIG. 5 is a cross-section of an absorbent composite comprising SAP and triggering agents distributed in a homogeneous fashion.

As referenced above, the absorbent composite or absorbent system of the present invention can have particular configurations of structure to provide improved benefits. For example, in some aspects, referring to FIG. 5, there is presented a cross-section view of an absorbent composite 810 having an X-direction 97 and a Z-direction 99 comprising SAP 812, a deswell triggering agent 814 and a reswell triggering agent 816 located throughout (e.g., uniformly throughout) the absorbent composite 810.

Figure 6:
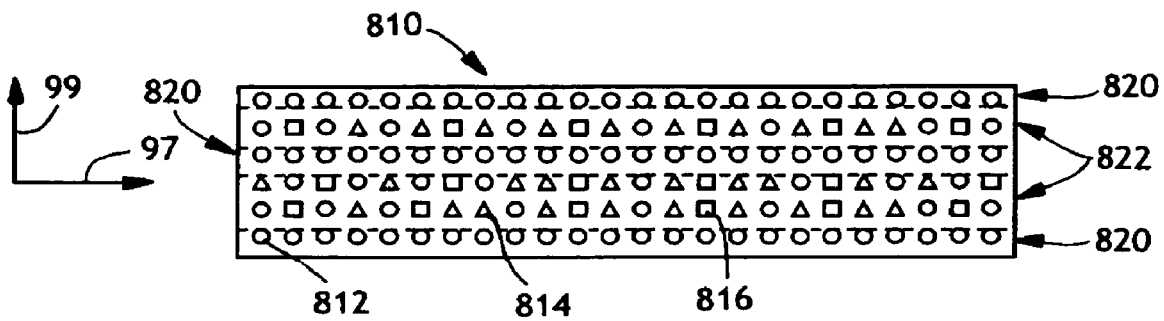
FIG. 6 is a cross-section of an absorbent composite comprising SAP and triggering agents which are arranged to have superabsorbent polymer composition rich regions and triggering agent rich regions in the z-direction.

Referring to FIG. 6, in some aspects, the absorbent composite 810 can comprise a region having predominantly SAP 812 (hereinafter referred to as a SAP-rich region) 820 and a region having predominantly deswell and/or reswell triggering agent 814,816 (hereinafter referred to as TA-rich region) 822, where the regions are configured in the Z-direction.

Figure 7:
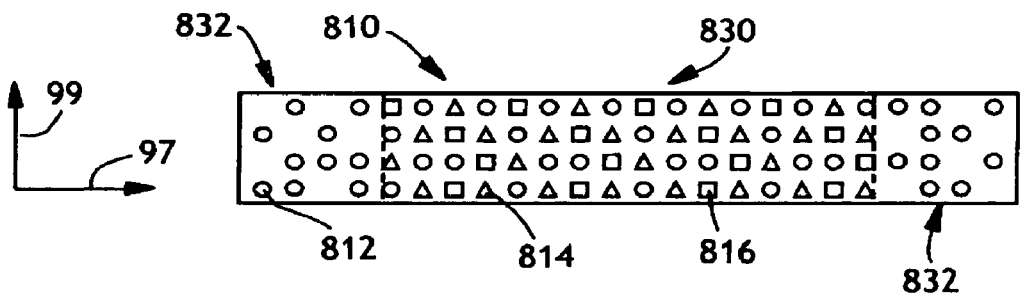
FIG. 7 is a cross-section of an absorbent composite comprising triggering agents which are preferentially located in a target zone.

Referring to FIG. 7, in some aspects, the absorbent composite 810 can comprise a target zone 830. In some aspects, the absorbent composite 810 can include SAP 812 uniformly distributed throughout the composite, with deswell and/or reswell triggering agents 814,816 respectively, located substantially only in a target zone 830 and with the perimeter region 832 comprising substantially only SAP 812.

Figure 8A:
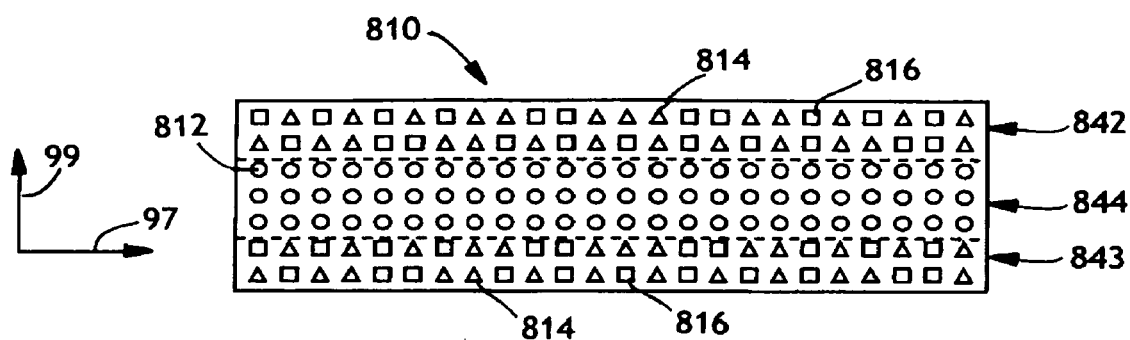
FIG. 8A is a cross-section of an absorbent system in which triggering agents are located in discrete layers.
Figure 8B:
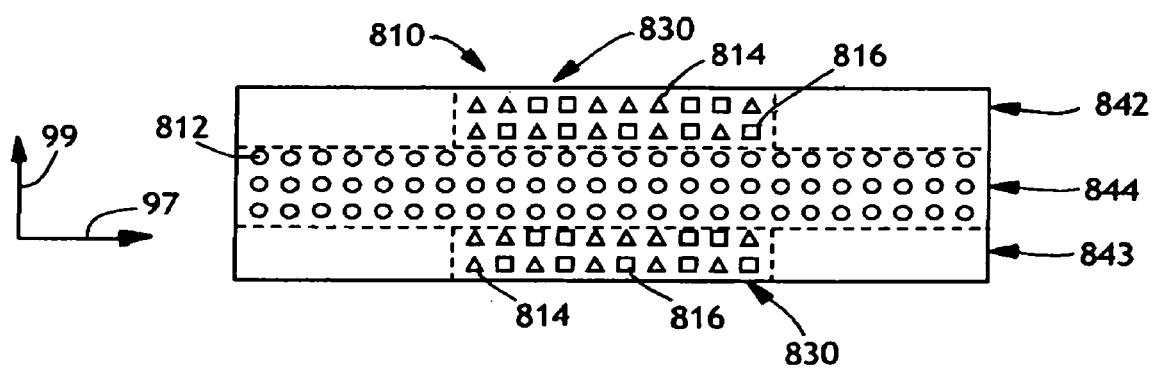
FIG. 8B is a cross-section of an absorbent system in which triggering agents are located in a target zone in the discrete layers.
Figure 8C:
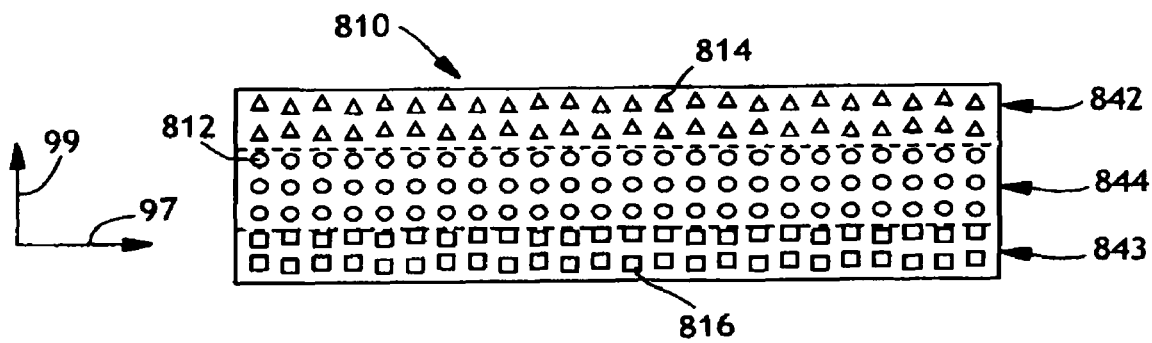
FIG. 8C is a cross-section of an absorbent system in which a deswell triggering agent is located in a discrete layer above an absorbent composite while a reswell triggering agent is located in a discrete layer below the absorbent composite.
Figure 8D:
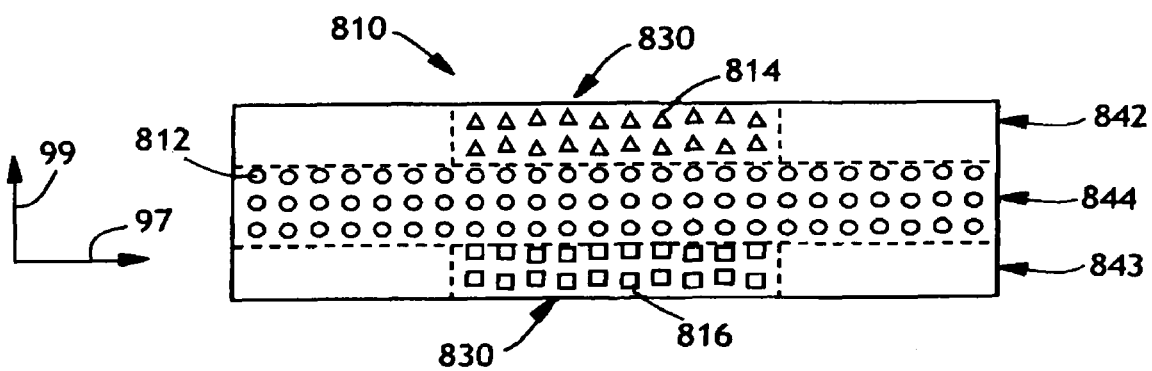
FIG. 8D is a cross-section of an absorbent system in which a deswell triggering agent is located in a target zone of a discrete layer above an absorbent composite while a reswell triggering agent is located in a target zone of a discrete layer below the absorbent composite.
Figure 8E:
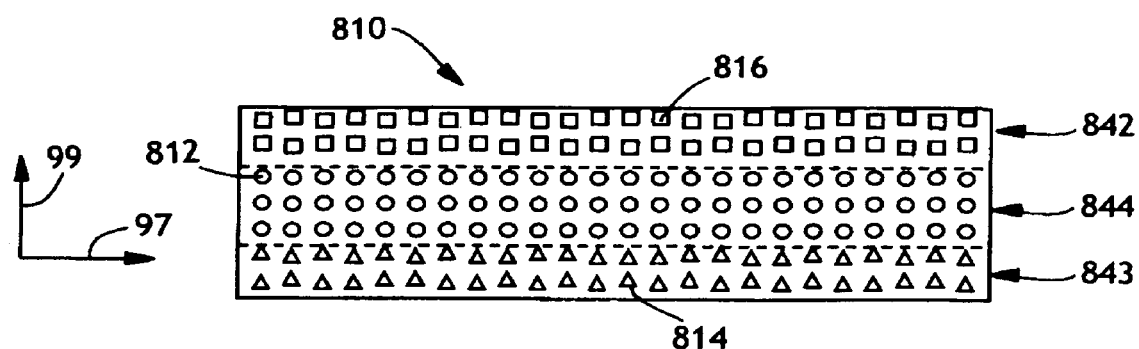
FIG. 8E is a cross-section of an absorbent system in which a reswell triggering agent is located in a discrete layer above an absorbent composite while a deswell triggering agent is located in a discrete layer below the absorbent composite.

The absorbent composition of the present invention may be comprised by an absorbent composite. Referring to FIG. 8A, in some aspects, the absorbent composite 810 can comprise SAP 812 uniformly distributed in at least a middle region 844 of the absorbent composite 810, and a deswell triggering agent 814 and/or a reswell triggering agent 816 located substantially only in at least an upper region 842 or lower region 843 of the absorbent composite 810. Referring to FIG. 8B, in further aspects, the deswell and/or reswell triggering agent 814,816 can be substantially located in a target zone 830 of at least one of an upper region 842 or lower region 843 and SAP can be located at least in a middle region 844. In particular features, the SAP and triggering agents are present in the regions 842,843,844 in uniform or variable basis weights. In other particular features, the triggering agents can be present in a target zone 830 of the regions 842,843 in uniform or variable basis weights. Referring to FIG. 8C, in further aspects, a deswell triggering agent 814 can be located substantially only in an upper region 842 of the absorbent composite 810 and/or a reswell triggering agent 816 can be located substantially only in a lower region 843 of the absorbent composite 810, and the SAP can be located at least in a middle region 844 of the absorbent composite 810. Referring to FIG. 8D, in other particular features, the triggering agents 814,816 are each present in a target zone 830 of an upper region 842 or lower region 843 and SAP is located at least in a middle region 844. Referring to FIG. 8E, in further aspects, a reswell triggering agent 816 can be located substantially only in an upper region 842 of the absorbent composite 810 and/or a deswell triggering agent 814 can be located substantially only in a lower region 843 of the absorbent composite 810, and SAP can be located at least in a middle region 844 of the absorbent composite 810.

Figure 8F:
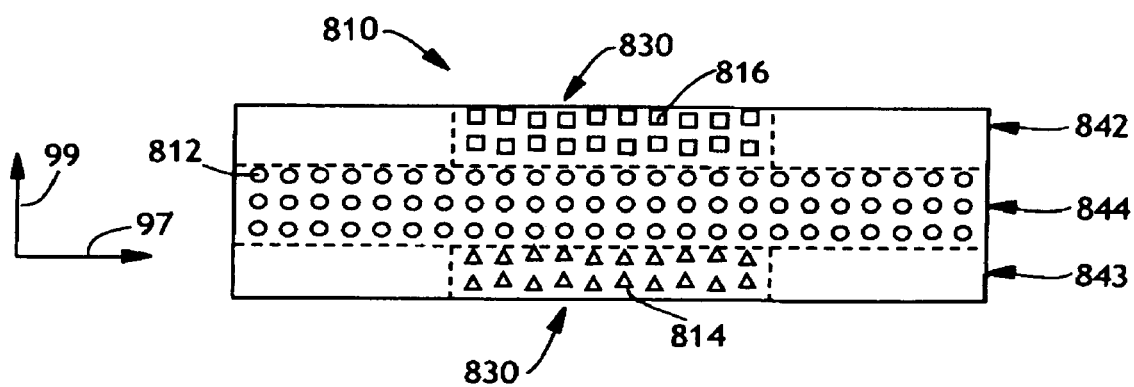
FIG. 8F is a cross-section of an absorbent system in which a reswell triggering agent is located in a target zone of a discrete layer above an absorbent composite while a deswell triggering agent is located in a target zone of a discrete layer below the absorbent composite.
Figure 8G:
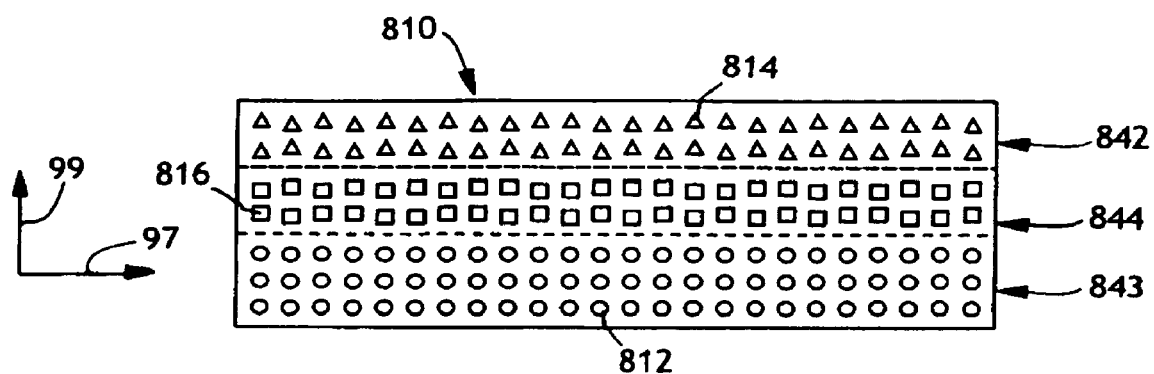
FIG. 8G is a cross-section of an absorbent system in which a reswell triggering agent is located in an absorbent composite, a deswell triggering agent is located in a discrete layer above the absorbent composite, and SAP is located in a discrete layer below the absorbent composite.
Figure 8H:
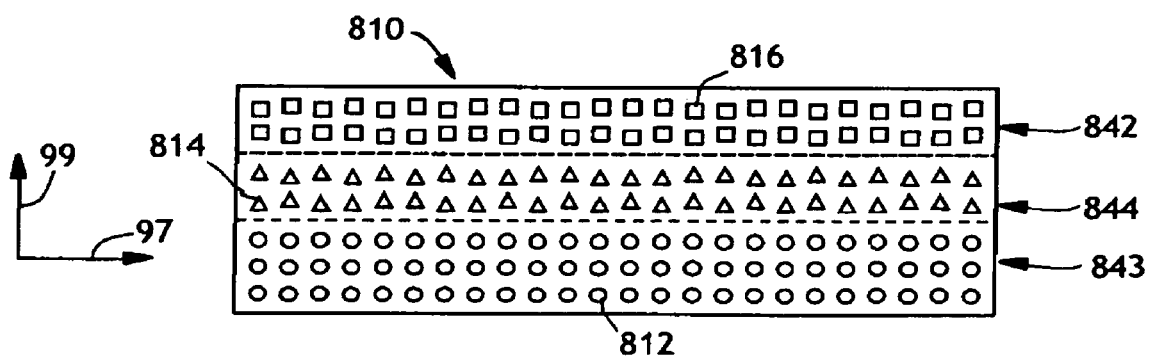
FIG. 8H is a cross-section of an absorbent system in which a deswell triggering agent is located in an absorbent composite, a reswell triggering agent is located in a discrete layer above the absorbent composite, and SAP is located in a discrete layer below the absorbent composite.
Figure 8I:
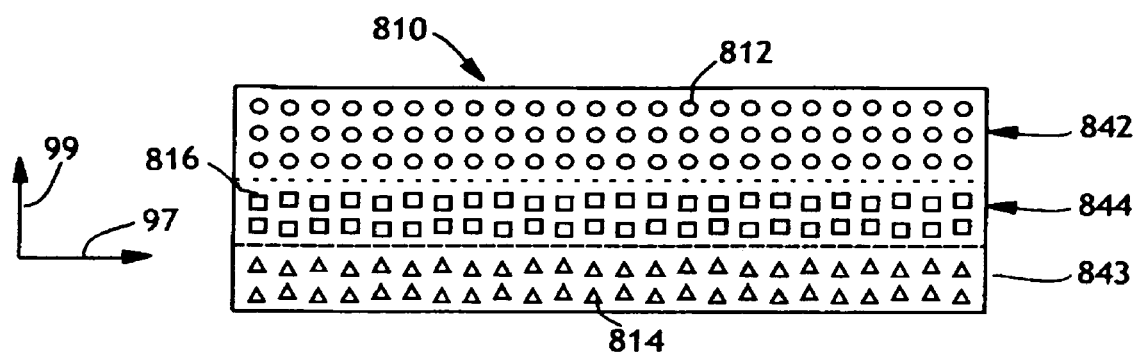
FIG. 8I is a cross-section of an absorbent system in which a reswell triggering agent is located in an absorbent composite, SAP is located in a discrete layer above the absorbent composite, and deswell triggering agent is located in a discrete layer below the absorbent composite.
Figure 8J:
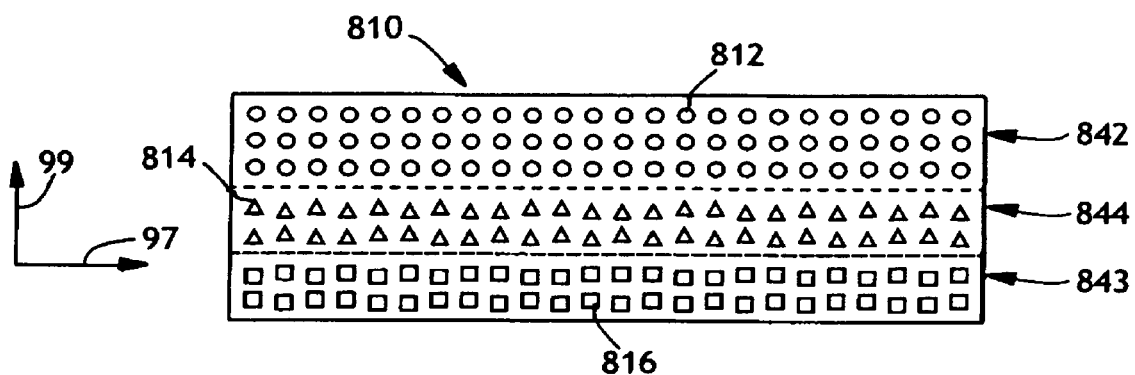
FIG. 8J is a cross-section of an absorbent system in which a deswell triggering agent is located in an absorbent composite, SAP is located in a discrete layer above the absorbent composite, and a reswell triggering agent is located in a discrete layer below the absorbent composite.

Referring to FIG. 8F, in other particular features, the triggering agents 814,816 are each present in a target zone 830 of an upper region 842 or lower region 843, with SAP located at least in a middle region 844. Referring to FIG. 8G, in other particular features, a reswell triggering agent 816 is located in the middle region 844, a deswell triggering agent 814 is located in an upper region 842, and SAP 812 is located in a lower region 843 of the absorbent composite 810. Referring to FIG. 8H, in other particular features, a deswell triggering agent 814 is located in the middle region 844, a reswell triggering agent 816 is located in the upper region 842, and SAP is located in the lower region of the absorbent composite 810. Referring to FIG. 8I, in other particular features, a reswell triggering agent 816 is located in the middle region 844, SAP 812 is located in an upper region 842, and deswell triggering agent 814 is located in a lower region 843 of the absorbent composite 810. Referring to FIG. 8J, in other particular features, a deswell triggering agent 814 is located in middle region 844, SAP 812 is located in an upper region 842, and a reswell triggering agent 716 is located in a lower region 843 of the absorbent composite 810.

The absorbent composition of the present invention may also be comprised by an absorbent system. Referring to FIG. 25A, in some aspects, the absorbent system 700 can comprise SAP 712 uniformly distributed throughout the absorbent composite layer 710, and a deswell and/or reswell triggering agent 714,716 located substantially only in at least one discrete layer 742,743 located above and/or below the absorbent composite layer 710. Referring to FIG. 25B, in further aspects, the deswell and/or reswell triggering agent 714,716 can be substantially located in a target zone 730 of at least one discrete layer 742,743. In particular features, the triggering agents are present in the discrete layers in uniform or variable basis weights. In other particular features, the triggering agents are present in a target zone 730 of the discrete layers in uniform or variable basis weights. Referring to FIG. 25C, in further aspects, a deswell triggering agent 714 can be located in a discrete layer 742 located above the absorbent composite layer 710 and/or a reswell triggering agent 716 can be located substantially in a discrete layer 743 located below the absorbent composite layer 710. Referring to FIG. 25D, in other particular features, the triggering agents are each present in a target zone 730 of a discrete layer 742,743. Referring to FIG. 25E, in further aspects, a reswell triggering agent 716 can be located in a discrete layer 742 located above the absorbent composite layer 710 and/or a deswell triggering agent 714 can be located substantially in a discrete layer 743 located below the absorbent composite layer 710.

Referring to FIG. 25F, in other particular features, the triggering agents 714,716 are each present in a target zone 730 of a discrete layer 742,743. Referring to FIG. 25G, in other particular features, a reswell triggering agent 716 is located in the absorbent composite layer 710, a deswell triggering agent 714 is located in a discrete layer 742 above the absorbent composite layer 710, and SAP 712 is located in a discrete layer 743 below the absorbent composite layer 710. Referring to FIG. 25H, in other particular features, SAP 712 is located in the absorbent composite layer 710, a deswell triggering agent 714 is located in a discrete layer 742 above the absorbent composite layer 710, and a reswell triggering agent 716 is located in an additional layer 748 located above the deswell triggering agent layer 742. Referring to FIG. 25I, in other particular features, a reswell triggering agent 716 is located in the absorbent composite layer 710, SAP 712 is located in a discrete layer 742 above the absorbent composite layer 710, and deswell triggering agent 714 is located in a discrete layer 743 below the absorbent composite layer 710. Referring to FIG. 25J, in other particular features, a SAP 712 is located in the absorbent composite layer 710, deswell triggering agent 714 is located in a discrete layer 743 below the absorbent composite layer 710, and a reswell triggering agent 716 is located in an additional layer 746 below the reswell triggering agen layer 743.

In still other aspects, the triggering agents could be located in additional layers, such as surge layers, adhesive layers, tissue layers, foam layers, adhesive/tissue laminates, and the like of the absorbent systems.

The distribution of the SAP and the triggering agents within the absorbent composite or absorbent system can be determined by several methods. For example, image analysis such as SEM, x-ray imaging can be used. Additionally, solvent extraction followed by image analysis methods. The solvent extraction should be conducted in a manner that only the triggering agent will be dissolved in the solvent media. For example, a mixture of alcohol and water can be used to limit the swelling of the SAP but at the same time dissolving the triggering agent.

It is understood that the various structural aspects presented above are provided as examples only, and that numerous additional variations are also contemplated without departing from the scope of the invention. In other particular features, the triggering agents are present in a target zone of the additional layers in desirable basis weights.

The present invention may be better understood with reference to the following examples.

EXAMPLES

The present invention may be better understood with reference to the figures and the following examples. The following examples and SAPs for the examples are provided to illustrate the invention and do not limit the scope of the claims. Unless otherwise stated, all parts and percentages are by weight.

Superabsorbent Polymer Compositions
Preproduct B

Into a polyethylene container equipped with an agitator and cooling coils was added 1167 grams of 50% NaOH and 2032 grams of distilled water and cooled to 20° C. 500 grams of glacial acrylic acid was then added to the caustic solution and the solution again cooled to 20° C. 3.75 grams of polyethylene glycol monoallylether acrylate, 3.75 grams of ethoxylated trimethylol propane triacrylate SARTOMER 454 product, and 1000 grams of glacial acrylic acid were added to the first solution, followed by cooling to 4-6° C. Nitrogen was bubbled through the monomer solution for about 10 minutes. The cooling coils were removed from the container. Immediately prior to the addition of initiators, 47 g of the coated FMC grade 50 sodium carbonate was added to the monomer solution as a blowing agent (The coated blowing agent was prepared by spraying 9 grams of polyethylene glycol 8000 solution (16.5 wt % in water) onto 300 grams of sodium carbonate powder. The coated powder was relaxed at room temperature for at least 1 hour before it was used in the polymerization batch). To the monomer solution was added 50 g of 1% by weight of $H_2O_2$ aqueous solution, 150 g of 2 wt % aqueous sodium persulfate solution, and 45 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 µm and smaller than 150 µm. The product had a CRC of 38 g/g and a vortex time of 32 seconds.

Preproduct C

Into a polyethylene container equipped with an agitator and cooling coils was added 1333 grams of 50% NaOH and 3988 grams of distilled water and cooled to 20° C. 800 grams of glacial acrylic acid was then added to the caustic solution and the solution again cooled to 20° C. 3.6 grams of polyethylene glycol monoallylether acrylate, 3.6 grams of ethoxylated trimethylol propane triacrylate SARTOMER 454 product, and 1600 grams of glacial acrylic acid were added to the first solution, followed by cooling to 4-6° C. Nitrogen was bubbled through the monomer solution for about 10 minutes. The cooling coils were removed from the container. To the monomer solution was added 80 g of 1% by weight of $H_2O_2$ aqueous solution, 120 g of 2 wt % aqueous sodium persulfate solution, and 72 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 µm and smaller than 150 µm. The product had a CRC of 36.2 g/g and a vortex time of 60 seconds.

Preproduct D

Into a polyethylene container equipped with an agitator and cooling coils was added 972 grams of 50% NaOH and 1,976 grams of distilled water and cooled to 20° C. 583 grams of glacial acrylic acid was then added to the caustic solution and the solution again cooled to 20° C. 2.625 grams of polyethylene glycol monoallylether acrylate, 2.625 grams of ethoxylated trimethylol propane triacrylate SARTOMER 454 product, and 1,167 grams of glacial acrylic acid were added to the first solution, followed by cooling to 4-6° C. Nitrogen was bubbled through the monomer solution for about 10 minutes. The cooling coils were removed from the container. Immediately prior to the addition of initiators, 51.8 g of the coated FMC grade 50 sodium carbonate was added to the monomer solution as a blowing agent (The coated blowing agent was prepared by spraying 9 grams of polyethylene glycol 8000 solution (16.5 wt % in water) onto 300 grams of sodium carbonate powder. The coated powder was relaxed at room temperature for at least 1 hour before it was used in the polymerization batch). To the monomer solution was added 50 g of 1% by weight of $H_2O_2$ aqueous solution, 150 g of 2 wt % aqueous sodium persulfate solution, and 45 g of 0.5 wt % aqueous sodium erythorbate solution to initiate polymerization reaction. The agitator was stopped and the initiated monomer was allowed to polymerize for 20 minutes. The resulting hydrogel was chopped and extruded with a Hobart 4M6 commercial extruder, followed by drying in a Procter & Schwartz Model 062 forced air oven at 175° C. for 10 minutes with up flow and 6 minutes with down flow air on a 20 in×40 in perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The product had a CRC of 34.1 g/g and a vortex time of 29 seconds.

Preproduct E

Preproduct E is produced using the method of making Preproduct C except that the amount of 50% NaOH, polyethylene glycol monoallylether acrylate, and ethoxylated trimethylol propane triacrylate was changed to 1066 grams, 2.4 grams, and 2.4 grams, respectively. The product had a CRC of 34.1 g/g and vortex time of 70 seconds.

Preproduct F

Preproduct F was produced following the same method as Preproduct D, except that the amount of polyethylene glycol monoallylether acrylate, and ethoxylated trimethylol propane triacrylate was changed 1.75 grams, and 1.75 grams, respectively. The product had a CRC of 40.1 g/g and vortex time of 26.3 seconds.

Superabsorbent Polymer Composition A (SAP-A)

SAP-A is a commercially available superabsorbent product FAVOR SXM-9300, manufactured by Evonik Stockhausen Inc., Greensboro, N.C. It has a degree of neutralization from about 65% to about 75%.

Superabsorbent Polymer Composition B (SAP-B)

Preproduct B was coated with 0.5% of SIPERNAT 22s, 1 wt % ethylene carbonate, and 3 wt % water using a 25 wt % aqueous solution. The coated Preproduct B was then heated in a convection oven at 185° C. for 45 minutes. The surface crosslinked particulate material was then post treated with 1000 ppm polyethylene glycol 8000 (polyethylene glycol with average molecular weight of 8000) and 5% water.

Superabsorbent Polymer Composition C (SAP-C)

Preproduct C was coated with 0.5% of SIPERNAT 22s, 1 wt % ethylene carbonate and 3 wt % water using a 25 wt % aqueous solution. The coated Preproduct C was then heated in a convection oven at 150° C. for 40 minutes. The surface crosslinked particulate material was then post treated with 500 ppm polyethylene glycol 8000 (polyethylene glycol with average molecular weight of 8000) and 2% water.

Superabsorbent Polymer Composition D (SAP-D)

Preproduct D was coated with 0.5% of SIPERNAT 22s, 1 wt % ethylene carbonate and 3 wt % water using a 25 wt % aqueous solution. The coated Preproduct D was then heated in a convection oven at 165° C. for 40 minutes. The surface crosslinked particulate material was then post treated with 500 ppm polyethylene glycol 8000 (polyethylene glycol with average molecular weight of 8000) and 2% water.

Superabsorbent Polymer Composition E (SAP-E)

Preproduct E was coated with 0.5% of SIPERNAT 22s, 1 wt % ethylene carbonate and 3 wt % water using a 25 wt % aqueous solution. The coated Preproduct E was then heated in a convection oven at 150° C. for 40 minutes. The surface crosslinked particulate material was then post treated with 500 ppm polyethylene glycol 8000 (polyethylene glycol with average molecular weight of 8000) and 2% water.

Superabsorbent Polymer Composition F (SAP-F)

Preproduct F was coated with 0.5% of SIPERNAT 22s, 1 wt % ethylene carbonate and 3 wt % water using a 20 wt % aqueous solution. The coated Preproduct F was then heated in a convection oven at 155° C. for 40 minutes. The surface crosslinked particulate material was then post treated with 1000 ppm polyethylene glycol 8000 (polyethylene glycol with average molecular weight of 8000) and 5% water.

The foregoing superabsorbent polymer compositions have the properties as shown in the following Table A.

TABLE A

Properties of Superabsorbent Polymer Compositions

| SAP | Centrifuge Retention Capacity (g/g) | Vortex Time (min) | Degree or neutralization (%) | pH |
|---|---|---|---|---|
| SXM9300 | 29.5 | 86 | | |
| SAP-B | 29.4 | 25 | 70 | 6.0 |
| SAP-C | 30 | 67 | 50 | 5.2 |
| SAP-D | 29.4 | 31 | 50 | 5.3 |
| SAP-E | 29.1 | 65 | 40 | 4.9 |
| SAP-F | 33 | 41 | 50 | 5.3 |

Examples of Triggering Agents

TABLE B

Triggering agents

| Triggering agent | Water-soluble chemical | Coating Polymer | Release profile |
|---|---|---|---|
| $TA_D$-A | sulfamic acid | 5% EUDRAGIT RS 30D | sigmoidal |
| $TA_D$-B | sulfamic acid | 10% EUDRAGIT RS 30D | sigmoidal |
| $TA_D$-C | Calcium Formate | 5% EUDRAGIT RS 30D | singular |
| $TA_D$-D | Calcium Formate | 10% EUDRAGIT RS 30D | singular |
| $TA_D$-E | Calcium Formate | 2.25% Cellulose Acetate | singular |
| $TA_D$-F | Calcium Formate | 3% Cellulose Acetate and 3.5% ethyl cellulose | singular |
| $TA_D$-G | Calcium Formate | 0.1% sodium carboxymethylcellulose | |
| $TA_R$-A | Sodium Carbonate | 5% EUDRAGIT RS 30D | sigmoidal |
| $TA_R$-B | Sodium Carbonate | 10% EUDRAGIT RS 30D | sigmoidal |
| $TA_R$-C | Sodium Carbonate | 18% EUDRAGIT RS 30D | sigmoidal |
| $TA_R$-D | Sodium Carbonate | 27% EUDRAGIT RS 30D | sigmoidal |
| $TA_R$-E | Sodium Carbonate | 2% Maleated propylene | singular |
| $TA_R$-F | Sodium Carbonate | 6% Maleated propylene | singular |

The abbreviations SAP-A, SAP-B, SAP-C, SAP-D, SAP-E, SAP-F, $TA_D$-A, $TA_D$-B, $TA_D$-C, $TA_D$-D, $TA_D$-E, $TA_D$-F, $TA_D$-G, $TA_R$-A, $TA_R$-B, $TA_R$-C, TC-D, $TA_R$-E, and $TA_R$-F from Tables A and B may be used in the following examples.

Example 1

Preparation of poly(meth)acrylate Coated Sulfamic Acid ($TA_D$-A and $TA_D$-B)

A polymer solution or dispersion was sprayed on the surface of water-soluble solid chemicals to form a coating layer. Well suited for this purpose are aqueous poly(meth)acrylate dispersions, for example, EUDRAGIT RS 30D, which is commercially available from Evonik Pharma Polymers.

The coating polymer dispersion was prepared according to the following formulation:

| | |
|---|---|
| EUDRAGIT RS 30D (30% aqueous dispersion) | 1200 g |
| Triethyl citrate | 36 g |
| Talc | 180 g |
| Water | 1464 g |

The mixture of coating materials was stirred in a container using an overhead stirrer. The mixture was stirred for at least 15 minutes to ensure good mixing before it was used to coat the water-soluble solid chemical.

About 800 g of sulfamic acid particles (particle size between 100-20 mesh, U.S. Sieve Series) obtained from Sigma-Aldrich Company were placed in a Glatt WSG 5 fluidized bed apparatus. The Glatt unit was set up to provide top spray by insertion of a top spray insert and a 150 micron filter bag was utilized. The air used to fluidize the sulfamic acid particles was conditioned to remove water vapor in the air. The coating material was applied at a coating material temperature of about 25° C., an atomizing air pressure of 2.0 bar, and a spray flow rate of 8 g/min/Kg. After the coating material was applied, the coated particles were dried at 40° C. for 24 hours. The coated product was produced having 5% or 10% by weight polymer coating.

The release of sulfamic acid was measured using a pH meter, as described in the Test method for the "Release Profile Measurement—Release of Coated Sulfamic Acid Test" above. The results are tabulated in Table 1 below.

TABLE 1

| Time (min) | $TA_D$ - A (5% coating) | $TA_D$ - B (10% coating) |
|---|---|---|
| 0 | 0.0 | 0.0 |
| 2 | 2.1 | 1.0 |
| 4 | 9.0 | 1.7 |
| 6 | 18.2 | 2.7 |
| 8 | 28.1 | 3.9 |
| 10 | 37.6 | 5.2 |
| 15 | 60.0 | 7.9 |
| 20 | 77.5 | 11.9 |
| 25 | 89.1 | 15.4 |
| 30 | 96.3 | 20.8 |
| 40 | 97.3 | 33.3 |
| 50 | 97.9 | 46.6 |
| 60 | 99.4 | 59.1 |
| 80 |  | 78.2 |
| 100 |  | 90.4 |

Figure 9:
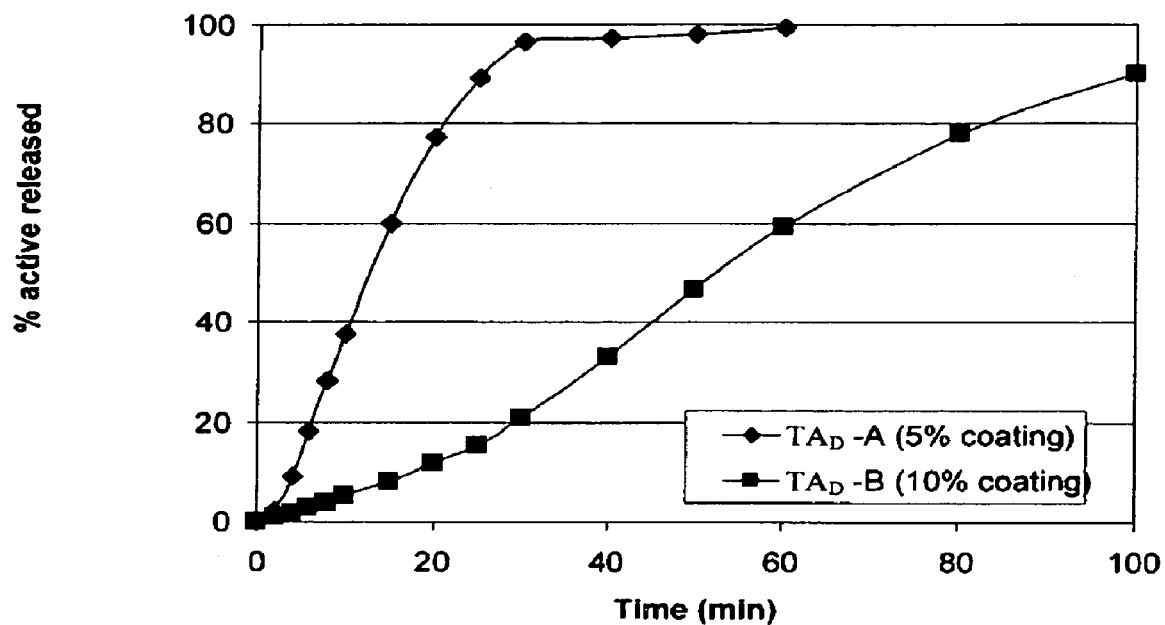
FIG. 9 is a graphical plot of release profiles of poly(meth) acrylate coated sulfamic acid.

FIG. 9 is a graphical plot of release profiles of poly(meth)acrylate coated sulfamic acid. These triggering agents showed sigmoidal release profiles. And the release rate was controlled by the amount of coating polymer.

Example 2

Preparation of poly(meth)acrylate Coated Calcium Formate ($TA_D$-C and $TA_D$-D)

The general procedures outlined in Example 1 were used to apply EUDRAGIT RS 30D polymer coating on calcium formate particles (commercially available from Fisher Scientific). The coated particles consisted 5% or 10% by weight polymer coating.

The release of calcium formate was measured according to the general procedures described in the test method, "Release of Coated Calcium Formate Test". The results are tabulated in Table 2 below.

TABLE 2

| Time (min) | $TA_D$ - C (5% coating) | $TA_D$ - D (10% coating) |
|---|---|---|
| 0 | 0.0 | 0.0 |
| 2 | 49.4 | 18.8 |
| 5 | 67.8 | 45.3 |
| 10 | 93.2 | 73.3 |
| 20 | 98.6 | 91.4 |
| 30 | 99.6 | 94.9 |
| 45 | 99.6 | 96.9 |
| 60 | 99.6 | 98.7 |

Figure 10:
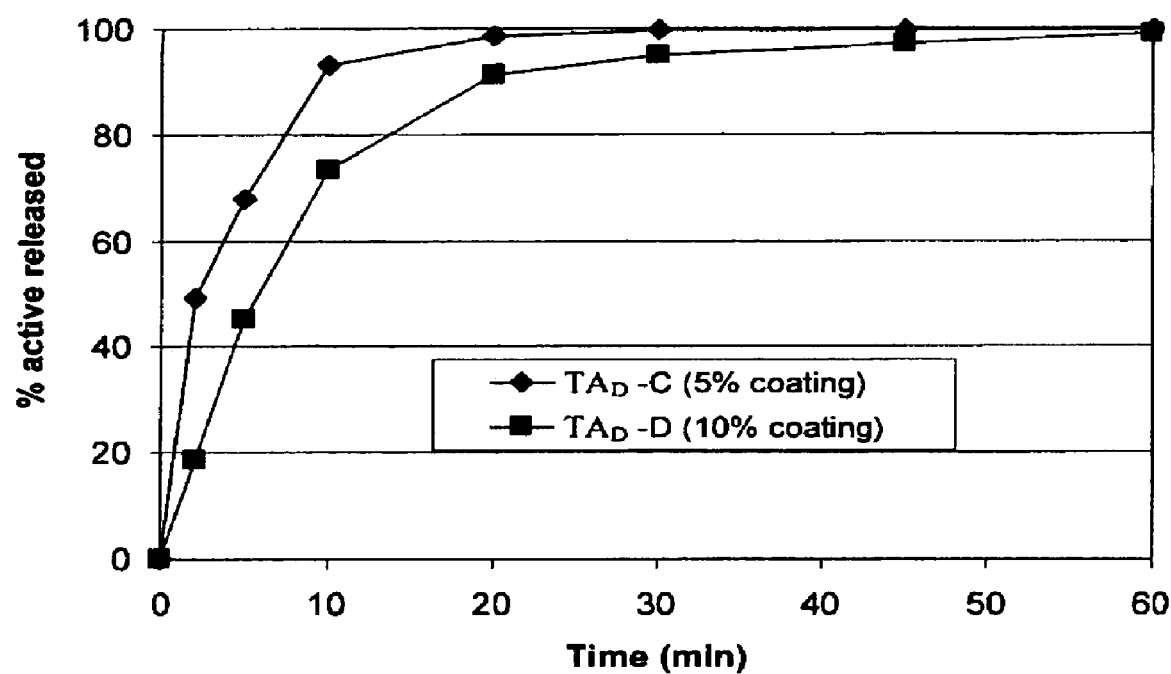
FIG. 10 is a graphical plot of release profiles of poly(meth) acrylate coated calcium formate.

FIG. 10 is a graphical plot of release profiles of poly(meth)acrylate coated calcium formate. These triggering agents showed singular release profiles. And the release rate was controlled by the amount of coating polymer.

Example 3

Calcium Formate Coated with Cellulose Acetate ($TA_D$-E)

400 g of calcium formate particles (commercially available from Fisher Scientific, particle size as shown in Table 4) were stirred in a KITCHEN-AID mixer. 45 ml of cellulose acetate solution (EASTMAN CA-398-3, 20% in acetone) was added onto the particles dropwise using a syringe over a period of two minutes. After stirring the mixture for one minute, the coated particles were air-dried then dried in oven at 50° C. for two hours. The dried material was sieved to remove particles greater than 850 μm and smaller than 150 μm. The release profile of calcium formate was measured according to the general procedure described in the test method, "Release of Coated Calcium Formate Test". The results are tabulated in Table 3 below.

Example 4

Calcium Formate Coated with Cellulose Acetate and Ethyl Cellulose ($TA_D$-F)

400 g of calcium form ate particles (commercially available from Fisher Scientific, particle size as shown in Table 4) were stirred in a KITCHEN-AID mixer. 60 ml of cellulose acetate solution (EASTMAN CA-398-3, 20% in acetone) was added onto the particles dropwise using a syringe over a period of two minutes. After stirring the mixture for one minute, the coated particles were air-dried. Then the particles were coated with 70 ml of ethyl cellulose solution (commercially available from Sigma-Aldrich, 10 cP, 20% in ethanol) in the same manner to give a second layer of coating. Then the sample was dried in oven at 50° C. for two hours. The dried material was sieved to remove particles greater than 850 μm and smaller than 150 μm. The release profile of calcium formate was measured according to the general procedure described in the test method, "Release of Coated Calcium Formate Test". The results are tabulated in Table 3 below.

TABLE 3

| Time (min) | $TA_D$ - E | $TA_D$ - F |
|---|---|---|
| 0 | 0.0 | 0.0 |
| 2 | 60.8 | 7.3 |
| 5 | 92.1 | 12.6 |
| 10 | 98.1 | 22.5 |
| 15 | 99.2 | 30.5 |
| 20 | 99.3 | 37.1 |
| 30 | 99.3 | 51.3 |

TABLE 3-continued

| Time (min) | $TA_D$ - E | $TA_D$ - F |
|---|---|---|
| 45 | 99.9 | 60.7 |
| 60 | 99.4 | 64.0 |
| 120 | 99.2 | 71.1 |

Figure 11:
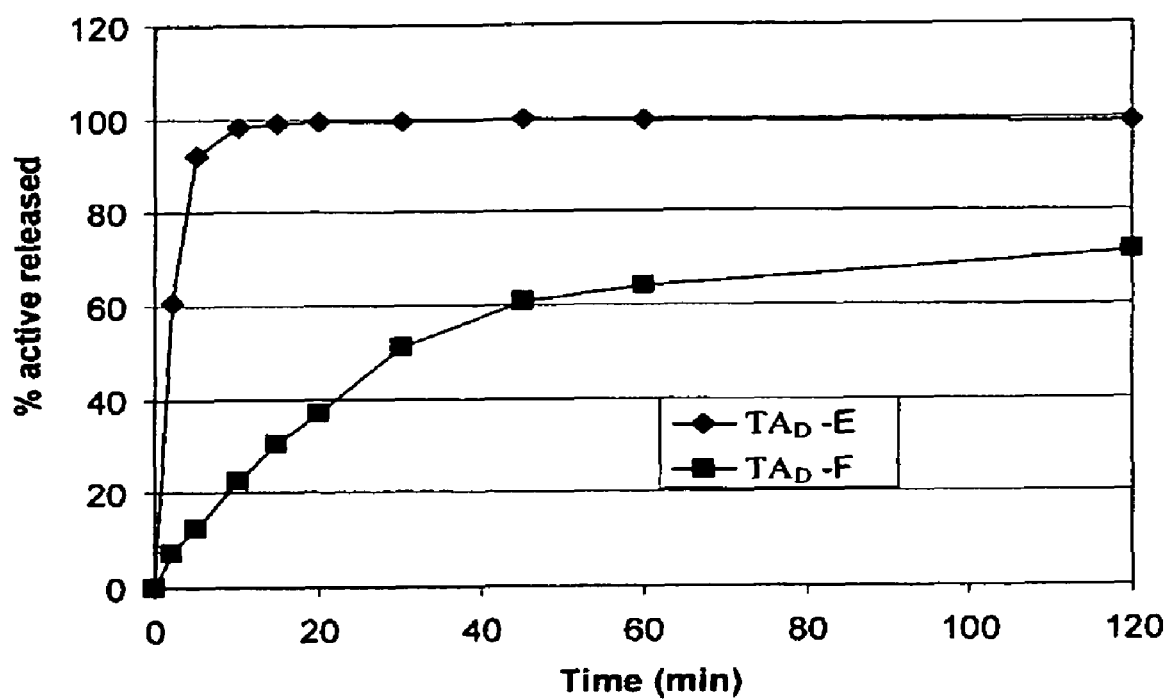
FIG. 11 is a graphical plot of release profiles of cellulose acetate or cellulose acetate/ethyl cellulose coated calcium formate.

FIG. 11 is a graphical plot of release profiles of cellulose acetate or cellulose acetate/ethyl cellulose coated calcium formate. These triggering agents showed singular release profiles.

Example 5

Preparation of Sodium Carboxymethyl Cellulose Coated Calcium Formate ($TA_D$-G)

400 g of calcium formate particles (commercially available from Fisher Scientific, particles size as shown in Table 4) were stirred in a KITCHEN-AID mixer. 40 ml of sodium carboxymethyl cellulose (CMC) solution (1% in water) was added onto the particles dropwise using a syringe over a period of one minute. After stirring the mixture for one additional minute, the coated particles were dried in oven at 110° C. for 30 minutes. Then the sample was sieved using 20/80 mesh sieves (U.S. Sieve Series). The particles on the 80 mesh sieve were collected to afford 320 grams of product. The coated particles showed fast release rate in water, 77% released at one minute, 100% released at 2 minutes. The coated sample had larger particle size than the uncoated sample, as shown in Table 4 below.

TABLE 4

Particle size distribution of CMC coated calcium formate ($TA_D$ - G)

| Sample | 850-300 microns (%) | 300-180 microns (%) | <180 microns (%) |
|---|---|---|---|
| Commercial calcium formate | 8 | 32 | 60 |
| $TA_D$ - G (CMC coated calcium formate) | 77.4 | 22.5 | 0.1 |

Example 6

Preparation of poly(meth)acrylate Coated Sodium Carbonate ($TA_R$-A to $TA_R$-D)

The general procedures outlined in Example 1 were used to apply EUDRAGIT RS 30D polymer coating on sodium carbonate particles (commercially available from Sigmal-Aldrich, particle size between 100-20 mesh, U.S. Sieve Series). The coated particles consisted 5%, 10%, 18%, or 27% by weight polymer coating.

The release of sodium carbonate was measured according to the general procedures described in the test method, "Release of Coated Sodium Carbonate". The results are tabulated in Table 5 below.

TABLE 5

| Time (min) | $TA_R$ - A (5% coating) | $TA_R$ - B (10% coating) | $TA_R$ - C (18% coating) | $TA_R$ - D (27% coating) |
|---|---|---|---|---|
| 0 | 0.0 | 0.0 | 0.0 | 0.0 |
| 2 | 3.6 | 0.3 | 0.4 | 0.2 |
| 4 | 9.5 | 0.6 | 0.5 | 0.3 |
| 6 | 15.7 | 1.1 | 0.7 | 0.4 |
| 8 | 22.1 | 1.8 | 0.8 | 0.4 |
| 10 | 28.4 | 3.6 | 1.0 | 0.5 |
| 15 | 43.5 | 10.4 | 1.5 | 0.8 |
| 20 | 56.5 | 17.3 | 3.9 | 1.0 |
| 25 | 66.8 | 25.0 | 8.1 | 1.4 |
| 30 | 75.2 | 32.3 | 12.9 | 2.1 |
| 40 | 86.1 | 47.5 | 22.6 | 5.9 |
| 50 | 91.9 | 60.6 | 32.6 | 12.7 |
| 60 | 95.0 | 71.6 | 42.5 | 20.2 |
| 80 | 99.0 | 86.0 | 61.3 | 35.6 |
| 100 | | 92.4 | 76.3 | 49.4 |
| 120 | | 96.1 | 84.7 | 60.0 |
| 150 | | | 89.9 | 72.9 |
| 210 | | | 98.9 | 94.8 |
| 280 | | | | 99.8 |

Figure 12:
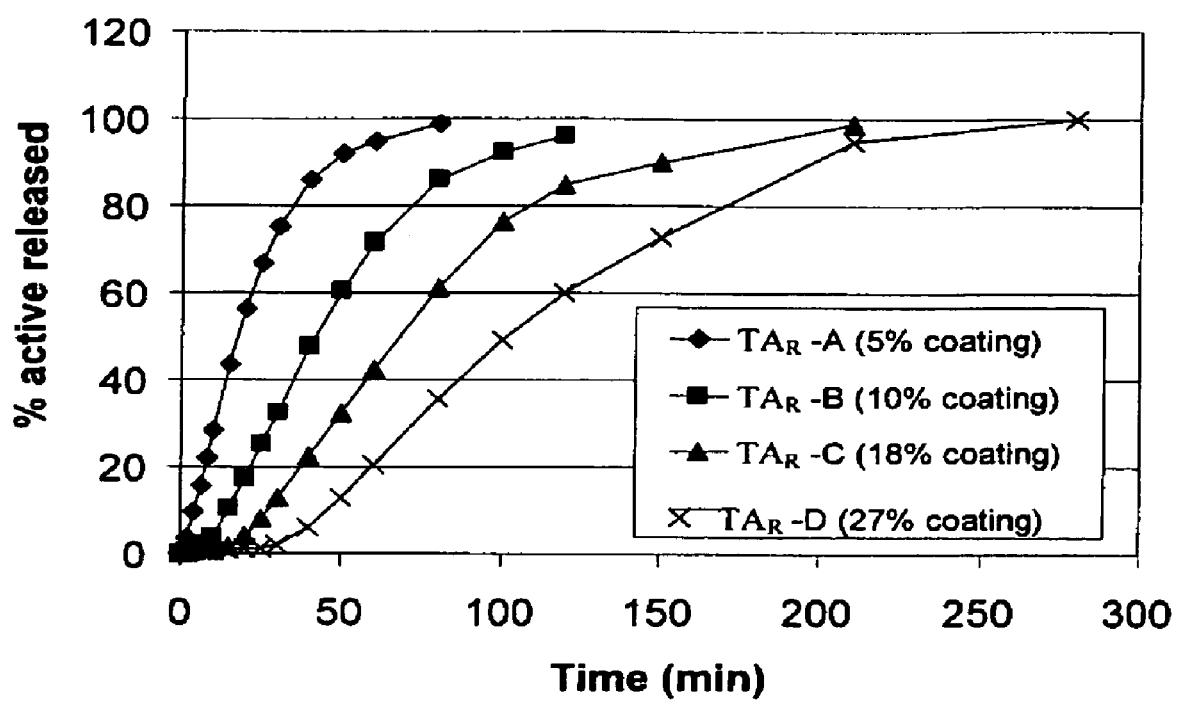
FIG. 12 is a graphical plot of release profiles of poly(meth) acrylate coated sodium carbonate.

FIG. 12 is a graphical plot of release profiles of poly(meth)acrylate coated sodium carbonate. These triggering agents showed sigmoidal release profiles.

Example 7

Preparation of MPP Coated Sodium Carbonate ($TA_R$-E, $TA_R$-F)

400 g of sodium carbonate particles (100-20 mesh) was put in a one-gallon plastic bucket. The bucket was placed on a Retch Shaker to fluidize the particles. Maleated polypropylene (MPP) emulsion (20% in water, commercially available from Chemcor, Chester, N.Y.) was sprayed onto particles using a spraying gun over a period of 20 minutes. The coated particles were dried in oven at 50° C. for 2 days. The coated particles consisted of 2% or 6% by weight of polymer coating.

The release of sodium carbonate was measured according to the general procedures described in the test method, "Release of Coated Sodium Carbonate". The results are tabulated in Table 6 below.

TABLE 6

| Time | $TA_R$ - E (2% coating) | $TA_R$ - F (6% coating) |
|---|---|---|
| 0 | 0.0 | 0.0 |
| 2 | 20.2 | 17.7 |
| 5 | 42.1 | 26.9 |
| 10 | 69.5 | 48.6 |
| 15 | 87.8 | 61.4 |
| 20 | 95.7 | 81.1 |
| 30 | 99.1 | 94.1 |
| 40 | 99.6 | 96.2 |
| 60 | 100.0 | 96.2 |

Figure 13:
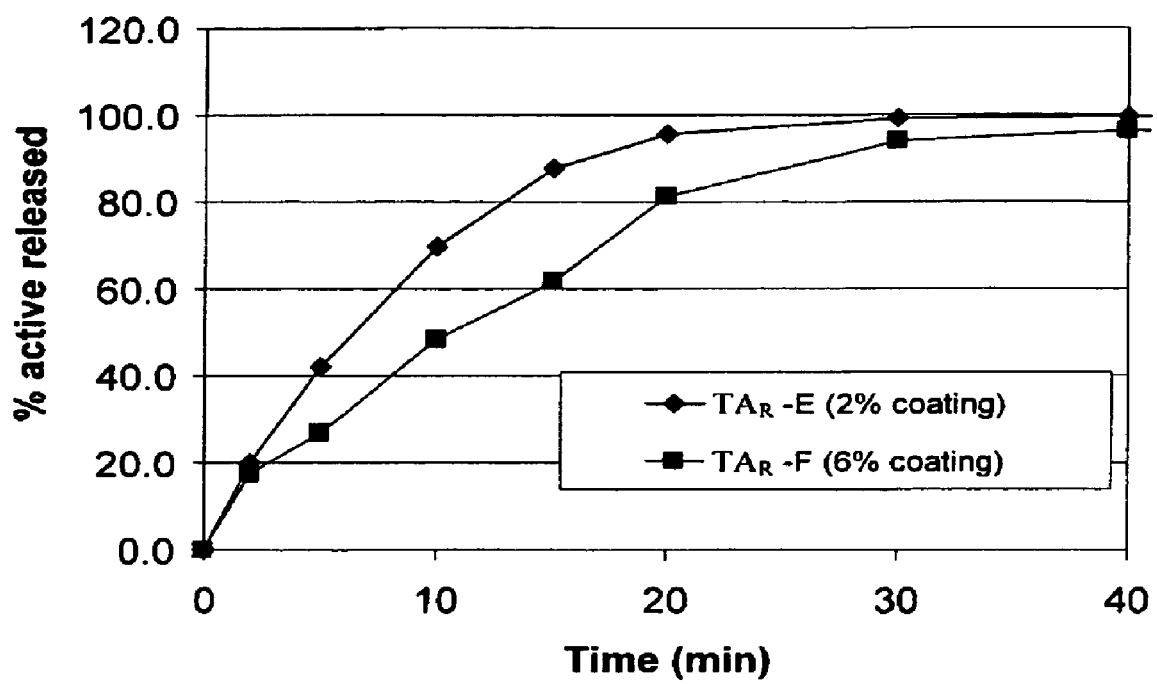
FIG. 13 is a graphical plot of release profiles of maleated polypropylene coated sodium carbonate.

FIG. 13 is a graphical plot of release profiles of maleated polypropylene coated sodium carbonate. These triggering agents showed singular release profiles.

Examples 8-13

SAP Swelling/Deswelling by Forming Insoluble Salts

FAVOR SXM-9300, a commercially available SAP manufactured by Evonik Stockhausen Inc., Greensboro, N.C., was used to demonstrate the swelling and deswelling triggered by formation of insoluble salts. The SAP was first exposed to a salt solution containing multivalent cations. Then it was exposed to a second salt solution containing anions which is able to complex with the multivalent cations of the first salt to form an insoluble salt having solubility product constant $Ksp<10^{-5}$. In comparative example 13, KCl was used as the deswell triggering agent and $Na_2SO_4$ as the reswell triggering agent.

Specifically, 0.20 g of superabsorbent polymer composition was placed in a teabag. The first centrifuge retention capacity of the SAP sample was tested according to the Centrifuge Retention Capacity Test. Then the teabag was immersed in a deswell solution which was prepared by dissolving specific amount of the deswell triggering agent in 10 g of 0.9% by weight sodium chloride solution. After 10 minutes of soaking time, the bag was placed in a centrifuge and the retention capacity was measured to give the second centrifuge retention capacity. Then the bag was immersed in a reswell solution which was prepared by dissolving specific amount of the reswell triggering agent in 20 g of 0.9% by weight sodium chloride solution. After 20 minutes of soaking time, the bag was placed in a centrifuge and the retention capacity was measured to give the third centrifuge retention capacity. Results of the testing are summarized in Table 7 below. Solubility Product Constants listed in Table 7 refer to the salts formed from the cations of the first trigger chemical and the anions of the second trigger chemical. They can be obtained from an online source: http://www.csudh.edu/oliver/chemdata/data-ksp.htm.

In addition, the results also showed that the deswelled SAP could reswell in the presence of a second salt solution containing anions which are able to complex with the cations of the first salt to form an insoluble salt having solubility product constant $Ksp<10^{-5}$. In Example 13, the cation ($K^+$) of the first salt has an ionized valence of less than two and the anions ($SO_4^{2-}$) of the second salt form a soluble salt with the cations ($K^+$) of the first salt (KCl). In this case, the SAP failed to exhibit an effective deswell and reswell. Slightly reduced $2^{nd}$ and $3^{rd}$ CRC capacities are mainly due to salt poisoning effect caused by the soluble first and second salts.

Examples 14-16

SAP Swelling/Deswelling by Forming Insoluble Salts

Table 8 below lists the swell/deswell/reswell evaluation results for SAP-B, SAP-D, and SAP-F from the Centrifuge Retention Capacity Test. Superabsorbent polymers with lower degree of neutralization (SAP-D and SAP-F, 40-60%

TABLE 7

| Example | SAP | Deswell triggering agent | Reswell triggering agent | Mixing ratio of SAP/deswell agent/reswell agent | $1^{st}/2^{nd}/3^{rd}$ CRC (g/g) | Solubility Product Constant* |
|---|---|---|---|---|---|---|
| 8 | SXM9300 | $AlCl_3$ | $Na_5P_3O_{10}$ | 1/0.2/0.33 | 29.5/19.3/26.8 | $6.3 \times 10^{-19}$ |
| 9 | SXM9300 | $CaCl_2$ | $Na_2CO_3$ | 1/0.4/0.38 | 29.5/11.0/18.0 | $3.8 \times 10^{-9}$ |
| 10 | SXM9300 | $CaCl_2$ | $Na_5P_3O_{10}$ | 1/0.2/0.53 | 29.5/20.5/25.8 | $1 \times 10^{-26}$ |
| 11 | SXM9300 | $CaCl_2$ | $Na_5P_3O_{10}$ | 1/0.4/1 | 29.5/11.0/23.7 | $1 \times 10^{-26}$ |
| 12 | SXM9300 | calcium formate | $Na_2CO_3$ | 1/0.4/0.4 | 29.5/12.5/16.7 | $3.8 \times 10^{-9}$ |
| 13 | SXM9300 | KCl | $Na_2SO_4$ | 1/0.4/0.4 | 29.5/26/26 | $>10^{-5}$ |

The results from Examples 8-12 demonstrated the ability to deswell SAP by exposing the swollen SAP to a salt solution comprising cations having an ionized valence of two or more.

DN) demonstrated improved reswelling capacity compared with the SAP having regular degree of neutralization (about 70% DN).

TABLE 8

| Ex | SAP | Deswell triggering agent | Reswell triggering agent | Mixing ratio of SAP/deswell agent/reswell agent | $1^{st}/2^{nd}/3^{rd}$ CRC (g/g) | Solubility Product Constant* |
|---|---|---|---|---|---|---|
| 14 | SAP-B | calcium formate | $Na_2CO_3$ | 1/0.3/0.6 | 29.4/16.0/20.7 | $3.8 \times 10^{-9}$ |
| 15 | SAP-D | calcium formate | $Na_2CO_3$ | 1/0.3/0.6 | 29.4/16.1/22.6 | $3.8 \times 10^{-9}$ |
| 16 | SAP-F | calcium formate | $Na_2CO_3$ | 1/0.2/0.2 | 33/26.5/31.8 | $3.8 \times 10^{-9}$ |

Examples 17-21

Swelling/Deswelling of Low DN Superabsorbent Polymers

Superabsorbent polymer compositions having 40-60% of the degree of neutralization (DN) were used to demonstrate the mass efficiency and reswelling capacity improvement over the commercial available superabsorbent polymers, such as SXM-9300. Sulfamic acid was used as the deswell triggering agent and sodium carbonate was used as the reswell triggering agent. The evaluations were performed following the general procedures as described in Examples 8-13. The results are tabulated in Table 9 below.

TABLE 9

| Ex | SAP | Deswell triggering agent | Reswell triggering agent | Mixing ratio of SAP/deswell agent/reswell agent | $1^{st}/2^{nd}/3^{rd}$ CRC (g/g) |
|---|---|---|---|---|---|
| 17 | SAP-A SXM9300 | Sulfamic acid | $Na_2CO_3$ | 1/0.4/0.4 | 29.5/17.9/26.2 |
| 18 | SAP-C | Sulfamic acid | $Na_2CO_3$ | 1/0.2/0.4 | 30/21.9/31.2 |
| 19 | SAP-C | Sulfamic acid | $Na_2CO_3$ | 1/0.4/0.4 | 30/14.1/29.9 |
| 20 | SAP-E | Sulfamic acid | $Na_2CO_3$ | 1/0.2/0.4 | 29.1/18/29.5 |
| 21 | SAP-E | Sulfamic acid | $Na_2CO_3$ | 1/0.4/0.4 | 29.1/11/29.9 |

As clearly seen in Table 9, SAPs with lower degree of neutralization (SAP-C and SAP-E) showed improved reswelling capacity and mass efficiency compared with the polymer with regular degree of neutralization, such as SXM-9300.

Example 22

Absorbent compositions comprising SXM-9300 and poly(meth)acrylate coated sulfamic acid were used to demonstrate the swelling/deswelling behavior of the absorbent compositions. A mixture of SXM-9300 and coated sulfamic acid (triggering agents $TA_D$-A or $TA_D$-B) was placed in a cylinder with screen bottom and the absorption capacity was measured according to the general procedures described in the Swell/Deswell/Reswell Test of the absorbent composition. The results are tabulated in Table 10 below.

TABLE 10

| SAP | Triggering agent | Wt. ratio of SAP and triggering agent | Starting point of deswelling step (min) | Maximum swelling capacity (g/g) |
|---|---|---|---|---|
| SXM-9300 | $TA_D$-A | 1/1.6 | 11 | 26 |
| SXM-9300 | $TA_D$-A | 1/1.2 | 13.5 | 27.4 |
| SXM-9300 | $TA_D$-A | 1/0.8 | 14.6 | 29 |
| SXM-9300 | $TA_D$-B | 1/1.2 | 33 | 33.5 |

Figure 14:
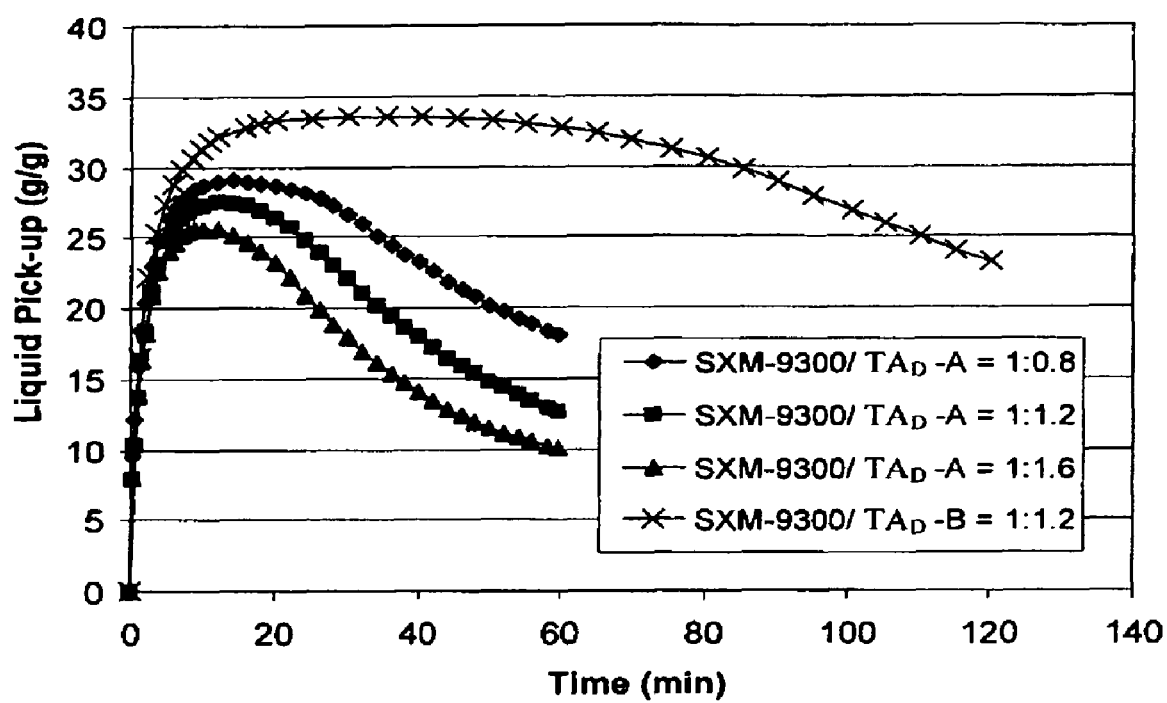
FIG. 14 is a graphical plot of swell/deswell curves for a specific SAP product with various blends of deswell triggering agents.

From the results in Table 10 and FIG. 14, it can be seen that the swelling capacity and deswelling time was controlled by the polymer coating level in the triggering agent as well as by the mixing ratio of SAP and the triggering agent.

Examples 23-27

Table 11 lists the absorbent compositions comprising a superabsorbent polymer or superabsorbent polymer composition, a deswell triggering agent comprising sulfamic acid, and a reswell triggering agent comprising a basic material such as sodium carbonate. The swell/deswell/reswell curves were measured according to the general procedures described in the Swell/Deswell/Reswell Test of the absorbent composition.

TABLE 11

Absorbent compositions having triggering agents

| Examples | SAP | Deswell triggering agent | Reswell triggering agent | Ratio |
|---|---|---|---|---|
| 23 | SXM-9300 | $TA_D$-A | $TA_R$-B | 1:1.2:1.2 |
| 24 | SXM-9300 | $TA_D$-A | $TA_R$-C | 1:1.2:1.2 |

TABLE 11-continued

Absorbent compositions having triggering agents

| Examples | SAP | Deswell triggering agent | Reswell triggering agent | Ratio |
|---|---|---|---|---|
| 25 | SAP-B | $TA_D$-A | $TA_R$-B | 1:1.2:1.2 |
| 26 | SAP-C | $TA_D$-A | $TA_R$-B | 1:0.6:1 |
| 27 | SAP-D | $TA_D$-A | $TA_R$-B | 1:0.6:1 |

Figure 15:
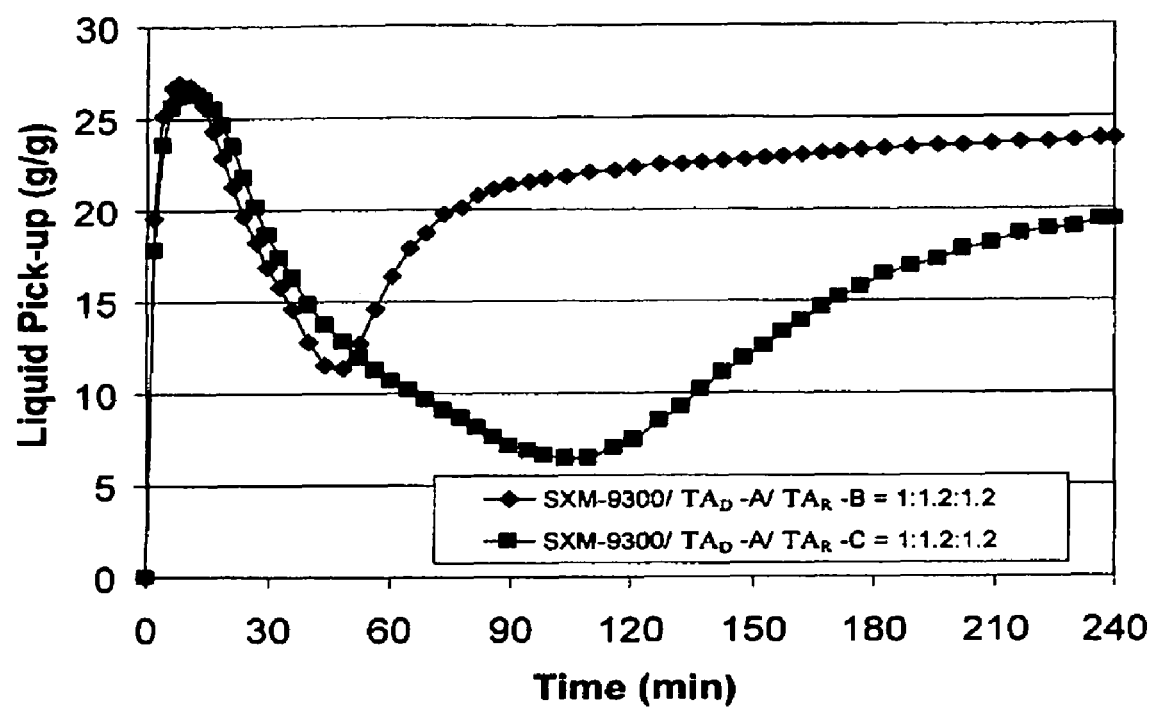
FIG. 15 is a graphical plot of swell/deswell/reswell curves for a specific SAP product and with various blends of deswell and reswell triggering agents.

FIG. 15 is a graphical plot of swell/deswell/reswell curves of a dry mixture of SXM-9300 with both the deswell and reswell triggering agents for Examples 23-24 and as shown in Table 11. In these examples, the starting point for the reswelling step was controlled by the release rate of the reswell triggering agent.

Figure 16:
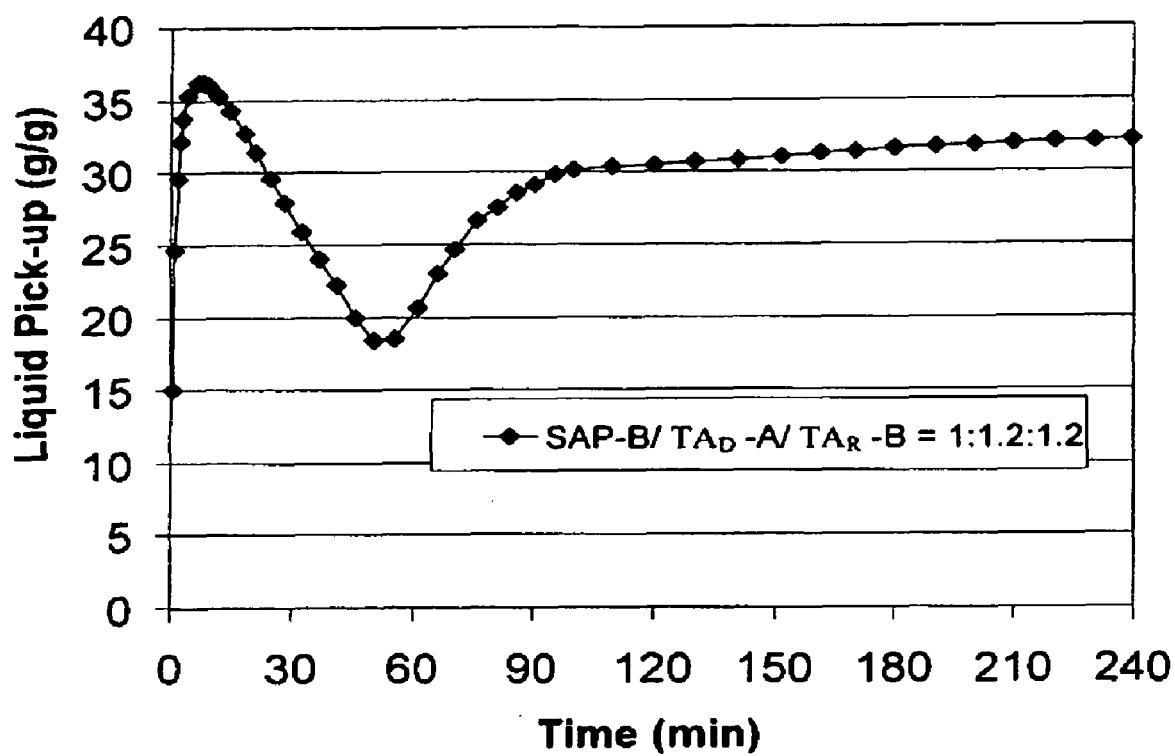
FIG. 16 is a graphical plot of swell/deswell/reswell curves for superabsorbent material SAP-B and with triggering agents $TA_D$-A and $TA_R$-B.

FIG. 16 is a graphical plot of swell/deswell/reswell curves for Example 25 and as shown in Table 11. In this example, SAP-B, a superabsorbent polymer composition comprising an encapsulated blowing agent, gave improved swelling capacity due to fast absorption rate compared with SXM-9300.

Figure 17:
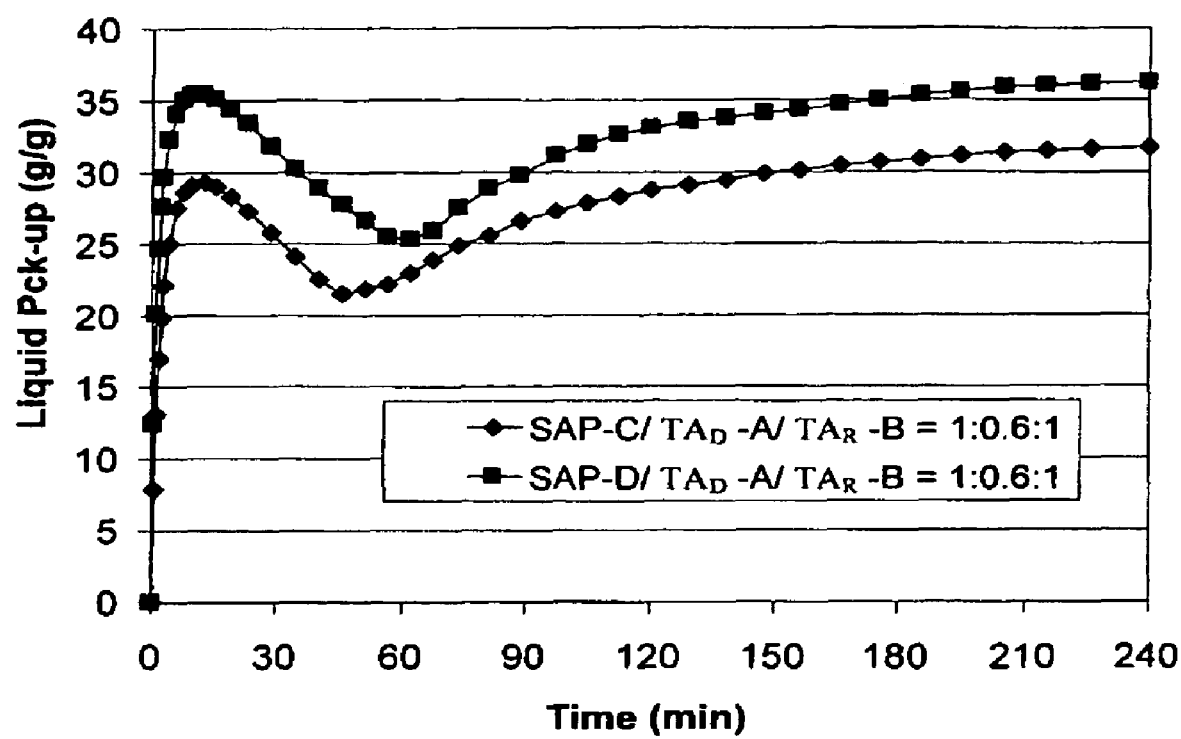
FIG. 17 is a graphical plot of swell/deswell/reswell curves for SAP-C and SAP-D and with various blends of triggering agents $TA_D$-A and $TA_R$-B.

FIG. 17 is a graphical plot of swell/deswell/reswell curves for Examples 26-27 and as shown in Table 11. In these examples, SAP-C and SAP-D, superabsorbent polymer compositions having about 50% DN, afforded improved swelling and reswelling capacities and mass efficiency compared with SXM-9300. SAP-D exhibits an improved swelling capacity over SAP-C also due to its fast absorption rate.

Examples 28-32

Table 12 summarizes the absorbent compositions comprising SXM-9300 or a superabsorbent polymer composition of the present invention, a deswell triggering agent comprising multivalent cations, and a reswell triggering agent comprising anions which are able to complex with the multivalent cations of the deswell triggering agent to form an insoluble salt having solubility product constant $K_{sp} < 10^{-5}$. The swell/deswell/reswell curves were measured according to the general procedures described in the Swell/Deswell/Reswell Test.

TABLE 12

Absorbent compositions having triggering agents

| Examples | SAP | Deswell triggering agent | Reswell triggering agent | Ratio |
|---|---|---|---|---|
| 28 | SXM-9300 | $TA_D$ - C | $TA_R$ - A | 1:0.8:1.6 |
| 29 | SAP-B | $TA_D$ - C | $TA_R$ - A | 1:1:1.2 |
| 30 | SAP-B | $TA_D$ - F | $TA_R$ - C | 1:1:1 |
| 31 | SAP-D | $TA_D$ - F | $TA_R$ - C | 1:0.4:0.8 |
| 32 | SAP-D | $TA_D$ - F | $TA_R$ - C | 1:0.5:1 |

Figure 18:
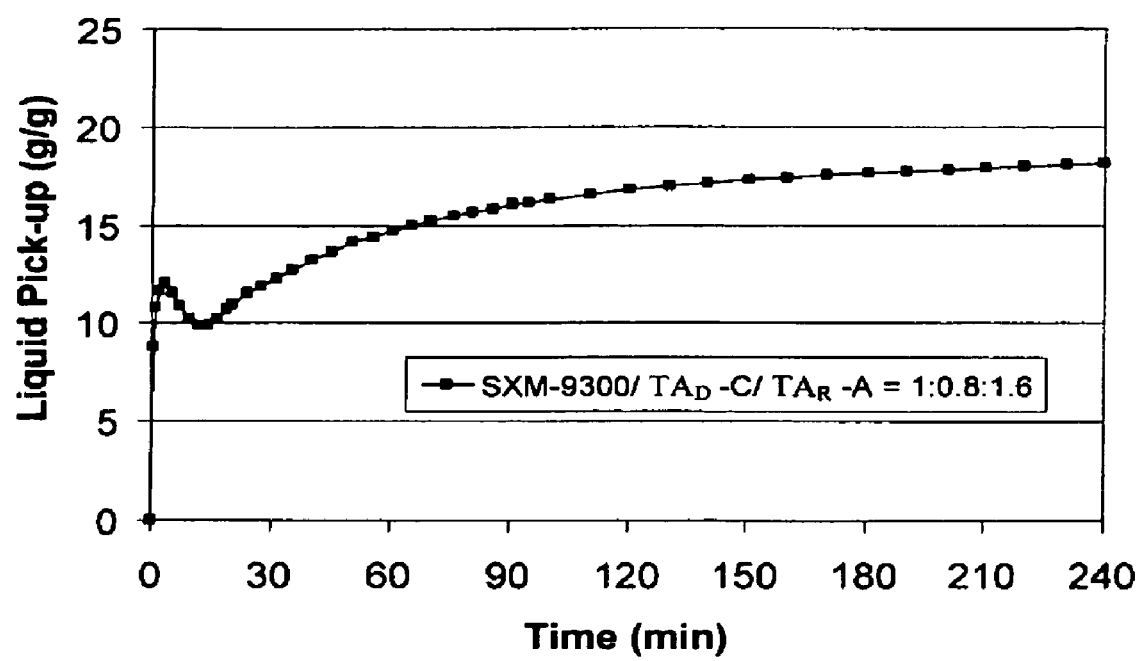
FIG. 18 is a graphical plot of swell/deswell/reswell curves for a specific SAP product and with triggering agents $TA_D$-C and $TA_R$-A.

FIG. 18 is a graphical plot of swell/deswell/reswell curves for Example 28 and as shown in Table 12 as measured by the Swell/Deswell/Reswell Test. In this example, the SAPs exhibited swell/deswell/reswell behavior after exposure to 0.9% saline solution.

Figure 19:
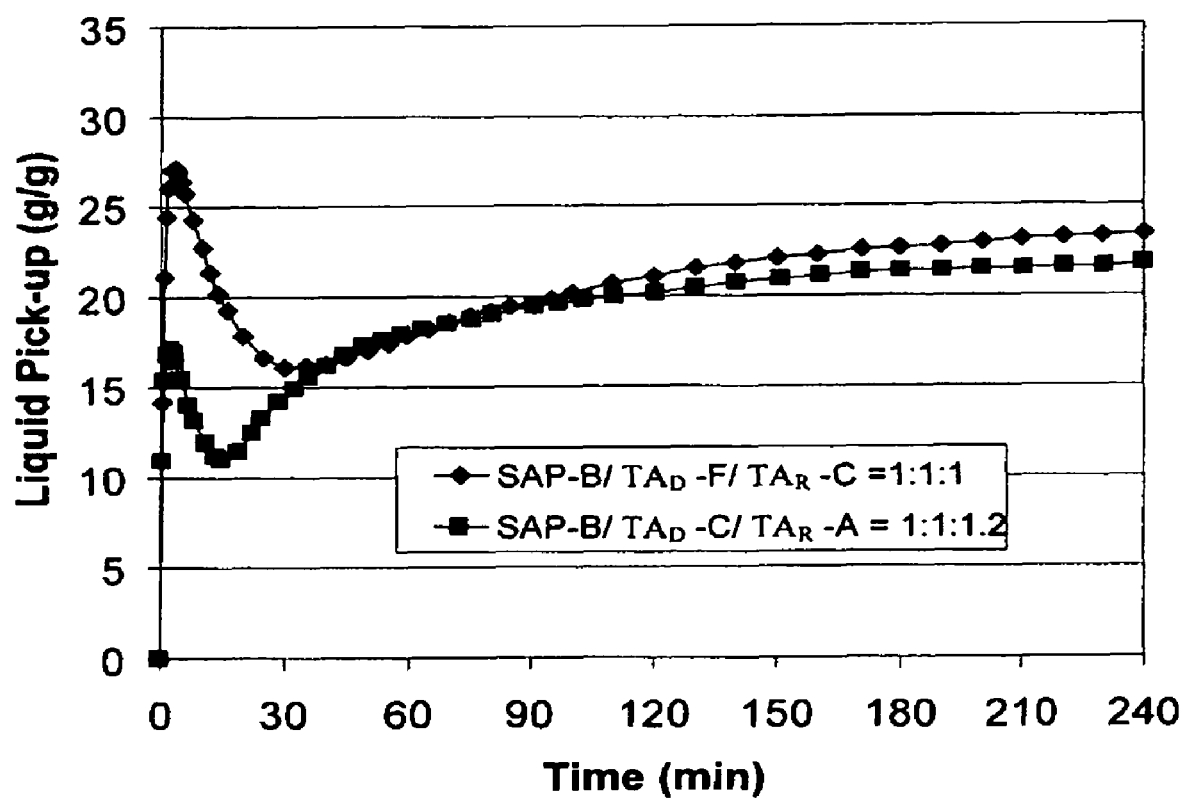
FIG. 19 is a graphical plot of swell/deswell/reswell curves for superabsorbent material SAP-B and with various blends of $TA_D$ and $TA_R$ triggering agents.

FIG. 19 is a graphical plot of swell/deswell/reswell curves for Examples 29-30 and as shown in Table 12 as measured by Swell/Deswell/Reswell Test. In these examples, SAP-B, a superabsorbent polymer composition comprising an encapsulated blowing agent, afforded improved swelling capacity compared with SXM-9300.

Figure 20:
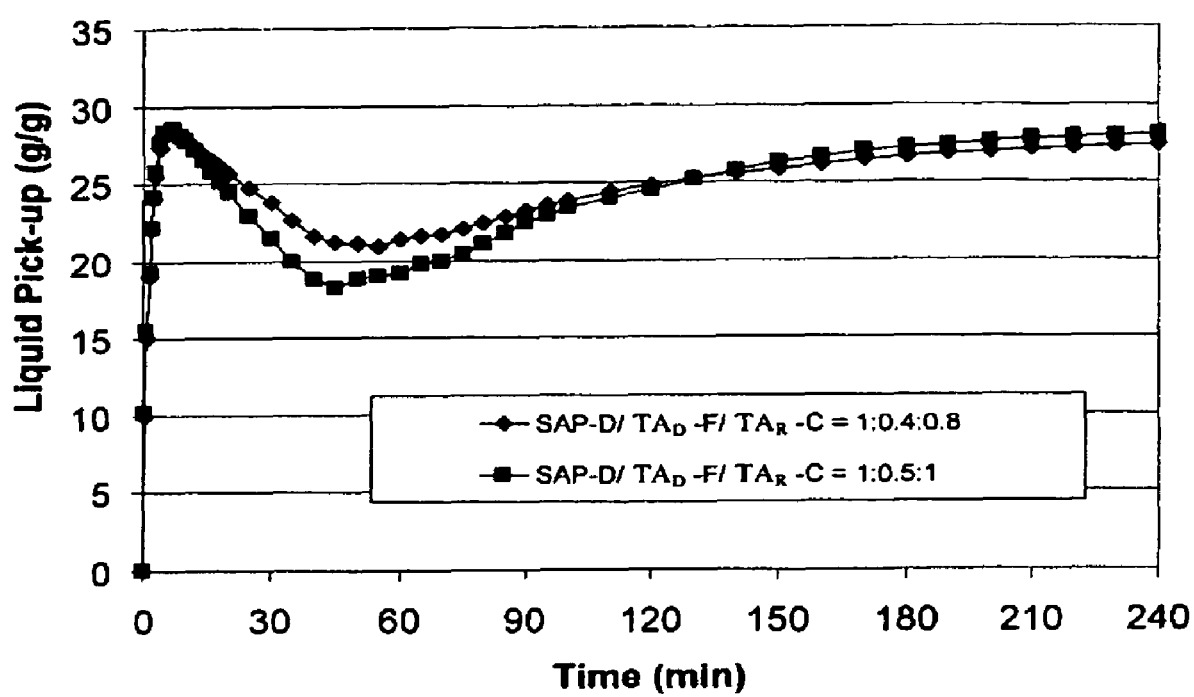
FIG. 20 is a graphical plot of swell/deswell/reswell curves for superabsorbent material SAP-D and with various blends of triggering agents $TA_D$-F and $TA_R$-C.

FIG. 20 is a graphical plot of swell/deswell/reswell curves for Examples 31-32 and as shown in Table 12 as measured by Swell/Deswell/Reswell Test. In these examples, SAP-D, a superabsorbent polymer composition comprising an encapsulated blowing agent and having about 50% DN, demonstrated the advantage of improved swelling and reswelling capacity and mass efficiency improvement.

Examples 33 to 38

Handsheets were prepared using standard airforming handsheet equipment. The resulting handsheet composites had dimensions of 25.4 cm wide by 43.2 cm long.

A modification to the forming unit was used which allowed individual 7.6 cm long zones to be made with specific amounts of pulp fibers and particulate materials (either SAP, or triggering agents, or combinations thereof) (see Table 13 below). However, it is noted that the two outside zones produced webs that were 10.2 cm long.

Fluff used was fiberized COOSASORB 100% Southern Softwood pulp (available from Bowater Corporation, having a place of business in Coosa Pines, Ala., U.S.A.). The SAP for Example 33 was FAVOR SXM-9300 (available from Evonik Stockhausen, Inc., having a place of business in Greensboro, N.C., U.S.A.). The superabsorbent polymer composition for Examples 34-38 was SAP-D. The deswell triggering agent used in Examples 34-38 was $TA_D$-A. The reswell triggering agent used in Examples 34-38 was $TA_R$-C.

For Examples 34-38, for each zone, the required amount of particulate materials (SAP-D, $TA_D$-A, and $TA_R$-C) was measured (see Table 13) and hand mixed in a beaker prior to web formation.

The fluff and particulate materials were formed onto a forming tissue having a basis weight of about 16.6 gsm (available as WHITE WRAP SHEET, available from Cellu Tissue Holdings, Inc., having a place of business in East Hartford, Conn., U.S.A.).

The handsheets were produced with the following procedure. A sheet of the forming tissue was placed on the bottom of the former. Then, the superabsorbent polymer composition (along with any triggering agents) and the fluff were each divided into about equal portions (i.e. 6 portions of fluff and 5 portions of particulate materials) for each zone identified in Table 13 below. Each fluff portion and particulate materials portion was alternatively introduced into the top of the former, allowing the compressed air to mix the fluff and particulate materials while the vacuum drew the material through the forming chamber and onto the forming tissue. This process was continued until the last portion of fluff was consumed, forming a substantially uniform distribution of fluff and particulate materials. This yielded absorbent composites which had a basis weight (of combined superabsorbent polymer composition and fluff) of 700 gsm. Any triggering agents added within a zone resulted in a total basis weight higher than 700 gsm for that zone.

Following web formation, another layer of the above forming tissue was placed on top of the formed composite.

TABLE 13

Zoned Handsheets with Deswell and Reswell Triggering agents in a Zoned Configuration Amount of components used to produced zoned handsheets - each zone 7.6 cm long by 25.4 cm wide (except zones 1 and 5 which are 7.6 cm long × 25.4 cm wide)

| | Zone 1 | | | | Zone 2 | | | | Zone 3 | | | |
|---|---|---|---|---|---|---|---|---|---|---|---|---|
| Example No. | SAP | $TA_D$-A | $TA_R$-C | fluff | SAP | $TA_D$-A | $TA_R$-C | fluff | SAP | $TA_D$-A | $TA_R$-C | fluff |
| Example 33 | 10.84 g | 0 g | 0 g | 7.23 g | 8.13 g | 0 g | 0 g | 5.42 g | 8.13 g | 0 g | 0 g | 5.42 g |
| Example 34 | 10.84 g | 6.50 g | 10.84 g | 7.23 g | 8.13 g | 5.42 g | 8.13 g | 5.42 g | 8.13 g | 5.42 g | 8.13 g | 5.42 g |
| Example 35 | 10.84 g | 0 g | 0 g | 7.23 g | 8.13 g | 5.42 g | 8.13 g | 5.42 g | 8.13 g | 5.42 g | 8.13 g | 5.42 g |
| Example 36 | 10.84 g | 0 g | 0 g | 7.23 g | 8.13 g | 2.71 g | 4.07 g | 5.42 g | 8.13 g | 5.42 g | 8.13 g | 5.42 g |
| Example 37 | 10.84 g | 0 g | 0 g | 7.23 g | 8.13 g | 1.36 g | 2.03 g | 5.42 g | 8.13 g | 2.71 g | 4.07 g | 5.42 g |
| Example 38 | 10.84 g | 0 g | 0 g | 7.23 g | 8.13 g | 0 g | 0 g | 5.42 g | 8.13 g | 5.42 g | 8.13 g | 5.42 g |

Amount of components used to produced zoned handsheets - each zone 7.6 cm long by 25.4 cm wide (except zones 1 and 5 which are 7.6 cm long × 25.4 cm wide)

| | Zone 4 | | | | Zone 5 | | | |
|---|---|---|---|---|---|---|---|---|
| Example No. | SAP | $TA_D$-A | $TA_R$-C | fluff | SAP | $TA_D$-A | $TA_R$-C | fluff |
| Example 33 | 8.13 g | 0 g | 0 g | 5.42 g | 10.84 g | 0 g | 0 g | 7.23 g |
| Example 34 | 8.13 g | 5.42 g | 8.13 g | 5.42 g | 10.84 g | 6.50 g | 10.84 g | 7.23 g |
| Example 35 | 8.13 g | 5.42 g | 8.13 g | 5.42 g | 10.84 g | 0 g | 0 g | 7.23 g |
| Example 36 | 8.13 g | 2.71 g | 4.07 g | 5.42 g | 10.84 g | 0 g | 0 g | 7.23 g |

TABLE 13-continued

Zoned Handsheets with Deswell and Reswell Triggering agents in a Zoned Configuration

| | | | | | | | | |
|---|---|---|---|---|---|---|---|---|
| Example 37 | 8.13 g | 1.36 g | 2.03 g | 5.42 g | 10.84 g | 0 g | 0 g | 7.23 g |
| Example 38 | 8.13 g | 0 g | 0 g | 5.42 g | 10.84 g | 0 g | 0 g | 7.23 g |

Example 33 includes commercial superabsorbent SXM-9300 while Examples 34-38 include SAP-D.

The resulting handsheet composite was compressed to a thickness of approximately 3.5 mm prior to testing, using a CARVER PRESS model #4531 (available from Carver, Inc., having a place of business in Wabash, Ind. U.S.A.).

Following handsheet preparation and densification, samples were cut to 7.6 cm wide by 38.1 cm long such that each zone above ended up being 7.6 cm long (i.e. 2.5 cm removed from length of zones 1 and 5). This resulted in the amounts of superabsorbent polymer composition, fluff, $TA_D$-A, $TA_R$-C in each 7.6 cm×7.6 cm zone as identified in Table 14 below.

TABLE 14

Absorbent materials in a Zoned Configuration

A 38.1 cm long × 7.6 cm wide composite with 5 equal zones and each zone having a size of 7.6 × 7.6 cm

| | Zone 1 | | | | Zone 2 | | | | Zone 3 | | | |
|---|---|---|---|---|---|---|---|---|---|---|---|---|
| Example No. | SAP | $TA_D$-A | $TA_R$-C | fluff | SAP | $TA_D$-A | $TA_R$-C | fluff | SAP | $TA_D$-A | $TA_R$-C | fluff |
| Example 33 | 2.44 g | 0 g | 0 g | 1.63 g | 2.44 g | 0 g | 0 g | 1.63 g | 2.44 g | 0 g | 0 g | 1.63 g |
| Example 34 | 2.44 g | 1.46 g | 2.44 g | 1.63 g | 2.44 g | 1.46 g | 2.44 g | 1.63 g | 2.44 g | 1.46 g | 2.44 g | 1.63 g |
| Example 35 | 2.44 g | 0 g | 0 g | 1.63 g | 2.44 g | 1.46 g | 2.44 g | 1.63 g | 2.44 g | 1.46 g | 2.44 g | 1.63 g |
| Example 36 | 2.44 g | 0 g | 0 g | 1.63 g | 2.44 g | 0.73 g | 1.22 g | 1.63 g | 2.44 g | 1.46 g | 2.44 g | 1.63 g |
| Example 37 | 2.44 g | 0 g | 0 g | 1.63 g | 2.44 g | 0.36 g | 0.61 g | 1.63 g | 2.44 g | 0.73 g | 1.22 g | 1.63 g |
| Example 38 | 2.44 g | 0 g | 0 g | 1.63 g | 2.44 g | 0 g | 0 g | 1.63 g | 2.44 g | 1.46 g | 2.44 g | 1.63 g |

A 38.1 cm long × 7.6 cm wide composite with 5 equal zones and each zone having a size of 7.6 × 7.6 cm

| | Zone 4 | | | | Zone 5 | | | |
|---|---|---|---|---|---|---|---|---|
| Example No. | SAP | $TA_D$-A | $TA_R$-C | fluff | SAP | $TA_D$-A | $TA_R$-C | fluff |
| Example 33 | 2.44 g | 0 g | 0 g | 1.63 g | 2.44 g | 0 g | 0 g | 1.63 g |
| Example 34 | 2.44 g | 1.46 g | 2.44 g | 1.63 g | 2.44 g | 1.46 g | 2.44 g | 1.63 g |
| Example 35 | 2.44 g | 1.46 g | 2.44 g | 1.63 g | 2.44 g | 0 g | 0 g | 1.63 g |
| Example 36 | 2.44 g | 0.73 g | 1.22 g | 1.63 g | 2.44 g | 0 g | 0 g | 1.63 g |
| Example 37 | 2.44 g | 0.36 g | 0.61 g | 1.63 g | 2.44 g | 0 g | 0 g | 1.63 g |
| Example 38 | 2.44 g | 0 g | 0 g | 1.63 g | 2.44 g | 0 g | 0 g | 1.63 g |

Example 33 includes commercial superabsorbent SXM-9300 available from Evonik Stockhausen, Inc. while Examples 34-38 include SAP-D.

Testing of Examples 33-38

7.6 cm wide by 38.1 cm long pieces of Examples 33-38 were subjected to the Cradle Intake Test. The distribution of liquid in the lengthwise direction of the examples was determined by x-ray imaging as described in the Cradle Intake Test method description.

The results of fluid distribution analysis are shown in Table 15 below.

TABLE 15

Liquid amount remaining in the insult area after each liquid insult.

| Example No. | Liquid Amount in Target Region from $13^{th}$ to $24^{th}$ cm (total composite length 38.1 cm) | | |
|---|---|---|---|
| | After $1^{st}$ Insult | After $2^{nd}$ Insult | After $3^{rd}$ Insult |
| Example 33 | 55 g | 114 g | 163 g |
| Example 34 | 54 g | 94 g | 127 g |
| Example 35 | 56 g | 96 g | 130 g |
| Example 36 | 54 g | 94 g | 124 g |
| Example 37 | 58 g | 107 g | 136 g |
| Example 38 | 57 g | 107 g | 129 g |

As can be seen in Table 15, after the $2^{nd}$ and $3^{rd}$ insults, all the examples containing triggering agents (Examples 34-38) show a reduction in the amount of liquid remaining in the insult area compared to Example 33. This indicates more liquid being distributed throughout the absorbent composite.

Examples 39-44

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The SAP for Comparative Example 39 was FAVOR SXM-9300. The SAP for Comparative Example 40 and Examples 41-44 was SAP-D. The deswell triggering agent used in Examples 41 and 43 was $TA_D$-G. The deswell triggering agent used in Examples 42 and 44 was $TA_D$-E. The reswell triggering agent used in Examples 41-44 was $TA_R$-F.

31.46 g of fluff and 47.18 g of SAP was formed onto a WHITE WRAP SHEET forming tissue having a basis weight of about 16.6 gsm. This amount of SAP and fluff yielded an absorbent composite with a basis weight of 717 gsm over the 25.4 cm wide by 43.2 cm long handsheet produced by this equipment.

The handsheets were produced with the following procedure. A sheet of the forming tissue was placed on the bottom of the former. Then, the SAP and the fluff were each divided into about equal portions (i.e. 6 portions of fluff and 5 portions of SAP). Each fluff portion and SAP portion was alternatively introduced into the top of the former, allowing the compressed air to mix the fluff and SAP while the vacuum drew the materials through the forming chamber and onto the forming tissue. This process was continued until the last portion of fluff was consumed, forming a substantially uniform distribution of fluff and SAP.

Following web formation, another layer of the above forming tissue was placed on top of the formed composite. The composite web was compressed to a thickness of approximately 3.6 mm prior to testing using a CARVER PRESS model #4531. Samples of the airformed handsheets were cut to 2.5 cm width by 38.1 cm length.

The following additional procedure was then followed for Examples 41-44: (see FIG. 21)

1. A 2.5 cm wide by 38.1 cm long piece of the above identified tissue was laid down on a flat, horizontal surface, and the central 22.9 cm in the lengthwise direction was marked.
2. The required amount of the triggering agent identified in Table 16 ($4^{th}$ column) was uniformly sprinkled onto the tissue, within the marked 22.9 cm long section, using a household salt shaker.
3. The appropriate 2.5 cm by 38.1 cm airformed handsheet (with the forming tissue still on the top and bottom) was placed onto the triggering agent (from step 2).
4. Another layer of the above identified tissue, with the central 7.6 cm in the lengthwise direction marked, was placed on top of the airformed handsheet from step 3.
5. The required amount of the triggering agent identified in Table 16 ($3^{rd}$ column) was uniformly sprinkled onto the tissue, within the marked 7.6 cm long section, using a household salt shaker.
6. Another 2.5 cm×38.1 cm layer of the above identified tissue was then placed on top of the triggering agent from step 5.

Figure 21:
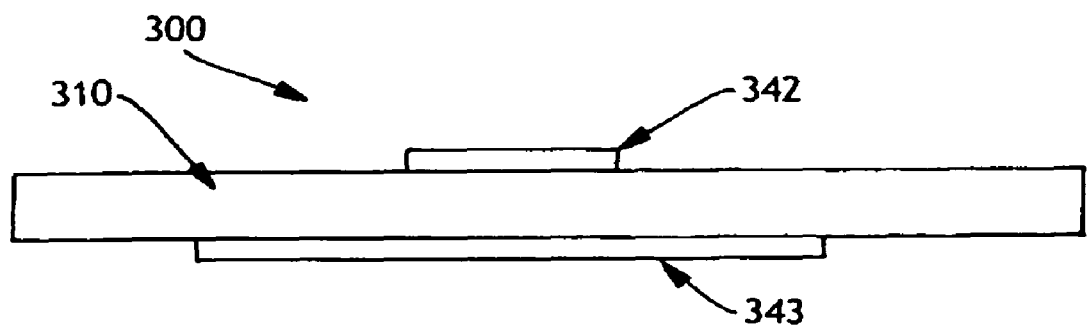
FIG. 21 is a side view of Examples 41 to 44.

The result was an absorbent system with triggering agents located in a discrete layer. FIG. 21 shows a cross-section view of a representative absorbent system 300 of Examples 41-44, where the system 300 has an absorbent composite 310 which comprises the SAP and fluff, a discrete layer 342 which includes the top triggering agent located on top-side of the composite 310, and a discrete layer 343 which includes the bottom triggering agent located on the bottom-side of the composite 310.

Testing of Examples 39-44

Examples 39-44 were subjected to the Horizontal Distribution test. The length of the wetted area of the absorbent system was determined by visual observation as indicated in the Horizontal Distribution test method. The results can be seen in Table 16 below.

TABLE 16

Wetted Length of Systems with Deswell and Reswell Triggering Agents in Layered Configuration after $2^{nd}$ Fluid Insult

| Example No. | Absorbent Composite (38.1 × 2.5 cm) - 717 gsm | Deswell and Reswell Triggering Agents in Layered Configuration | | Wetted Length after $2^{nd}$ Insult (cm) |
|---|---|---|---|---|
| | | Top (center 7.6 cm in length direction) | Bottom (center 22.9 cm in length direction) | |
| Comparative Example 39 | 60% 9300/40% fluff | None | None | 23.9 |
| Comparative Example 40 | 60% SAP-D/40% fluff | None | None | 20.8 |
| Example 41 | 60% SAP-D/40% fluff | 1.25 g $TA_D$ - G | 2.50 g $TA_R$ - F | 32.5 |
| Example 42 | 60% SAP-D/40% fluff | 1.25 g $TA_D$ - E | 2.50 g $TA_R$ - F | 30.2 |
| Example 43 | 60% SAP-D/40% fluff | 2.50 g $TA_R$ - F | 1.25 g $TA_D$ - G | 27.4 |
| Example 44 | 60% SAP-D/40% fluff | 2.50 g $TA_R$ - F | 1.25 g $TA_D$ - E | 26.9 |

As can be seen by the results in Table 16 (last column) the incorporation of the triggering agents to the system result in the fluid being distributed over a longer distance than either of Comparative Examples 39 and 40 which contain only SAP and fluff.

Examples 45-49

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The SAP for Comparative Example 45 was FAVOR SXM-9300. The superabsorbent polymer composition for Comparative Example 46 and Examples 47-49 was SAP-D. The deswell triggering agent used in Examples 47 to 49 was $TA_D$-G. The reswell triggering agent used in Examples 47 to 49 was $TA_R$-F.

31.46 g of fluff and 47.18 g of SAP were formed onto a WHITE WRAP SHEET forming tissue having a basis weight of about 16.6 gsm. This amount of SAP and fluff yielded an absorbent composite with a basis weight of 717 gsm over the 25.4 cm wide by 43.2 cm long handsheet produced by this equipment.

The handsheets were produced with the following procedure. A sheet of the forming tissue was placed on the bottom of the former. Then, the SAP and the fluff were each divided into about equal portions (i.e. 6 portions of fluff and 5 portions of SAP). Each fluff portion and SAP portion was alternatively introduced into the top of the former, allowing the compressed air to mix the fluff and SAP while the vacuum drew the materials through the forming chamber and onto the forming tissue. This process was continued until the last portion of fluff was consumed, forming a substantially uniform distribution of fluff and SAP.

Following web formation, another layer of the above forming tissue was placed on top of the formed composite. The composite was compressed to a thickness of approximately 3.6 mm prior to testing using a CARVER PRESS model #4531. Samples of the airformed handsheets were cut to 2.5 cm width by 38.1 cm length.

To complete the systems for Examples 47 to 49: (see FIG. 22)
1. A 38.1 cm long by 2.5 cm wide piece of the above identified tissue was laid down on a flat, horizontal surface, with every 7.6 cm in the lengthwise direction marked.
2. The required amount of the reswell triggering agent identified in Table 17 ($6^{th}$-$8^{th}$ column) was uniformly sprinkled onto the tissue in the middle three zones (zones 2, 3, and 4) with a household salt shaker.
3. The appropriate 38.1 cm by 2.5 cm airformed handsheet (with the forming tissue still on the top and bottom) was placed onto the triggering agent (from step 2).
4. Another layer of the above identified tissue with every 7.6 cm in the lengthwise direction marked was placed on top of the airformed handsheet from step 3.
5. The required amount of the deswell triggering agent identified in Table 17 ($3^{rd}$-$5^{th}$ column) was uniformly sprinkled onto the tissue in the middle three zones (zones 2, 3, and 4) with a household salt shaker.
6. Another 38.1 cm×2.5 cm layer of the above identified tissue was placed on top of the triggering agent from step 5.

Figure 22:
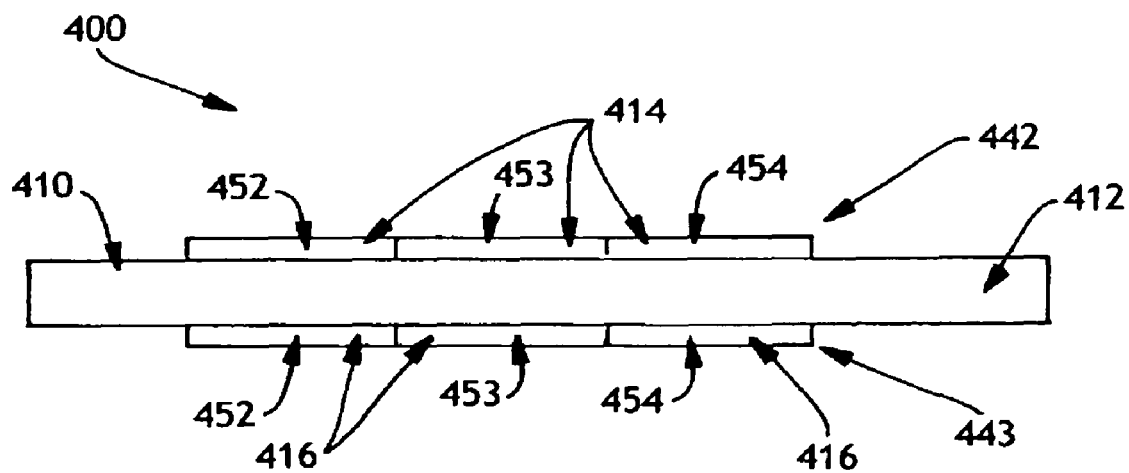
FIG. 22 is a side view of Examples 47 to 49.

The result was an absorbent system with triggering compositions located in a target zone of a discrete layer. FIG. 22 shows a cross-section view of a representative absorbent system 400 of Examples 45-49, where the system 400 has an absorbent composite 410 which comprises the SAP 412 and fluff; a discrete layer 442 which includes the deswell triggering agent 414 located on top-side of the composite 410 and includes zone 2 452, zone 3 453, and zone 4 454; and a discrete layer 443 which includes the reswell triggering agent 416 located on the bottom-side of the composite 410 and includes zone 2 452, zone 3 453, and zone 4 454.

Testing of Examples 45 to 49

Comparative Examples 45 and 46 and Examples 47-49 were subjected to the Horizontal Distribution Test. The length of the wetted area of the absorbent system was determined by visual observation as indicated in the Horizontal Distribution Test method. The results can be seen in Table 17 below.

TABLE 17

Wetted length after $2^{nd}$ insult with triggering agents in a layered configuration

| | | Deswell and Reswell Triggering agents in Layered/Zoned Configuration over Center of Composite | | | | | | |
|---|---|---|---|---|---|---|---|---|
| | | $TA_D$-G on top of composite (centered & three equal 7.62 × 2.54 cm zones) | | | $TA_R$-F at bottom of composite (centered & three equal 7.62 × 2.54 cm zones) | | | Wetted Length after $2^{nd}$ Insult |
| Example No. | Absorbent Composite (38.1 × 2.54 cm) - 717 gsm | Zone 2 | Zone 3 | Zone 4 | Zone 2 | Zone 3 | Zone 4 | (cm) |
| Comparative Example 45 | 60% 9300/40% fluff | 0 g | 0 g | 0 g | 0 g | 0 g | 0 g | 23.9 |
| Comparative Example 46 | 60% SAP-D/40% fluff | 0 g | 0 g | 0 g | 0 g | 0 g | 0 g | 20.8 |
| Example 47 | 60% SAP-D/40% fluff | 0.42 g | 0.42 g | 0.42 g | 0.83 g | 0.83 g | 0.83 g | 32.5 |
| Example 48 | 60% SAP-D/40% fluff | 0.21 g | 0.42 g | 0.21 g | 0.42 g | 0.83 g | 0.42 g | 31.2 |
| Example 49 | 60% SAP-D/40% fluff | 0.11 g | 0.42 g | 0.11 g | 0.11 g | 0.83 g | 0.11 g | 29.5 |

As can be seen by the results from Table 17 (last column) above that the incorporation of as little as 45% add-on of the combined triggering agents (relative to amount of superabsorbent polymer composition) can result in the fluid being distributed over a longer distance than either of the samples containing only SAP and fluff (Comparative Examples 45 and 46).

Examples 50-54

Example 50

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The SAP for Comparative Example 50 was FAVOR SXM-9300.

31.46 g of fluff and 47.18 g of SAP was formed onto a WHITE WRAP SHEET forming tissue having a basis weight of about 16.6 gsm. This amount of SAP and fluff yielded an absorbent composite with a basis weight of 717 gsm over the 25.4 cm wide by 43.2 cm long handsheet produced by this equipment.

The handsheets were produced with the following procedure. A sheet of the forming tissue was placed on the bottom of the former. Then, the SAP and the fluff were each divided into about equal portions (i.e. 6 portions of fluff and 5 portions of SAP). Each fluff portion and SAP portion was alternatively introduced into the top of the former, allowing the compressed air to mix the fluff and SAP while the vacuum draws the materials through the former chamber and onto the forming tissue. This process was continued until the last portion of fluff was consumed, forming a substantially uniform distribution of fluff and SAP.

Following web formation, another layer of the above forming tissue was placed on top of the formed composite. The composite web was compressed to a thickness of approximately 3.6 mm prior to testing using a CARVER PRESS model #4531.

A die was used to cut-out a piece of the handsheet described above into a generally hour glass shape with an overall surface area of 290 sq cm, a width in the crotch region of 6.4 cm, an overall length of 35.4 cm, and a width in the front of the piece of 10.2 cm.

This die cut absorbent was hand inserted and assembled into a typical step 4 size personal care product using standard components.

Example 51

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The superabsorbent polymer composition for Example 51 was SAP-D. The swell triggering agent used in Example 51 was $TA_D$-F. The reswell triggering agent used in Example 51 was $TA_R$-C.

31.46 g of fluff and 47.18 g of SAP, 23.59 g of $TA_D$-F, and 47.18 g of $TA_R$-C were formed onto a WHITE WRAP SHEET forming tissue having a basis weight of about 16.6 gsm. This amount of particulate material and fluff yielded an absorbent composite with a basis weight of 1362 gsm over the 25.4 cm wide by 43.2 cm long handsheet produced by this equipment.

The handsheets were produced with the following procedure. The required amount of particulate material; SAP-D, $TA_D$-F, and $TA_R$-C was measured and hand mixed in a beaker prior to web formation. A sheet of forming tissue was placed on the bottom of the former. Then, the particulate material and the fluff were each divided into about equal portions (i.e. 6 portions of fluff and 5 portions of particulate material). Each fluff portion and particulate material portion was alternatively introduced into the top of the former, allowing the compressed air to mix the fluff and particulate material while the vacuum drew the materials through the forming chamber and onto the forming tissue. This process was continued until the last portion of fluff was consumed, forming a substantially uniform distribution of fluff and particulate material.

Following web formation, another layer of the above forming tissue was placed on top of the formed composite. The composite web was compressed to a thickness of approximately 3.6 mm (0.2 g/cc based on mass of fiber and SAP) prior to testing using a CARVER PRESS model #4531.

A die was used to cut-out a piece of the handsheet described above into a generally hour glass shape with an overall surface area of 290 sq cm, a width in the crotch region of 6.4 cm, an overall length of 35.4 cm, and a width in the front of the piece of 10.2 cm.

This die cut absorbent was hand inserted and assembled into a typical step 4 size personal care product (diaper) using standard components.

Examples 52-54

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The superabsorbent polymer composition for Example 52 was SAP-D. The superabsorbent polymer composition for Examples 53 and 54 was SAP-F. The deswell triggering agent used in Examples 52-54 was $TA_D$-G. The reswell triggering agent used in Examples 52-54 was $TA_R$-F.

31.46 g of fluff and 47.18 g of superabsorbent polymer composition were formed onto a WHITE WRAP SHEET forming tissue having a basis weight of about 16.6 gsm. This amount of SAP and fluff yielded an absorbent composite with a basis weight of 717 gsm over the 25.4 cm wide by 43.2 cm long handsheet produced by this equipment.

The handsheets were produced with the following procedure. A sheet of the forming tissue was placed on the bottom of the former. Then, the SAP and the fluff were each divided into about equal portions (i.e. 6 portions of fluff and 5 portions of superabsorbent polymer composition). Each fluff portion and superabsorbent polymer composition portion was alternatively introduced into the top of the former, allowing the compressed air to mix the fluff and SAP composition while the vacuum drew the materials through the forming chamber and onto the forming tissue. This process was continued until the last portion of fluff was consumed, forming a substantially uniform distribution of fluff and superabsorbent polymer composition.

Following web formation, another layer of the above forming tissue was placed on top of the formed composite. The composite web was compressed to a thickness of approximately 3.6 mm (0.2 g/cc based on mass of fiber and SAP) prior to testing using a CARVER PRESS model #4531.

A die was used to cut-out a piece of the handsheet described above into a generally hour glass shape with an overall surface area of 290 sq cm, a width in the crotch region of 6.4 cm, an overall length of 35.4 cm, and a width in the front of the piece of 10.2 cm.

To complete the systems for Examples 52-54:
1. A 38.1 cm long by 12.7 cm wide piece of the above identified tissue was laid down, with every 7.6 cm in the lengthwise direction marked.
2. A light layer (5-25 gsm) of construction adhesive (NS34-5610 available from National Starch and Chemical, having a place of business in Bridgewater, N.J., U.S.A.) was sprayed onto the tissue using a spray gun, such as a PAM 600 Spraymatic available from Fastening Technology, Inc., having a place of business in Charlotte, N.C., U.S.A.
3. The required amount of the reswell triggering agent identified in Table 18 ($6^{th}$-$8^{th}$ column) was uniformly sprinkled onto the tissue in the middle three zones (zones 2, 3, and 4) with a household salt shaker.
4. The tissue/adhesive/triggering agent laminate was folded in half (in the width-wise direction) to yield a 6.4 cm wide by 38.1 cm long sample. 2.5 cm was trimmed from the zone 5 portion of the laminate, resulting in a tissue/adhesive/reswell triggering agent laminate which was 6.4 cm wide by 35.6 cm long.
5. A 38.1 cm long by 12.7 cm wide piece of the above identified tissue was laid down, with every 7.6 cm in the lengthwise direction marked.
6. A light layer (5-25 gsm) of construction adhesive (NS34-5610.) was sprayed onto the tissue using a spray gun, such as a PAM 600 Spraymatic.
7. The required amount of the deswell triggering agent identified in Table 18 ($3^{rd}$-$5^{th}$ column) was uniformly sprinkled onto the tissue in the middle three zones (zones 2, 3, and 4) with a household salt shaker.
8. The tissue/adhesive/triggering agent laminate was folded in half (in the width-wise direction) to yield a 6.4 cm wide by 38.1 cm long sample. 2.5 cm was trimmed from the zone 5 portion of the laminate, resulting in a tissue/adhesive/deswell triggering agent laminate which was 6.4 cm wide by 35.6 cm long.
9. The tissue/adhesive/reswell triggering agent laminate from step 4 was laid down on a flat, horizontal workbench.
10. The appropriate die cut SAP/fluff absorbent composite identified in Table 18 was positioned on top of the laminate from step 4 such that that front end of each piece was aligned and the laminate from step 4 was aligned in the width-wise direction with the crotch portion of the die cut absorbent composite.
11. The tissue/adhesive/deswell triggering agent laminate from step 8 was placed on top of the die cut absorbent composite such that that front end of each piece was aligned and the laminate from step 8 was aligned in the width-wise direction with the crotch portion of the die cut absorbent composite.

Figure 23:
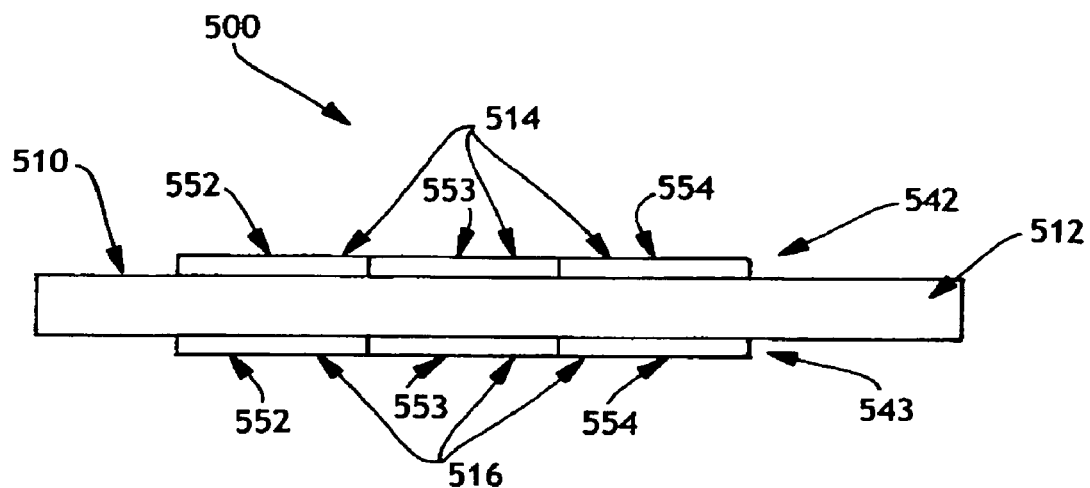
FIG. 23 is a side view of Examples 52 to 54.
Figure 24:
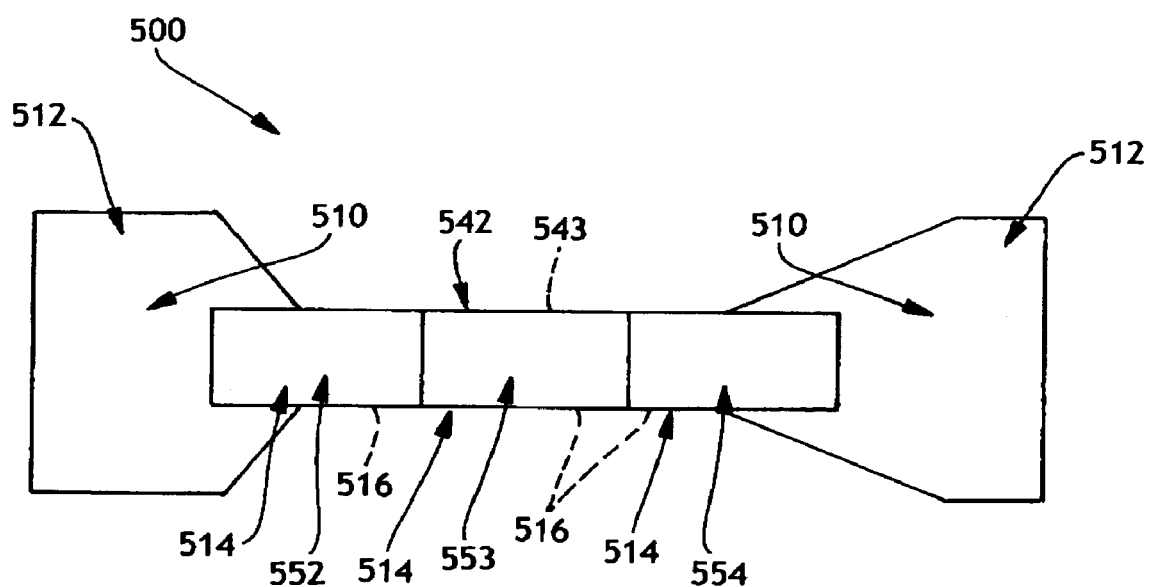
FIG. 24 is a top view of Examples 52 to 54.

The above described sandwich construction of the tissue/adhesive/deswell triggering agent laminate—die cut absorbent composite—tissue/adhesive/reswell triggering agent laminate was hand inserted and assembled into a typical step 4 size personal care product (diaper) using standard components. FIG. 23 shows a cross-section view of a representative absorbent system 500 of Examples 52-54, where the system 500 has an absorbent composite 510 which comprises the SAP 512 and fluff; a discrete layer 542 which includes the deswell triggering agent 514 located on top-side of the composite 510 and includes zone 2 552, zone 3 553, and zone 4 554; and a discrete layer 543 which includes the reswell triggering agent 516 located on the bottom-side of the composite 510 and includes zone 5 552, zone 5 553, and zone 4 554. FIG. 24 is a top view of FIG. 23.

TABLE 18

Absorbent Product Composition and Structure Description

| | | Deswell and Reswell Triggering Agents in Layered Configuration over center of composite | | | | | |
|---|---|---|---|---|---|---|---|
| | | $TA_D$-G on top of composite (centered & three equal 7.6 × 6.4 cm zones) | | | $TA_R$-F at bottom of composite (centered & three equal 7.6 × 6.4 cm zones) | | |
| Example No. | Diaper Core Composition | Zone 2 | Zone 3 | Zone 4 | Zone 2 | Zone 3 | Zone 4 |
| Comparative Example 50 | 12.5 g 9300/8.3 g fluff | 0 g | 0 g | 0 g | 0 g | 0 g | 0 g |
| Example 51 | 12.5 g SAP-D/6.3 g $TA_D$-F/12.5 g $TA_R$-C/8.3 g fluff | 0 g | 0 g | 0 g | 0 g | 0 g | 0 g |
| Example 52 | 12.5 g SAP-D/8.3 g fluff | 1.04 g | 1.04 g | 1.04 g | 2.08 g | 2.08 g | 2.08 g |
| Example 53 | 12.5 g SAP-F/8.3 g fluff | 1.04 g | 1.04 g | 1.04 g | 2.08 g | 2.08 g | 2.08 g |
| Example 54 | 12.5 g SAP-F/8.3 g fluff | 0.26 g | 1.04 g | 0.26 g | 0.52 g | 2.08 g | 0.52 g |

Testing of Examples 50-54

Twelve diapers containing absorbent systems for each of Comparative Example 50 and Examples 51-54 were tested using the Mannequin Test Method.

Each absorbent article tested had a conventional hour glass shaped absorbent system. The absorbent articles each contained a 150 gsm intake layer (i.e., surge layer) between the absorbent system and the body side liner.

Fluid was added to the absorbent articles using "male" mannequins. The insult fluid (0.9 wt % aqueous sodium chloride solution) was delivered to the products at slightly below body temperature (about 33° C.).

A relationship between the wetted area versus amount of liquid added at leakage was determined based on the amount of liquid in the product at the time of leakage. The wetted area was determined by x-ray image as described in the Mannequin Test method. A linear regression of the data points containing at least 50 g of liquid was used to interpolate the wetted area at 100 g liquid loading and 175 g liquid loading. Results are seen in Table 19 below.

TABLE 19

| | Wetted Area of Used Products (cm²) | |
|---|---|---|
| Example No. | At a Diaper Loading Around 100 g | At a Diaper Loading Around 175 g |
| Comparative Example 50 | 145 | 166 |
| Example 51 | 160 | 184 |
| Example 52 | 150 | 191 |
| Example 53 | 155 | 176 |
| Example 54 | 155 | 188 |

As can be seen from the results in Table 19, the wetted area for all of the samples comprising triggering agents show higher wetted area at both 100 g of nominal loading and 175 g of nominal loading compared to the control system which contained only SAP and fluff (Comparative Example 50). This demonstrates increased distribution of liquid through the absorbent pad.

Examples 55 and 56

Example 55

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The SAP for Comparative Example 55 was FAVOR SXM-9300.

31.46 g of fluff and 47.18 g of SAP was formed onto a WHITE WRAP SHEET forming tissue having a basis weight of about 16.6 gsm. This amount of SAP and fluff yielded an absorbent composite with a basis weight of 717 gsm over the 25.4 cm wide by 43.2 cm long handsheet produced by this equipment.

The handsheets were produced with the following procedure. A sheet of the forming tissue was placed on the bottom of the former. Then, the SAP and the fluff were each divided into about equal portions (i.e. 6 portions of fluff and 5 portions of SAP). Each fluff portion and SAP portion was alternatively introduced into the top of the former, allowing the compressed air to mix the fluff and SAP while the vacuum drew the materials through the forming chamber and onto the forming tissue. This process was continued until the last portion of fluff was consumed, forming a substantially uniform distribution of fluff and SAP.

Following web formation, another layer of the above forming tissue was placed on top of the formed composite. The composite web was compressed to a thickness of approximately 3.6 mm prior to testing using a CARVER PRESS model #4531. Samples of the airformed handsheets were cut to 7.6 cm width by 38.1 cm length.

Example 56

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The superabsorbent polymer composition for Example 56 was SAP-D. The deswell triggering agent used was $TA_D$-F. The reswell triggering agent used in Example 56 was $TA_R$-C.

31.46 g of fluff and 47.18 g of superabsorbent polymer composition, 23.59 g of $TA_D$-F, and 23.59 g of $TA_R$-C were formed onto a WHITE WRAP SHEET forming tissue having a basis weight of about 16.6 gsm. This amount of particulate material and fluff yielded an absorbent composite with a basis weight of 1147 gsm over the 25.4 cm wide by 43.2 cm long handsheet produced by this equipment.

The handsheets were produced with the following procedure. A sheet of the forming tissue was placed on the bottom of the former. The required amount of particulate material; SAP-D, $TA_D$-F, and $TA_R$-C was measured and handmixed in a beaker prior to web formation. Then, the particulate material and the fluff were each divided into about equal portions (i.e. 6 portions of fluff and 5 portions of particulate material). Each fluff portion and particulate material portion was alternatively introduced into the top of the former, allowing the compressed air to mix the fluff and particulate material while the vacuum drew the materials through the forming chamber and onto the forming tissue. This process was continued until the last portion of fluff was consumed, forming a substantially uniform distribution of fluff and particulate material.

Following web formation, another layer of the above forming tissue was placed on top of the formed composite. The composite web was compressed to a thickness of approximately 3.6 mm prior to testing using a CARVER PRESS model #4531. Samples of the airformed handsheets were cut to 7.6 cm width by 38.1 cm length.

Testing of Examples 55 and 56

Examples 55 and 56 were tested according to the Horizontal Intake and Distribution Test. Wetted length following each liquid insult (as mentioned in the test method) are indicated in Table 20 below.

TABLE 20

| Example | Wetted Length after 1$^{st}$ Insult (cm) | Wetted Length after 2$^{nd}$ Insult (cm) | Wetted Length after 3$^{rd}$ Insult (cm) |
|---|---|---|---|
| Comparative Example 55 | 18.5 | 20.5 | 25 |
| Example 56 | 21.0 | 31 | >38.1* |

*The entire length of the samples for Example 56 was wetted after 3$^{rd}$ insult As can be seen, Example 56 (containing triggering agents), results in greater distribution of liquid for every insult compared to the control, Comparative Example 55 in which no triggering agents are present.

Examples 57-59

Handsheets were prepared using standard airforming handsheet equipment. The resulting handsheet composites had dimensions of 25.4 cm wide by 43.2 cm long.

Fluff used was fiberized COOSASORB 100% Southern Softwood pulp. The superabsorbent polymer composition for Examples 57-59 was SAP-F. The deswell triggering agent used in Examples 57 to 59 was $TA_D$-G. The reswell triggering agent used in Examples 57 to 59 was $TA_R$-F.

31.46 g of fluff and 47.18 g of superabsorbent polymer composition were formed onto a WHITE WRAP SHEET forming tissue having a basis weight of about 16.6 gsm. This amount of SAP and fluff yielded an absorbent composite with a basis weight of 717 gsm over the 25.4 cm wide by 43.2 cm long handsheet produced by this equipment.

The handsheets were produced with the following procedure. A sheet of the forming tissue was placed on the bottom of the former. Then, the superabsorbent polymer composition and the fluff were each divided into about equal portions (i.e. 6 portions of fluff and 5 portions of SAP). Each fluff portion and superabsorbent polymer composition portion was alternatively introduced into the top of the former, allowing the compressed air to mix the fluff and superabsorbent polymer composition while the vacuum drew the materials through the forming chamber and onto the forming tissue. This process was continued until the last portion of fluff was consumed, forming a substantially uniform distribution of fluff and superabsorbent polymer composition.

Following web formation, another layer of the above forming tissue was placed on top of the formed composite. The composite web was compressed to a thickness of approximately 3.6 mm prior to testing using a CARVER PRESS model #4531. Samples of the airformed handsheets were cut to 6.4 cm width by 38.1 cm length.

To complete the systems for Examples 57 to 59: (see FIG. 22)

1. A 38.1 cm long by 6.4 cm wide piece of the above identified tissue was laid down on a flat, horizontal surface, with every 7.6 cm in the lengthwise direction marked.
2. The required amount of the reswell triggering agent identified in Table 21 (6$^{th}$-8$^{th}$ column) was uniformly sprinkled onto the tissue in the middle three zones (zones 2, 3, and 4) with a household salt shaker.
3. The appropriate 38.1 cm by 6.4 cm airformed handsheet (with the forming tissue still on the top and bottom) was placed onto the triggering agent (from step 2).
4. Another layer of the above identified tissue with every 7.6 cm in the lengthwise direction marked was placed on top of the airformed handsheet from step 3.
5. The required amount of the deswell triggering agent identified in Table 21 (3$^{rd}$-5$^{th}$ column) was uniformly sprinkled onto the tissue in the middle three zones (zones 2, 3, and 4) with a household salt shaker.
6. Another 38.1 cm×6.4 cm layer of the above identified tissue was placed on top of the triggering agent from step 5.

Testing of Examples 57 to 59

Examples 57-59 were subjected to the Horizontal Intake and Distribution test with two modifications. 60 cc of saline solution was added during each liquid addition, rather than 70 cc (see step 3). Instead of measuring the wetted length of the absorbent system with x-ray densitometry (see step 4), the thickness of the wet absorbent was measured using a conventional thickness tester, such as Sony Digital Indicator Model #U30A, under a measurement pressure of 3450 dynes/cm$^2$. The results can be seen in Table 21 below.

TABLE 21

Wet Thickness after 2$^{nd}$ insult with triggering agents in a layered configuration

| | | Deswell and Reswell Triggering Agents in Layered/Zoned Configuration over Center of Composite | | | | | | |
|---|---|---|---|---|---|---|---|---|
| | | TA$_D$-G on top of composite (centered & three equal 7.62 × 6.4 cm zones) | | | TA$_R$-F at bottom of composite (centered & three equal 7.62 × 6.4 cm zones) | | | Wet Thickness after 2$^{nd}$ Insult |
| Example No. | Absorbent Composite (38.1 × 6.4 cm) - 717 gsm | Zone 2 | Zone 3 | Zone 4 | Zone 2 | Zone 3 | Zone 4 | (mm) |
| Example 57 | 60% SAP-D/40% fluff | 0.20 g | 0.78 g | 0.20 g | 0.20 g | 0.78 g | 0.20 g | 12.2 |
| Example 58 | 60% SAP-D/40% fluff | 0.23 g | 0.94 g | 0.23 g | 0.23 g | 0.94 g | 0.23 g | 11.6 |
| Example 59 | 60% SAP-D/40% fluff | 0.26 g | 1.04 g | 0.26 g | 0.52 g | 2.08 g | 0.52 g | 12.5 |

As can be seen by the results from Table 21 (last column) above that the incorporation of as little as 23% add-on of the combined triggering agents (relative to amount of superabsorbent polymer composition) (Example 57) can result in the fluid being distributed over a longer distance, resulting in a reduced wet thickness in the target zone, than the sample containing 45% add-on of the combined trigger compositions (Example 59).

It will be appreciated that details of the foregoing examples, given for purposes of illustration, are not to be construed as limiting the scope of this invention. Although only a few exemplary aspects of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many aspects may be conceived that do not achieve all of the advantages of some aspects, particularly of the desirable aspects, yet the absence of a particular advantage shall not be construed to necessarily mean that such an aspect is outside the scope of the present invention. As various changes could be made in the above constructions without departing from the scope of the invention, it is intended that all matter contained in the above description shall be interpreted as illustrative and not in a limiting sense.

What is claimed is:

1. An absorbent composite comprising:
   an absorbent composition;
   wherein the absorbent composition comprises a SAP, a deswell triggering agent ($TA_D$) and a reswell triggering agent ($TA_R$);
   wherein the SAP, the $TA_D$ and the $TA_R$ are all selected from either solubility-based chemistry or neutralization-based chemistry groupings;
   wherein the $TA_D$ comprises a first water-soluble solid chemical wherein the $TA_D$ has a release profile for releasing the water-soluble solid chemical wherein the release profile is selected from a singular release profile or a sigmoidal release profile;
   wherein the $TA_R$ comprises a second water-soluble solid chemical wherein the reswell triggering anent has a sigmoidal release profile for releasing the second water-soluble solid chemical;
   wherein the first water-soluble chemical has a higher cumulative release than the second water-soluble chemical after exposure to aqueous fluid and before about 100% release; and
   wherein the absorbent composite has a top side and an opposing bottom side.

2. The absorbent composite of claim 1 wherein the SAP, $TA_D$ and $TA_R$ are substantially uniformly distributed within the composite.

3. The absorbent composite of claim 1 further comprising a target zone and a perimeter region; wherein the target zone comprises the SAP, $TA_D$ and $TA_R$; and wherein the perimeter region comprises substantially only the SAP.

4. The absorbent composite of claim 1 wherein the SAP is a superabsorbent polymer composition.

5. The absorbent composite of claim 1 wherein the absorbent composite is present in an absorbent article which further comprises a topsheet and a backsheet, wherein the absorbent composite is disposed between the topsheet and the backsheet.

6. The absorbent composite of claim 1 wherein the composite is present in an absorbent article selected from personal care absorbent articles, health/medical absorbent articles, household/industrial absorbent articles or sports/construction absorbent articles.

7. An absorbent composite having a fibrous matrix comprising:
   a SAP, a deswell triggering agent ($TA_D$) and a reswell triggering agent ($TA_R$);
   wherein the SAP, the $TA_D$ and the $TA_R$ are all selected from either solubility-based chemistry or neutralization-based chemistry groupings;
   wherein the absorbent composite has a top layer, a middle layer and a bottom layer;
   wherein the middle layer is disposed between the top layer and the bottom layer; and
   wherein each of SAP, $TA_D$ and $TA_R$ is present in at least one of the layers; and wherein the middle layer comprises substantially only SAP.

8. The absorbent composite of claim 7 wherein the SAP is a superabsorbent polymer composition.

9. The absorbent composite of claim 7 wherein $TA_D$ comprises a first water-soluble solid chemical wherein the $TA_D$ has a release profile for releasing the water-soluble solid chemical wherein the release profile is selected from a singular release profile or a sigmoidal release profile; wherein the $TA_R$ comprises a second water-soluble solid chemical wherein the reswell triggering agent has a sigmoidal release profile for releasing the second water-soluble solid chemical; and wherein the first water-soluble chemical has a higher cumulative release than the second water-soluble chemical after exposure to aqueous fluid and before about 100% release.

10. The absorbent composite of claim 7 wherein the middle layer comprises substantially only SAP; wherein the top layer comprises substantially only $TA_D$; and wherein the bottom layer comprises substantially only $TA_R$.

11. The absorbent composite of claim 7 wherein the middle layer comprises substantially only SAP; wherein the top layer comprises substantially only $TA_D$; wherein the bottom layer comprises substantially only $TA_R$; and wherein at least one of the $TA_D$ and $TA_R$ is located substantially only in a target zone of the top layer and/or bottom layer, respectively.

12. The absorbent composite of claim 7 wherein the middle layer comprises substantially only SAP; and wherein the top layer and the bottom layer each comprise substantially only $TA_D$ and $TA_R$ combined.

13. The absorbent composite of claim 7 wherein the top layer and the bottom layer each comprise substantially only $TA_D$ and $TA_R$ combined; and wherein the $TA_D$ and $TA_R$ are located substantially only in a target zone of at least one of the top layer and bottom layer.

14. The absorbent composite of claim 7 wherein the top layer, the middle layer, and the bottom layer each comprise substantially only one of the SAP, $TA_D$ and $TA_R$; and wherein none of the layers is the same.

15. The absorbent composite of claim 7 further comprising a first intermediate layer and a second intermediate layer, wherein the first intermediate layer is disposed between the top layer and the middle layer, and wherein the second intermediate layer is disposed between the middle layer and the bottom layer; wherein the top layer, the middle layer, and the bottom layer each comprise substantially only SAP; and wherein the first intermediate layer and the second intermediate layer each comprise SAP, $TA_D$ and $TA_R$.

16. The absorbent composite of claim 7 further comprising a first intermediate layer and a second intermediate layer, wherein the first intermediate layer is disposed between the top layer and the middle layer, and wherein the second intermediate layer is disposed between the middle layer and the bottom layer; wherein the top layer, the middle layer, and the bottom layer each comprise substantially only SAP; wherein the first intermediate layer comprises substantially only $TA_D$; and wherein the second intermediate layer comprises substantially only $TA_R$.

17. The absorbent composite of claim 7 wherein the absorbent composite is present in an absorbent article which further comprises a topsheet and a backsheet, wherein the absorbent composite is disposed between the topsheet and the backsheet.

18. The absorbent composite of claim 7 wherein the composite is present in an absorbent article selected from personal care absorbent articles, health/medical absorbent articles, household/industrial absorbent articles or sports/construction absorbent articles.

19. An absorbent system comprising:
   a SAP, a deswell triggering agent ($TA_D$) and a reswell triggering agent ($TA_R$);
   wherein the SAP, the $TA_D$ and the $TA_R$ are all selected from either solubility-based chemistry or neutralization-based chemistry groupings;
   wherein the absorbent system comprises an absorbent composite, a top discrete layer, and a bottom discrete layer;
   wherein the absorbent composite includes a fibrous matrix;

wherein the absorbent composite is disposed between the top discrete layer and the bottom discrete layer; and wherein the absorbent composite, the top discrete layer, and the bottom discrete layer each comprise exclusively only one of the SAP, the $TA_D$, and the $TA_R$.

20. The absorbent composite of claim 19 wherein the SAP is a superabsorbent polymer composition.

21. The absorbent composite of claim 19 wherein $TA_D$ comprises a first water-soluble solid chemical wherein the $TA_D$ has a release profile for releasing the water-soluble solid chemical wherein the release profile is selected from a singular release profile or a sigmoidal release profile; wherein the $TA_R$ comprises a second water-soluble solid chemical wherein the reswell triggering agent has a sigmoidal release profile for releasing the second water-soluble solid chemical; and wherein the first water-soluble chemical has a higher cumulative release than the second water-soluble chemical after exposure to aqueous fluid and before about 100% release.

22. The absorbent system of claim 19 wherein the absorbent composite comprises substantially only the SAP; wherein the top discrete layer comprises substantially only the $TA_D$; and wherein the bottom discrete layer comprises substantially only the $TA_R$.

23. The absorbent system of claim 19 wherein the absorbent composite comprises substantially only the SAP; wherein the top discrete layer comprises substantially only the $TA_D$; wherein the bottom discrete layer comprises substantially only the $TA_R$; and wherein at least one of the $TA_D$ and the $TA_R$ is located substantially only in a target zone of the top discrete layer and/or bottom discrete layer, respectively.

24. The absorbent system of claim 19 wherein the absorbent composite comprises substantially only the SAP; and wherein the $TA_D$ and the $TA_R$ are located substantially only in a target zone of at least one of the top discrete layer and/or bottom discrete layer.

25. The absorbent system of claim 19 further comprising a first intermediate discrete layer and a second intermediate discrete layer, wherein the first intermediate discrete layer is disposed between the top discrete layer and the absorbent composite, and wherein the second intermediate discrete layer is disposed between the absorbent composite and the bottom discrete layer; wherein the top discrete layer and the bottom discrete layer each comprise substantially only SAP; wherein the absorbent composite comprises substantially SAP; and wherein the first intermediate discrete layer and the second intermediate discrete layer each comprise the SAP, the $TA_D$ and the $TA_R$ combined.

26. The absorbent system of claim 19 further comprising a first intermediate discrete layer and a second intermediate discrete layer, wherein the first intermediate discrete layer is disposed between the top discrete layer and the absorbent composite, and wherein the second intermediate discrete layer is disposed between the absorbent composite and the bottom discrete layer; wherein the top discrete layer and the bottom discrete layer each comprise substantially only the SAP; wherein the absorbent composite comprises substantially only SAP; wherein the first intermediate discrete layer comprises substantially only the $TA_D$; and wherein the second intermediate discrete layer comprises substantially only the $TA_R$.

27. The absorbent system of claim 19 wherein the absorbent system is present in an absorbent article which further comprises a topsheet and a backsheet, wherein the absorbent composite is disposed between the topsheet and the backsheet.

28. The absorbent system of claim 19 wherein the absorbent system is present in an absorbent article selected from personal care absorbent articles, health/medical absorbent articles, household/industrial absorbent articles or sports/construction absorbent articles.

* * * * *